United States Patent
Harding et al.

(10) Patent No.: US 9,315,573 B2
(45) Date of Patent: Apr. 19, 2016

(54) ANTI-TNF-ALPHA ANTIBODIES AND THEIR USES

(71) Applicant: AbbVie Biotherapeutics Inc., Redwood City, CA (US)

(72) Inventors: Fiona A. Harding, Santa Clara, CA (US); Yoshiko Akamatsu, Palo Alto, CA (US); Robert B. Dubridge, Belmont, CA (US); David B. Powers, Fairfax, CA (US)

(73) Assignee: AbbVie Biotherapeutics Inc., Redwood City, CA (US)

( * ) Notice: Subject to any disclaimer, the term of this patent is extended or adjusted under 35 U.S.C. 154(b) by 0 days.

(21) Appl. No.: 14/194,090

(22) Filed: Feb. 28, 2014

(65) Prior Publication Data

US 2014/0212424 A1    Jul. 31, 2014

Related U.S. Application Data

(62) Division of application No. 12/761,745, filed on Apr. 16, 2010, now Pat. No. 8,722,860.

(60) Provisional application No. 61/170,053, filed on Apr. 16, 2009.

(51) Int. Cl.
*A61K 39/395* (2006.01)
*C07K 16/24* (2006.01)

(52) U.S. Cl.
CPC ........... *C07K 16/241* (2013.01); *C07K 2317/56* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

WO    WO 2007/120720 A2    10/2007

OTHER PUBLICATIONS

Agusti et al. PLoS One. 2012;7(5):e37483. Epub May 18, 2012.*
Jordana et al. Immune-inflammatory functions of fibroblasts. Eur Respir J. Dec. 1994;7(12):2212-22.*
MacCallum et al. Antibody-antigen interactions: contact analysis and binding site topography. J Mol Biol. Oct. 11, 1996;262(5):732-45.*
Vajdos et al. Comprehensive functional maps of the antigen-binding site of an anti-ErbB2 antibody obtained with shotgun scanning mutagenesis. J Mol Biol. Jul. 5, 2002;320(2):415-28.*
Wu et al. Humanization of a murine monoclonal antibody by simultaneous optimization of framework and CDR residues. J Mol Biol. Nov. 19, 1999;294(1)1 51-62.*
Zuvich et al. Genetics and pathogenesis of multiple sclerosis. Semin Immunol. Dec. 2009;21(6):328-33.*
Chen et al. Generation and analysis of random point mutations in an antibody CDR2 sequence: many mutated antibodies lose their ability to bind antigen. J Exp Med. Sep. 1, 1992;176(3):855-66.*
Rajpal et al. A general method for greatly improving the affinity of antibodies by using combinatorial libraries. Proc Natl Acad Sci U S A. Jun. 14, 2005;102(24):8466-71. Epub Jun. 6, 2005.*

* cited by examiner

*Primary Examiner* — David Romeo
(74) *Attorney, Agent, or Firm* — Dechert LLP

(57) ABSTRACT

The present disclosure relates to antibodies directed to the tumor necrosis factor alpha ("TNF-α") and uses of such antibodies, for example, to treat diseases associated with the activity and/or overproduction of TNF-α.

36 Claims, 28 Drawing Sheets

| D2E7 Heavy Chain Peptides || D2E7 Light Chain Peptides ||
|---|---|---|---|
| SEQ ID NO: | Peptide sequence | SEQ ID NO: | Peptide sequence |
| 11 | EVQLVESGGGLVQPG | 48 | DIQMTQSPSSLSASV |
| 12 | LVESGGGLVQPGRSL | 49 | MTQSPSSLSASVGDR |
| 13 | SGGGLVQPGRSLRLS | 50 | SPSSLSASVGDRVTI |
| 14 | GLVQPGRSLRLSCAA | 51 | SLSASVGDRVTITCR |
| 15 | QPGRSLRLSCAASGF | 52 | ASVGDRVTITCRASQ |
| 16 | RSLRLSCAASGFTFD | 53 | GDRVTITCRASQGIR |
| 17 | RLSCAASGFTFDDYA | 54 | VTITCRASQGIRNYL |
| 18 | CAASGFTFDDYAMHW | 55 | TCRASQGIRNYLAWY |
| 19 | SGFTFDDYAMHWVRQ | 56 | ASQGIRNYLAWYQQK |
| 20 | TFDDYAMHWVRQAPG | 57 | GIRNYLAWYQQKPGK |
| 21 | DYAMHWVRQAPGKGL | 58 | NYLAWYQQKPGKAPK |
| 22 | MHWVRQAPGKGLEWV | 59 | AWYQQKPGKAPKLLI |
| 23 | VRQAPGKGLEWVSAI | 60 | QQKPGKAPKLLIYAA |
| 24 | APGKGLEWVSAITWN | 61 | PGKAPKLLIYAASTL |
| 25 | KGLEWVSAITWNSGH | 62 | APKLLIYAASTLQSG |
| 26 | EWVSAITWNSGHIDY | 63 | LLIYAASTLQSGVPS |
| 27 | SAITWNSGHIDYADS | 64 | YAASTLQSGVPSRFS |
| 28 | TWNSGHIDYADSVEG | 65 | STLQSGVPSRFSGSG |
| 29 | SGHIDYADSVEGRFT | 66 | QSGVPSRFSGSGSGT |
| 30 | IDYADSVEGRFTISR | 67 | VPSRFSGSGSGTDFT |
| 31 | ADSVEGRFTISRDNA | 68 | RFSGSGSGTDFTLTI |
| 32 | VEGRFTISRDNAKNS | 69 | GSGSGTDFTLTISSL |
| 33 | RFTISRDNAKNSLYL | 70 | SGTDFTLTISSLQPE |
| 34 | ISRDNAKNSLYLQMN | 71 | DFTLTISSLQPEDVA |
| 35 | DNAKNSLYLQMNSLR | 72 | LTISSLQPEDVATYY |
| 36 | KNSLYLQMNSLRAED | 73 | SSLQPEDVATYYCQR |
| 37 | LYLQMNSLRAEDTAV | 74 | QPEDVATYYCQRYNR |
| 38 | QMNSLRAEDTAVYYC | 75 | DVATYYCQRYNRAPY |
| 39 | SLRAEDTAVYYCAKV | 76 | DVATYYCQRYNRAPY |
| 40 | AEDTAVYYCAKVSYL | 77 | TYYCQRYNRAPYTFG |
| 41 | TAVYYCAKVSYLSTA | 78 | CQRYNRAPYTFGQGT |
| 42 | YYCAKVSYLSTASSL | 79 | YNRAPYTFGQGTKVE |
| 43 | AKVSYLSTASSLDYW | 80 | RAPYTFGQGTKVEIK |
| 44 | SYLSTASSLDYWGQG | | |
| 45 | STASSLDYWGQGTLV | | |
| 46 | SSLDYWGQGTLVTVS | | |
| 47 | SLDYWGQGTLVTVSS | | |

FIG. 1

| Region | Peptide number | Sequence | SEQ ID NO: |
|---|---|---|---|
| VH | 20 | IDYADSVEGRFTISR | 81 |
| VL | 8 | TCRASQGIRNYLAWY | 82 |
| VL | 11 | NYLAWYQQKPGKAPK | 83 |

FIG. 2

| Region | Peptide number | Peptide | HLA | Fisher P | Relative risk |
|---|---|---|---|---|---|
| VL | 8 | T22-Y36 | none | | |
| VL | 11 | N31-K45 | DQ2 | 0.003 | 7.7 |
| VL | 11 | | DR3 | 0.1 | 3.3 |
| VL | 11 | | DR12 | 0.03 | 5.2 |

FIG. 3

| Epitope variant peptide | Peptide No. | SEQ ID NO: | # Responders | n | % Responders | Average SI |
|---|---|---|---|---|---|---|
| CRASQGIRNYLAWYQQKPGKAPK | 1 | 84 | 11 | 99 | 11.11 | 1.49 |
| ARASQGIRNYLAWYQQKPGKAPK | 2 | 85 | 2 | 99 | 2.02 | 1.24 |
| CAASQGIRNYLAWYQQKPGKAPK | 3 | 86 | 7 | 99 | 7.07 | 1.24 |
| CRASQGIRNYLAWYQQKPGKAPK | 4 | 87 | 5 | 99 | 5.05 | 1.28 |
| CRAAQGIRNYLAWYQQKPGKAPK | 5 | 88 | 9 | 99 | 9.09 | 1.42 |
| CRASAGIRNYLAWYQQKPGKAPK | 6 | 89 | 11 | 99 | 11.11 | 1.44 |
| CRASQAIRNYLAWYQQKPGKAPK | 7 | 90 | 5 | 99 | 5.05 | 1.24 |
| CRASQGARNYLAWYQQKPGKAPK | 8 | 91 | 5 | 99 | 5.05 | 1.33 |
| CRASQGIANYLAWYQQKPGKAPK | 9 | 92 | 10 | 99 | 11.11 | 1.63 |
| CRASQGIRAYLAWYQQKPGKAPK | 10 | 93 | 5 | 99 | 5.05 | 1.16 |
| CRASQGIRNALAWYQQKPGKAPK | 11 | 94 | 4 | 99 | 4.04 | 1.20 |
| CRASQGIRNYAAWYQQKPGKAPK | 12 | 95 | 6 | 99 | 6.06 | 1.30 |
| CRASQGIRNYLAWYQQKPGKAPK | 13 | 96 | 9 | 99 | 9.09 | 1.49 |
| CRASQGIRNYLAAYQQKPGKAPK | 14 | 97 | 10 | 99 | 10.10 | 1.49 |
| CRASQGIRNYLAWAQQKPGKAPK | 15 | 98 | 10 | 99 | 10.10 | 2.00 |
| CRASQGIRNYLAWYAQKPGKAPK | 16 | 99 | 9 | 99 | 9.09 | 1.38 |
| CRASQGIRNYLAWYQAKPGKAPK | 17 | 100 | 12 | 99 | 12.12 | 1.47 |
| CRASQGIRNYLAWYQQAPGKAPK | 18 | 101 | 6 | 99 | 6.06 | 1.41 |
| CRASQGIRNYLAWYQQKAGKAPK | 19 | 102 | 3 | 99 | 3.03 | 1.17 |
| CRASQGIRNYLAWYQQKPAKAPK | 20 | 103 | 8 | 99 | 8.08 | 1.61 |
| CRASQGIRNYLAWYQQKPGAAPK | 21 | 104 | 10 | 99 | 10.10 | 1.79 |
| CRASQGIRNYLAWYQQKPGKAPK | 22 | 105 | 8 | 99 | 8.08 | 1.46 |
| CRASQGIRNYLAWYQQKPGKAAK | 23 | 106 | 6 | 99 | 6.06 | 1.30 |
| CRASQGIRNYLAWYQQKPGKAPA | 24 | 107 | 12 | 99 | 12.12 | 1.62 |

FIG. 4

| WT CDR-L1 SEQ ID NO:8 | Position | Candidate substitutions |
|---|---|---|
| R | 24 | - |
| A | 25 | W |
| S | 26 | - |
| Q | 27 | G, H, R, T |
| G | 28 | S |
| I | 29 | T, V |
| R | 30 | Q |
| N | 31 | S, T |
| Y | 32 | - |
| L | 33 | E |
| A | 34 | G, S |

FIG. 5

| Variant | BIAcore | | | | | | ELISA |
|---|---|---|---|---|---|---|---|
| | $k_{on}$ (1/Ms) | $k_{off}$ (1/s) | $K_D$ (pM) | n | CV% | WT/x | WT/x |
| A25W | 1.14E+6 | 2.21E-4 | 195 | 3 | 12 | 0.59 | 1.26 |
| Q27R | 9.96E+5 | 1.04E-4 | 106 | 3 | 15 | 1.09 | 1.27 |
| Q27T | 1.10E+6 | 1.43E-4 | 131 | 3 | 10 | 0.89 | 0.86 |
| I29V | 1.27E+6 | 9.45E-5 | 74 | 3 | 15 | 1.56 | 1.03 |
| R30Q | 1.42E+6 | 3.32E-4 | 240 | 3 | 23 | 0.48 | 0.30 |
| L33E | 1.23E+6 | 1.54E-4 | 126 | 3 | 14 | 0.92 | 0.69 |
| WT | 1.13E+6 | 1.31E-4 | 116 | 3 | 14 | 1.00 | 1.00 |

FIG. 6

| Epitope variant peptides | SEQ ID NO: | # Responders | n | % Responders | Average SI |
|---|---|---|---|---|---|
| TCRASQGIRNYLAWYQQKPGKAPK | 108 | 12 | 102 | 11.76 | 1.60 |
| TCRASNGIRNYLAWYQQKPGKAPK | 109 | 12 | 102 | 11.76 | 1.79 |
| TCRASGGIRNYLAWYQQKPGKAPK | 110 | 18 | 102 | 17.65 | 2.59 |
| TCRASHGIRNYLAWYQQKPGKAPK | 111 | 7 | 102 | 6.86 | 1.34 |
| TCRASSGIRNYLAWYQQKPGKAPK | 112 | 19 | 102 | 18.63 | 3.50 |
| TCRASRGIRNYLAWYQQKPGKAPK | 113 | 12 | 102 | 11.76 | 2.25 |
| TCRASQSIRNYLAWYQQKPGKAPK | 114 | 15 | 102 | 14.71 | 2.09 |
| TCRASQHIRNYLAWYQQKPGKAPK | 115 | 12 | 102 | 11.76 | 1.58 |
| TCRASQNIRNYLAWYQQKPGKAPK | 116 | 7 | 102 | 6.86 | 1.36 |
| TCRASQGVRNYLAWYQQKPGKAPK | 117 | 11 | 102 | 10.78 | 1.59 |
| TCRASQGTRNYLAWYQQKPGKAPK | 118 | 6 | 102 | 5.88 | 1.33 |
| TCRASQGIQNYLAWYQQKPGKAPK | 119 | 3 | 102 | 2.94 | 1.33 |
| TCRASQGIRGYLAWYQQKPGKAPK | 120 | 19 | 102 | 18.63 | 2.58 |
| TCRASQGIRTYLAWYQQKFGKAPK | 121 | 5 | 102 | 4.90 | 1.09 |
| TCRASQGIRSQLAWYQQKPGKAPK | 122 | 3 | 102 | 2.94 | 1.14 |
| TCRASQGIRNSLAWYQQKPGKAPK | 123 | 5 | 102 | 4.90 | 1.21 |
| TCRASQGIRNYLGWYQQKPGKAPK | 124 | 4 | 102 | 3.92 | 1.27 |
| TCRASQGIRNYLSWYQQKPGKAPK | 125 | 5 | 102 | 4.90 | 1.27 |
| TCRASNGIRNQLAWYQQKPGKAPK | 126 | 2 | 102 | 1.96 | 1.23 |
| TCRASGGIRNQLAWYQQKPGKAPK | 127 | 14 | 102 | 13.73 | 2.12 |
| TCRASHGIRNQLAWYQQKPGKAPK | 128 | 6 | 102 | 5.88 | 1.42 |
| TCRASSGIRNQLAWYQQKPGKAPK | 129 | 3 | 102 | 2.94 | 1.18 |
| TCRASRGIRNQLAWYQQKPGKAPK | 130 | 3 | 102 | 2.94 | 0.97 |
| TCRASQSIRNQLAWYQQKPGKAPK | 131 | 3 | 102 | 2.94 | 1.21 |
| TCRASQHIRNQLAWYQQKPGKAPK | 132 | 21 | 102 | 20.59 | 2.07 |
| TCRASQNIRNQLAWYQQKPGKAPK | 133 | 7 | 102 | 6.86 | 1.39 |
| TCRASQGVRNQLAWYQQKPGKAPK | 134 | 3 | 102 | 2.94 | 1.12 |
| TCRASQGTRNQLAWYQQKPGKAPK | 135 | 18 | 102 | 17.65 | 2.48 |
| TCRASQGIQNQLAWYQQKPGKAPK | 136 | 5 | 102 | 4.90 | 1.10 |
| TCRASQGIRGQLAWYQQKPGKAPK | 137 | 4 | 102 | 3.92 | 1.12 |
| TCRASQGIRTQLAWYQQKPGKAPK | 138 | 2 | 102 | 1.96 | 1.21 |
| TCRASQGIRSQLAWYQQKPGKAPK | 139 | 3 | 102 | 2.94 | 1.26 |
| TCRASQGIRSQLGWYQQKPGKAPK | 140 | 7 | 102 | 6.86 | 1.36 |
| TCRASQGIRSQLSWYQQKPGKAPK | 141 | 4 | 102 | 3.92 | 1.25 |
| TCRASNGIRNSLAWYQQKPGKAPK | 142 | 1 | 102 | 0.98 | 1.07 |
| TCRASGGIRNSLAWYQQKPGKAPK | 143 | 1 | 102 | 0.98 | 1.08 |
| TCRASHGIRNSLAWYQQKPGKAPK | 144 | 6 | 102 | 5.88 | 1.22 |
| TCRASSGIRNSLAWYQQKPGKAPK | 145 | 2 | 102 | 1.96 | 1.14 |
| TCRASRGIRNSLAWYQQKPGKAPK | 146 | 5 | 102 | 4.90 | 1.41 |

FIG. 7

| Epitope variant peptides | SEQ ID NO: | # Responders | n | % Responders | Average SI |
|---|---|---|---|---|---|
| TCRASQSIRNSLAWYQQKPGKAPK | 147 | 7 | 102 | 6.86 | 1.48 |
| TCRASQHIRNSLAWYQQKPGKAPK | 148 | 12 | 102 | 11.76 | 1.66 |
| TCRASQNIRNSLAWYQQKPGKAPK | 149 | 2 | 102 | 1.96 | 1.21 |
| TCRASQGVRNSLAWYQQKPGKAPK | 150 | 3 | 102 | 2.94 | 1.04 |
| TCRASQGTRNSLAWYQQKPGKAPK | 151 | 3 | 102 | 2.94 | 1.03 |
| TCRASQGIQNSLAWYQQKPGKAPK | 152 | 1 | 102 | 0.98 | 0.94 |
| TCRASQGIRGSLAWYQQKPGKAPK | 153 | 2 | 102 | 1.96 | 1.11 |
| TCRASQGIRTSLAWYQQKPGKAPK | 154 | 0 | 102 | 0.00 | 0.99 |
| TCRASQGIRSSLAWYQQKPGKAPK | 155 | 1 | 102 | 0.98 | 1.11 |
| TCRASQGIRNSLGWYQQKPGKAPK | 156 | 9 | 102 | 8.82 | 1.51 |
| TCRASQGIRNSLSWYQQKPGKAPK | 157 | 6 | 102 | 5.88 | 1.47 |
| TCRASNGIRNYLGWYQQKPGKAPK | 158 | 5 | 102 | 4.90 | 1.36 |
| TCRASGGIRNYLGWYQQKPGKAPK | 159 | 3 | 102 | 2.94 | 1.10 |
| TCRASHGIRNYLGWYQQKPGKAPK | 160 | 4 | 102 | 3.92 | 1.19 |
| TCRASSGIRNYLGWYQQKPGKAPK | 161 | 4 | 102 | 3.92 | 1.18 |
| TCRASRGIRNYLGWYQQKPGKAPK | 162 | 4 | 102 | 3.92 | 1.33 |
| TCRASQSIRNYLGWYQQKPGKAPK | 163 | 7 | 102 | 6.86 | 1.49 |
| TCRASQHIRNYLGWYQQKPGKAPK | 164 | 6 | 102 | 5.88 | 1.32 |
| TCRASQNIRNYLGWYQQKPGKAPK | 165 | 5 | 102 | 4.90 | 1.39 |
| TCRASQGVRNYLGWYQQKPGKAPK | 166 | 5 | 102 | 4.90 | 1.18 |
| TCRASQGTRNYLGWYQQKPGKAFK | 167 | 2 | 102 | 1.96 | 1.18 |
| TCRASQGIQNYLGWYQQKPGKAPK | 168 | 5 | 102 | 4.90 | 1.26 |
| TCRASQGIRGYLGWYQQKPGKAPK | 169 | 6 | 102 | 5.88 | 1.34 |
| TCRASQGIRTYLGWYQQKPGKAPK | 170 | 3 | 102 | 2.94 | 1.10 |
| TCRASQGIRSYLGWYQQKPGKAPK | 171 | 5 | 102 | 4.90 | 1.35 |
| TCRASNGIRNYLSWYQQKPGKAPK | 172 | 14 | 102 | 13.73 | 1.67 |
| TCRASGGIRNYLSWYQQKPGKAPK | 173 | 12 | 102 | 11.76 | 1.59 |
| TCRASHGIRNYLSWYQQKPGKAPK | 174 | 3 | 102 | 2.94 | 1.26 |
| TCRASSGIRNYLSWYQQKPGKAPK | 175 | 8 | 102 | 7.84 | 1.29 |

FIG. 7, continued

| Peptide | Epitope variant peptides | SEQ ID NO: | Rank | n | % Responders | Average SI |
|---|---|---|---|---|---|---|
| R30Q/A34AS | TCRASQGIQNYLSWYQQKPGKAPK | 176 | 1 | 102 | 0.98 | 1.23 |
| N31T/A34S | TCRASQGIRTYLSWYQQKPGKAPK | 177 | 1 | 102 | 0.98 | 1.01 |
| I29T/A34G | TCRASQGTRNYLGWYQQKPGKAFK | 167 | 2 | 102 | 1.96 | 1.18 |
| R30Q | TCRASQGIQNYLAWYQQKPGKAPK | 119 | 3 | 102 | 2.94 | 1.33 |
| Q27G/A34G | TCRASGGIRNYLGWYQQKPGKAPK | 159 | 3 | 102 | 2.94 | 1.10 |
| N31T/A34G | TCRASQGIRTYLGWYQQKPGKAPK | 170 | 3 | 102 | 2.94 | 1.10 |
| Q27H/A34S | TCRASHGIRNYLSWYQQKPGKAPK | 174 | 3 | 102 | 2.94 | 1.26 |
| Q27R/A34S | TCRASRGIRNYLSWYQQKPGKAPK | 178 | 3 | 102 | 2.94 | 1.06 |
| G28S/A34S | TCRASQSIRNYLSWYQQKPGKAPK | 179 | 3 | 102 | 2.94 | 1.16 |
| N31S/A34S | TCRASQGIRSYLSWYQQKPGKAPK | 180 | 3 | 102 | 2.94 | 1.15 |

FIG. 8

| Peptide | IC$_{50}$ (nM) | Difference to WT |
|---|---|---|
| I29T/A34G | 1.24 | 0.77 |
| N31T/A34G | 1.52 | 0.63 |
| R30Q/A34S | 1.30 | 0.73 |
| R30Q | 1.20 | 0.79 |
| Q27G/A34G | 1.07 | 0.89 |
| Q27H/A34S | 1.02 | 0.94 |
| Q27R/A34S | 0.97 | 0.98 |
| G28S/A34S | 1.08 | 0.88 |
| N31T/A34S | 1.35 | 0.71 |
| N31S/A34S | 1.49 | 0.64 |
| parent | 0.95 | 1.00 |

FIG. 9

| variants | BIAcore | | | | | |
| --- | --- | --- | --- | --- | --- | --- |
| | $k_{on}$ (1/Ms) | $k_{off}$ (1/s) | $K_D$ (pM) | n | CV % | WT/x |
| I29T/A34G | 9.87 E+5 | 6.49 E-4 | 657 | 3 | 7 | 0.18 |
| N31T/A34G | 2.31 E+6 | 3.19 E-3 | 1440 | 3 | 13 | 0.08 |
| R30Q/A34S | 1.17 E+6 | 6.03 E-4 | 520 | 3 | 17 | 0.22 |
| R30Q | 1.42 E+6 | 3.32 E-4 | 240 | 3 | 23 | 0.48 |
| Q27G/A34G | 1.11 E+6 | 2.89 E-4 | 262 | 3 | 16 | 0.44 |
| Q27H/A34S | 1.16 E+6 | 1.54 E-4 | 133 | 3 | 10 | 0.87 |
| Q27R/A34S | 9.82 E+5 | 1.24 E-4 | 128 | 3 | 19 | 0.91 |
| G28S/A34S | 1.18 E+6 | 1.53 E-4 | 131 | 3 | 11 | 0.89 |
| N31T/A34S | 1.31 E+6 | 1.46 E-3 | 1110 | 3 | 4 | 0.10 |
| N31S/A34S | 1.64 E+6 | 1.93 E-3 | 1220 | 3 | 20 | 0.10 |
| WT | 1.13 E+6 | 1.31 E-4 | 116 | 3 | 14 | 1.00 |

FIG. 10

| CDR-L1 WT & VARIANT SEQ ID NOS | | | | | | | | | | | |
|---|---|---|---|---|---|---|---|---|---|---|---|
| 8 (WT) | R | A | S | Q | G | I | R | N | Y | L | A |
| 181 | | | | | | | Q | | | | |
| 182 | | | | | | | | | | | S |
| 183 | | | | | | | Q | | | | S |
| 184 | | | | | | | | T | | | |
| 185 | | | | | | | | T | | | S |
| 186 | | | | | | T | | | | | |
| 187 | | | | | | | | | | | G |
| 188 | | | | | | T | | | | | G |
| 189 | | | | G | | | | | | | |
| 190 | | | | G | | | | | | | S |
| 191 | | | | G | | | | | | | G |
| 192 | | | | | | | | T | | | G |
| 193 | | | | H | | | | | | | |
| 194 | | | | H | | | | | | | S |
| 195 | | | | R | | | | | | | |
| 196 | | | | R | | | | | | | S |
| 197 | | | S | | | | | | | | |
| 198 | | | S | | | | | | | | S |
| 199 | | | | | | | | S | | | S |
| 200 | | | | | | T | | | | | S |
| 201 | | | | | | | | T | | | G |

FIG. 11

| variant | chain | CDR | BIAcore | | | | | | ELISA |
|---|---|---|---|---|---|---|---|---|---|
| | | | $k_{on}$ (1/Ms) | $k_{off}$ (1/s) | $K_D$ (pM) | n | CV% | WT/x | WT/x |
| T53F | VL | 2 | 1.21E+6 | 9.49E-5 | 79 | 3 | 7 | 1.47 | 1.54 |
| T53W | VL | 2 | 1.03E+6 | 9.38E-5 | 91 | 3 | 7 | 1.27 | 1.92 |
| T53Y | VL | 2 | 1.18e+6 | 9.56E-5 | 82 | 4 | 17 | 1.42 | ND |
| L54R | VL | 2 | 1.27E+6 | 1.14E-4 | 91 | 3 | 13 | 1.28 | 1.82 |
| L54K | VL | 2 | 1.12E+6 | 9.17E-5 | 82 | 3 | 7 | 1.42 | 1.25 |
| Q55R | VL | 2 | 1.19E+6 | 1.14E-4 | 96 | 3 | 13 | 1.22 | 1.33 |
| D31G | VH | 1 | 1.51E+6 | 8.13E-5 | 55 | 3 | 13 | 2.11 | 0.97 |
| Y32H | VH | 1 | 1.32 E+6 | 1.00E- 4 | 78 | 4 | 24 | 1.49 | ND |
| A33G | VH | 1 | 1.40E+6 | 2.13E-4 | 153 | 3 | 19 | 0.76 | 1.30 |
| T52N | VH | 2 | 1.65E+6 | 1.60E-4 | 99 | 3 | 18 | 1.18 | 0.94 |
| WT | | | 1.13E+6 | 1.31E-4 | 116 | 3 | 14 | 1.00 | 1.00 |

FIG. 12

| CDR-H1 WT & VARIANT SEQ ID NOS | | | | | |
|---|---|---|---|---|---|
| 5 (WT) | D | Y | A | M | H |
| 202 | | | T | | |
| 203 | E | | | | |
| 204 | Q | H | | L | |
| 205 | Q | H | | | |
| 206 | H | | | L | |
| 207 | Q | | | | |
| 208 | H | | | | |
| 209 | Y | | | | |

FIG. 13

| CDR-H2 WT & VARIANT SEQ ID NOS | | | | | | | | | | | | | | | | |
|---|---|---|---|---|---|---|---|---|---|---|---|---|---|---|---|---|
| 6 (WT) | A | I | T | W | N | S | G | H | I | D | Y | A | D | S | V | E | G |
| 210 | PA | | | | | | | | | | | | | | | | |
| 211 | ▨ | | | | | | | | | | | | | | | | |

FIG. 14

| CDR-H3 WT & VARIANT SEQ ID NOS | | | | | | | | | | |
|---|---|---|---|---|---|---|---|---|---|---|
| 7 (WT) | V | S | Y | L | S | T | A | S | S | L | D | Y |
| 212 | PV | | | | | | | | | | | X |
| 213 | PA | | | | | | | | | | | |
| 214 | PA | | | | | S | | | | | | |
| 215 | | | | | | | | | | | | N |
| 216 | | | | | | | | | | | | X |
| 217 | A | | | | | S | | | | | | |
| 218 | V | | | | | | | | | | Q | |
| 219 | A | | | | | | | | | | Q | |
| 220 | | | | | | S | | | | | | |
| 221 | A | | | | | | | | | | E | |
| 222 | A | | | | | S | | | | | | N |
| 223 | A | | | | | S | | | | | | K |
| 224 | A | | | | | S | | | | | | D |
| 225 | A | | | | | S | F | | | | | |
| 226 | | | | | | | | | | | | A |
| 227 | A | | | | | S | | | | | E | |
| 228 | | | | | | S | | | | | | N |
| 229 | | | | | | | | | | A | | |
| 230 | | | | | | | | | | | A | |
| 231 | | A | | | | | | | | | | |
| 232 | | | A | | | | | | | | | |
| 233 | | | | A | | | | | | | | |
| 234 | | | | | A | | | | | | | |
| 235 | | | | | | A | | | | | | |
| 236 | | | | | | | A | | | | | |
| 237 | | | | | | | | A | | | | |
| 238 | | | | | | | | | | | Q | X |
| 239 | | | | | | | | | | | Q | |
| 240 | | | A | S | T | G | P | | | V | F | P | L |
| 241 | | H | | | | | | | | | | |
| 242 | | H | | | | | | | | Q | H | H |
| 243 | | Q | | | | | | | | | | |
| 244 | | K | | | | | | | | | | |
| 245 | | P | | | | | | | | | | |
| 246 | | | | | | | | | P | | | |
| 247 | | | | | | | | | | | P | |
| 248 | | | | | | | | | | | | P |
| 249 | | | | | | | | | | | | S |
| 250 | A | | | | | | | | | | | |
| 251 | A | | | | | S | | | | | H | |
| 252 | A | F | | | | S | | | | | E | |

FIG. 15

| CDR-L1 WT & VARIANT SEQ ID NOS | | | | | | | | | | |
|---|---|---|---|---|---|---|---|---|---|---|
| 8 (WT) | R | A | S | Q | G | I | R | N | Y | L | A |
| 253 | PR | | | | | | | | | |
| 254 | | | | | | | | | D | | G |
| 255 | | | | | | | S | | | |
| 256 | | | R | | | | S | | | |
| 257 | | | | | S | | | SN | | |
| 258 | | | | | E | | | | | |
| 259 | H | | | | K | | | | | |
| 260 | | | | | L | | | | | |
| 261 | | | | | | | S | S | | |
| 262 | | | | S | | | | | | |
| 263 | H | | | R | R | | | | | |
| 264 | H | | | R | R | L | | | | |
| 265 | H | | | R | K | L | | | | |
| 266 | H | | | R | K | | | | | |
| 267 | H | | | | K | | | | | |
| 268 | H | | | K | R | | | | | |
| 269 | H | | | K | K | | | | | |
| 270 | H | | | R | E | | | | | |
| 271 | H | | | | | | | | | |
| 273 | G | | | | | | | | | |
| 274 | | | | K | | | | | | |
| 275 | | | | | K | | | | | |
| 276 | | | | | | K | | | | |
| 277 | | | | | | L | | | | |
| 278 | | | | Y | | | | | | |

FIG. 16

| CDR-L2 WT & VARIANT SEQ ID NOS | | | | | | |
|---|---|---|---|---|---|---|
| 9 (WT) | A | A | S | T | L | Q | S |
| 279 | PA | | | | | |
| 280 | | | | S | | L | H |
| 281 | | | | S | | | P |
| 282 | | | | S | | L | R |
| 283 | | | | S | | L | K |
| 284 | | | | S | | | Q |
| 285 | | | | S | | L | P |
| 286 | | | | S | | L | Q |
| 287 | | | | | | L | K |
| 288 | | | | A | | | |
| 289 | | | | | F | | |
| 290 | | | | | | | K |
| 291 | | | L | | | | |
| 292 | | | | | | L | |
| 293 | | | | | | | P |
| 294 | | | | S | | | |
| 295 | | | Y | | | | |

FIG. 17

| CDR-L3 WT & VARIANT SEQ ID NOS | | | | | | | | |
|---|---|---|---|---|---|---|---|---|
| 10 (WT) | Q | R | Y | N | R | A | P | Y | T |
| 296 | PQ | K | | | | | | | |
| 297 | PQ | | | | | | | | X |
| 298 | PQ | | | | | | | | A |
| 299 | | K | | | | | | | |
| 300 | | | | | | | | | A |
| 301 | | | | | | | | | X |
| 302 | | | | | | | | | T |
| 303 | | K | | | S | | | | A |
| 304 | | K | | | | | | | A |
| 305 | | K | | N | | | | | |
| 306 | | K | | S | S | | | | |
| 307 | | K | | | S | | | | |
| 308 | | K | | | S | | | | Y |
| 309 | | K | | | S | | | | N |
| 310 | | K | | T | S | | | | |
| 311 | | K | | | | | | | N |
| 312 | | K | | | S | | A | | S |
| 313 | | Q | | | S | | | D | |
| 314 | | K | | | S | D | | | |
| 315 | | K | | I | S | | | | |
| 316 | | K | | | | P | | | |
| 317 | | | | | D | | | | |
| 318 | | | | A | | | | | |
| 319 | | | | | A | | | | |
| 320 | | | | | | A | | | |
| 321 | | | | | | | A | | |
| 322 | | P | E | D | F | | T | | Y |
| 323 | | S | D | | F | | T | | Y |
| 324 | | | | D | K | P | | | |
| 325 | | | | | K | P | | | |

FIG. 18

| CDR-L3 WT & VARIANT SEQ ID NOS | | | | | | | | |
|---|---|---|---|---|---|---|---|---|
| 10 (WT) | Q | R | Y | N | R | A | P | Y | T |
| 326 | | | | D | | P | | |
| 327 | | | | D | | | | |
| 328 | | | | | K | | | |
| 329 | | | | | | P | | |
| 330 | | K | | Q | | | | |
| 331 | | K | | S | S | | | A |
| 332 | A | | | | | | | |
| 333 | | A | | | | | | |
| 334 | | | A | | | | | |
| 335 | | P | E | D | V | | T | Y |
| 336 | | P | E | D | V | | A | Y |

FIG. 18, continued

| CDR-H1 WT & VARIANT SEQ ID NOS | | | | |
|---|---|---|---|---|
| 5 (WT) | D | Y | A | M | H |
| 337 | N | | | | |
| 338 | T | | | | |
| 339 | R | | | | |
| 340 | | F | | | |
| 341 | | Q | | | |
| 342 | | | | I | |

FIG. 19

| CDR-H2 WT & VARIANT SEQ ID NOS | | | | | | | | | | | | | | | |
|---|---|---|---|---|---|---|---|---|---|---|---|---|---|---|---|
| 6 (WT) | A | I | T | W | N | S | G | H | I | D | Y | A | D | S | V | E | G |
| 343 | G | | | | | | | | | | | | | | | | |
| 344 | | | | | | | | | T | | | | | | | | |
| 345 | | | | | | | | | V | | | | | | | | |
| 346 | | | | | | | | | | | | | | | | R | |
| 347 | | | | | | | | | | | | | | | | | N |

FIG. 20

| CDR-H3 WT & VARIANT SEQ ID NOS | | | | | | | | | | | |
|---|---|---|---|---|---|---|---|---|---|---|---|
| 7 (WT) | V | S | Y | L | S | T | A | S | S | L | Y |
| 348 | | | | | | | | P | | | |

FIG. 21

| CDR-L1 WT & VARIANT SEQ ID NOS | | | | | | | | | | |
|---|---|---|---|---|---|---|---|---|---|---|
| 8 (WT) | R | A | S | Q | G | I | R | N | Y | L | A |
| 349 | L | | | | | | | | | | |
| 350 | A | | | | | | | | | | |
| 351 | T | | | | | | | | | | |
| 352 | | S | | | | | | | | | |
| 353 | | G | | | | | | | | | |
| 354 | | T | | | | | | | | | |
| 355 | | | T | | | | | | | | |
| 356 | | | | M | | | | | | | |
| 357 | | | | V | | | | | | | |
| 358 | | | | W | | | | | | | |
| 359 | | | | | P | | | | | | |
| 360 | | | | | R | | | | | | |
| 361 | | | | | L | | | | | | |
| 362 | | | | | | V | | | | | |

FIG. 22

| CDR-L2 WT & VARIANT SEQ ID NOS | | | | | | |
|---|---|---|---|---|---|---|
| 9 (WT) | A | A | S | T | L | Q | S |
| 363 | | | G | | | | |
| 364 | | | W | | | | |
| 365 | | | | | G | | |
| 366 | | | | | | S | |
| 367 | | | | | | T | |
| 368 | | | | | | | I |
| 369 | | | | | | | R |

FIG. 23

| CDR-L3 WT & VARIANT SEQ ID NOS | | | | | | | | | |
|---|---|---|---|---|---|---|---|---|---|
| 10 (WT) | Q | R | Y | N | R | A | P | Y | T |
| 370 | | | | I | | | | | |
| 371 | | | | Q | | | | | |
| 372 | | | | M | | | | | |
| 373 | | | | | S | | | | |
| 374 | | | | | | | Q | | |
| 375 | | | | | | | A | | |
| 376 | | | | | | | S | | |
| 377 | | | | | | | M | | |
| 378 | | | | | | | E | | |
| 379 | | | | | | | V | | |

FIG. 24

| CDR-L2 WT & Variant SEQ ID NOS | CDR L2 sequence | | | | | | Ka (1/Ms) | Kd (1/s) | KA (1/M) | pM | Fold over WT |
|---|---|---|---|---|---|---|---|---|---|---|---|
| 9 (WT) | A | A | S | T | L | Q | 1.42E+06 | 1.98E-04 | 7.07E+09 | 144 | 1.00 |
| 380 | | | K | H | R | R | 8.26E+05 | 1.88E-04 | 4.43E+09 | 226 | 0.63 |
| 381 | | | K | Q | R | K | 9.15E+05 | 2.43E-04 | 3.76E+09 | 267 | 0.54 |
| 382 | | | K | Y | K | | 1.12E+06 | 1.49E-04 | 7.51E+09 | 134 | 1.07 |
| 383 | | | K | Y | | | 1.18E+06 | 1.58E-04 | 7.55E+09 | 134 | 1.07 |
| 384 | | | N | V | R | K | 1.28E+06 | 1.46E-04 | 9.03E+09 | 113 | 1.27 |
| 385 | | | N | W | R | R | 1.20E+06 | 7.78E-05 | 1.54E+10 | 65 | 2.20 |
| 386 | | | R | F | R | | 1.06E+06 | 1.17E-04 | 9.04E+09 | 111 | 1.29 |
| 387 | | | R | F | R | R | 5.74E+06 | 2.13E-04 | 2.06E+10 | 62 | 2.32 |
| 388 | | | R | H | | K | 8.05E+05 | 2.79E-04 | 2.99E+09 | 345 | 0.42 |
| 389 | | | R | W | K | R | 7.69E+05 | 2.05E-04 | 3.83E+09 | 271 | 0.53 |
| 390 | | | | H | K | K | 1.15E+06 | 1.03E-04 | 1.14E+10 | 89 | 1.62 |
| 391 | | | | H | K | R | 8.96E+05 | 2.49E-04 | 3.60E+09 | 278 | 0.52 |
| 392 | | | | W | R | R | 9.81E+05 | 1.75E-04 | 5.65E+09 | 177 | 0.81 |
| 272 | | | | Y | R | | 1.98E+06 | 8.24E-05 | 2.47E+10 | 43 | 3.37 |

FIG. 25

D2E7(Humira) VH (SEQ ID NO:2)

EVQLVESGGGLVQPGRSLRLSCAASGFTFDDYAMHWVRQAPGKGLEWVSAIT WNSGHIDYADSVEGRFTISRDNAKNSLYLQMNSLRAEDTAVYYCAKVSYLSTAS SLDYWGQGTLVTVSS

D2E7 (Humira) VL (SEQ ID NO:4)

DIQMTQSPSSLSASVGDRVTITCRASQGIRNYLAWYQQKPGKAPKLLIYAASTLQ SGVPSRFSGSGSGTDFTLTISSLQPEDVATYYCQRYNRAPYTFGQGTKVEIK

FIG. 26A

| Antibody Chain | CDR No. | Sequence | SEQ ID NO. |
|---|---|---|---|
| Heavy | 1 | DYAMH | 5 |
| Heavy | 2 | AITWNSGHIDYADSVEG | 6 |
| Heavy | 3 | VSYLSTASSLDY | 7 |
| Light | 1 | RASQGIRNYLA | 8 |
| Light | 2 | AASTLQS | 9 |
| Light | 3 | QRYNRAPYT | 10 |

FIG. 26B

| Antibody Chain | CDR No. | SEQ ID NO: | Residue | Position in CDR | Kabat No. |
|---|---|---|---|---|---|
| Heavy | 1 | 5 | D | 1 | 31 |
| | | | Y | 2 | 32 |
| | | | A | 3 | 33 |
| | | | M | 4 | 34 |
| | | | H | 5 | 35 |
| Heavy | 2 | 6 | A | 1 | 50 |
| | | | I | 2 | 51 |
| | | | T | 3 | 52 |
| | | | W | 4 | 53 |
| | | | N | 5 | 54 |
| | | | S | 6 | 55 |
| | | | G | 7 | 56 |
| | | | H | 8 | 57 |
| | | | I | 9 | 58 |
| | | | D | 10 | 59 |
| | | | Y | 11 | 60 |
| | | | A | 12 | 61 |
| | | | D | 13 | 62 |
| | | | S | 14 | 63 |
| | | | V | 15 | 64 |
| | | | E | 16 | 65 |
| | | | G | 17 | 66 |
| Heavy | 3 | 7 | V | 1 | 99 |
| | | | S | 2 | 100 |
| | | | Y | 3 | 101 |
| | | | L | 4 | 102 |
| | | | S | 5 | 103 |
| | | | T | 6 | 104 |
| | | | A | 7 | 105 |
| | | | S | 8 | 106 |
| | | | S | 9 | 107 |
| | | | L | 10 | 108 |
| | | | D | 11 | 109 |
| | | | Y | 12 | 110 |

FIG. 26C

| Antibody Chain | CDR No. | SEQ ID NO. | Residue | Position in CDR | Kabat No. |
|---|---|---|---|---|---|
| Light | 1 | 8 | R | 1 | 24 |
| | | | A | 2 | 25 |
| | | | S | 3 | 26 |
| | | | Q | 4 | 27 |
| | | | G | 5 | 28 |
| | | | I | 6 | 29 |
| | | | R | 7 | 30 |
| | | | N | 8 | 31 |
| | | | Y | 9 | 32 |
| | | | L | 10 | 33 |
| | | | A | 11 | 34 |
| Light | 2 | 9 | A | 1 | 50 |
| | | | A | 2 | 51 |
| | | | S | 3 | 52 |
| | | | T | 4 | 53 |
| | | | L | 5 | 54 |
| | | | Q | 6 | 55 |
| Light | 3 | 10 | Q | 1 | 89 |
| | | | R | 2 | 90 |
| | | | Y | 3 | 91 |
| | | | N | 4 | 92 |
| | | | R | 5 | 93 |
| | | | A | 6 | 94 |
| | | | P | 7 | 95 |
| | | | Y | 8 | 96 |
| | | | T | 9 | 97 |

FIG. 26D

```
GAGGTGCAGC TGGTGGAGTC TGGGGGAGGC TTGGTACAGC CCGGCAGGTC CCTGAGACTC      60

TCCTGTGCGG CCTCTGGATT CACCTTTGAT GATTATGCCA TGCACTGGGT CCGGCAAGCT     120

CCAGGGAAGG GCCTGGAATG GGTCTCAGCT ATCACTTGGA ATAGTGGTCA CATAGACTAT     180

GCGGACTCTG TGGAGGGCCG ATTCACCATC TCCAGAGACA ACGCCAAGAA CTCCCTGTAT     240

CTGCAAATGA ACAGTCTGAG AGCTGAGGAT ACGGCCGTAT ATTACTGTGC GAAAGTCTCG     300

TACCTTAGCA CCGCGTCCTC CCTTGACTAT TGGGGCCAAG GTACCCTGGT CACCGTCTCG     360

AGT                                                                  363
```
Nucleotide Sequence of D2E7 Heavy Chain (SEQ ID NO:1)

```
GACATCCAGA TGACCCAGTC TCCATCCTCC CTGTCTGCAT CTGTAGGGGA CAGAGTCACC      60

ATCACTTGTC GGGCAAGTCA GGGCATCAGA AATTACTTAG CCTGGTATCA GCAAAAACCA     120

GGGAAAGCCC CTAAGCTCCT GATCTATGCT GCATCCACTT TGCAATCAGG GGTCCCATCT     180

CGGTTCAGTG GCAGTGGATC TGGGACAGAT TTCACTCTCA CCATCAGCAG CCTACAGCCT     240

GAAGATGTTG CAACTTATTA CTGTCAAAGG TATAACCGTG CACCGTATAC TTTTGGCCAG     300

GGGACCAAGG TGGAAATCAA A                                              321
```
Nucleotide Sequence of D2E7 Light Chain (SEQ ID NO:3)

FIG. 26E

ANTI-TNF-ALPHA ANTIBODIES AND THEIR USES

1. CROSS-REFERENCE TO RELATED APPLICATIONS

This application is a divisional of U.S. application Ser. No. 12/761,745, filed on Apr. 16, 2010, issued as U.S. Pat. No. 8,722,860 on May 13, 2014, which claims the benefit under 35 U.S.C. §119(e) of U.S. provisional application No. 61/170,053, filed Apr. 16, 2009, the contents of which are incorporated herein by reference in their entirety.

2. REFERENCE TO SEQUENCE LISTING

The Sequence Listing concurrently submitted herewith under 37 CFR §1.821 in a computer readable form (CRF) via EFS-Web as file name 381493US.txt is incorporated herein by reference. The electronic copy of the Sequence Listing was created on Apr. 14, 2010, with a file size of 109,937 bytes.

3. FIELD OF THE INVENTION

The present invention relates to anti-TNF-α antibodies, pharmaceutical compositions comprising anti-TNF-α antibodies, and therapeutic uses of such antibodies.

4. BACKGROUND

Tumor necrosis factor alpha (TNF-α) is a pro-inflammatory cytokine that is released by and interacts with cells of the immune system. TNF-α has been shown to be upregulated in a number of human diseases, including chronic diseases such as rheumatoid arthritis, Crohn's disease, ulcerative colitis and multiple sclerosis. For example, elevated levels of TNF-α are found in the synovial fluid of rheumatoid arthritis patients and play an important role in both the pathologic inflammation and the joint destruction that are hallmarks of rheumatoid arthritis.

Human TNF-α is a 17 kDa protein, and the active form exists as a homotrimer (Pennica et al., 1984, Nature 312:724-729; Davis et al., 1987, Biochemistry 26:1322-1326; Jones et al., 1989, Nature 338:225-228). TNF-α exerts its biological effects through interaction with two structurally related but functionally distinct cell surface receptors, p55 and p75, that are co-expressed on most cell types (Loetscher et al., 1990, Cell 61:351-9; Smith et al., 1990, Science 248(4958):1019-23). p55 is also known as p55R; p55TNFR; CD120a; TNFR I; TNFR 1 and TNFRSFIa. p75 is also known as p75R; p75TNFR; CD120b; TNFR II; TNFR 2 and TNFRSFIb. Both receptors are also proteolytically released as soluble molecules capable of binding TNF-α.

Inhibition of TNF-α activity as a method of treating disease, in particular, rheumatoid arthritis, has been achieved by a number of different means using inhibitors such as antibodies and soluble receptors. Examples include etanercept, marketed by Immunex Corporation as ENBREL® which is a recombinant fusion protein comprising two p75 soluble TNF-receptor domains linked to the Fc portion of a human immunoglobulin. Infliximab, marketed by Centocor Corporation as REMICADE®, is a chimeric antibody having murine anti-TNF-α variable domains and human IgG$_1$ constant domains. Other inhibitors include engineered TNF-α molecules which form trimers with native TNF-α and prevent receptor binding (Steed et al., 2003, Science 301:1895-1898; WO 03/033720; WO 01/64889). These current methods of inhibiting TNF-α activity block binding of TNF-α to both the p55 and p75 receptors (See, for example, Mease, 2005, Expert Opin. Biol. Therapy 5(11):1491-1504). Adalimumab, marketed by Abbott Laboratories as HUMIRA®, is a recombinant, fully human anti-TNF-α antibody (Tussirot and Wendling, 2004, Expert Opin. Pharmacother. 5:581-594). Adalimumab binds specifically to TNF-α and blocks its interaction with the p55 and p75 cell surface TNF-α receptors. Adalimumab also lyses surface TNF-α expressing cells in vitro via complement-dependent cytotoxicity ("CDC") and antibody-dependent cell-mediated cytotoxicity ("ADCC"). Adalimumab does not bind or inactivate lymphotoxin (TNF-β). Adalimumab also modulates biological responses that are induced or regulated by TNF, including changes in the levels of adhesion molecules responsible for leukocyte migration (ELAM-1, VCAM-1, and ICAM-1 with an IC$_{50}$ of 1-2×10$^{-10}$ M).

Despite being a human antibody, Adalimumab can elicit an immune response when administered to humans. Such an immune response can result in an immune complex-mediated clearance of the antibodies or fragments from the circulation and make repeated administration unsuitable for therapy, thereby reducing the therapeutic benefit to the patient and limiting the readministration of the antibody.

Accordingly, there is a need to provide improved anti-TNF-α antibodies or fragments that overcome one more of these problems, for example, by generating variants with higher affinity than Adalimumab that can be administered at reduced dosages or variants with reduced immunogenicity as compared to Adalimumab.

Citation or identification of any reference in Section 4 or in any other section of this application shall not be construed as an admission that such reference is available as prior art to the present disclosure.

5. SUMMARY

The present disclosure relates to variants of the anti-TNF-α antibody D2E7 with improved binding to TNF-α and/or reduced immunogenicity as compared to D2E7. D2E7 has three heavy chain CDRs, referred to herein (in amino- to carboxy-terminal order) as CDR-H1 (SEQ ID NO:5), CDR-H2 (SEQ ID NO:6), and CDR-H3 (SEQ ID NO:7), and three light chain CDRs, referred to herein (in amino- to carboxy-terminal order) as CDR-L1 (SEQ ID NO:8), CDR-L2 (SEQ ID NO:9), and CDR-L3 (SEQ ID NO:10). The anti-TNF-α antibodies and anti-TNF-α binding fragments of the disclosure generally have at least one amino acid substitution in at least one CDR as compared to D2E7.

In certain aspects, at least one amino acid substitution or combination of substitutions is selected from Table 11, Table 12 and/or Table 25. Further mutations (including substitutions, deletions or insertions) can be selected from one or more of Tables 13-25.

In certain aspects, the present disclosure relates to variants of the anti-TNF-α antibody D2E7 with improved binding properties, e.g., improved affinity, to TNF-α as compared to D2E7. In specific embodiments, the antibodies of the disclosure have a greater affinity than D2E7 towards TNF-α, for example improved K$_D$ as measured by BIAcore and/or improved affinity as measured by competition ELISA.

In certain aspects, the anti-TNF-α antibodies and anti-TNF-α binding fragments include at least one substitution selected from S3K in CDR-L2 (SEQ ID NO:9), S3R in CDR-L2 (SEQ ID NO:9), S3N in CDR-L2 (SEQ ID NO:9), T4H in CDR-L2 (SEQ ID NO:9), T4Q in CDR-L2 (SEQ ID NO:9), T4V in CDR-L2 (SEQ ID NO:9), T4F in CDR-L2 (SEQ ID NO:9), T4W in CDR-L2 (SEQ ID NO:9), T4Y in CDR-L2 (SEQ ID NO:9); L5R in CDR-L2 (SEQ ID NO:9), L5K in CDR-L2 (SEQ ID NO:9), Q6K in CDR-L2 (SEQ ID NO:9), Q6R in CDR-L2 (SEQ ID NO:9), D1G in CDR-H1 (SEQ ID NO:5), Y2H in CDR-H1 (SEQ ID NO:5); A3G in CDR-H1 (SEQ ID NO:5), and T3N in CDR-H2 (SEQ ID NO:6). Additional mutations that can be incorporated into the improved affinity variant anti-TNF-α antibodies and anti-TNF-α binding fragments can be deimmunizing substitutions, such as those described in Table 11, as well as other mutations, e.g., substitutions, that do not destroy the ability of the anti-TNF-α antibodies and anti-TNF-α binding fragments to bind TNF-α, including but not limited to the known mutations described in Tables 13 to 24 or the mutations described in Table 25.

In certain aspects, the anti-TNF-α antibodies and anti-TNF-α binding fragments include at least one substitution selected from T4F in CDR-L2, T4W in CDR-L2, T4Y in CDR-L2, L5R in CDR-L2, L5K in CDR-L2, Q6R in CDR-L2, Y2H in CDR-H1, A3G in CDR-H1, and T3N in CDR-H2. Additional mutations or combinations of mutations that can be incorporated into such anti-TNF-α antibodies and anti-TNF-α binding fragments can be selected from one or more of Tables 11 and 13 to 25.

In certain other aspects, the anti-TNF-α antibodies and anti-TNF-α binding fragments include at least one substitution selected from T4F in CDR-L2, T4W in CDR-L2, T4Y in CDR-L2, L5R in CDR-L2, L5K in CDR-L2, Q6R in CDR-L2, Y2H in CDR-H1, A3G in CDR-H1, and T3N in CDR-H2. Additional mutations or combinations of mutations that can be incorporated into such anti-TNF-α antibodies and anti-TNF-α binding fragments can be selected from one or more of Tables 11 and 13 to 18.

In yet other aspects, the anti-TNF-α antibodies and anti-TNF-α binding fragments include the substitutions G5S+A11S or G5S+A11G in CDR-L1. Additional mutations or combinations of mutations that can be incorporated into such anti-TNF-α antibodies and anti-TNF-α binding fragments can be selected from one or more of Tables 11 to 25.

In certain aspects, the anti-TNF-α antibodies and anti-TNF-α binding fragments include the substitutions selected from S3N in CDR-L2, T4V in CDR-L2, Q6K in CDR-L2, and D1G in CDR-H1 in combination with at least one substitution selected from Tables 11, 12, and 25. Additional mutations or combinations of mutations that can be incorporated into such anti-TNF-α antibodies and anti-TNF-α binding fragments can be selected from one or more of Tables 11 to 24.

In certain aspects, the anti-TNF-α antibodies and anti-TNF-α binding fragments include the substitutions selected from S3N in CDR-L2, T4V in CDR-L2, Q6K in CDR-L2, and D1G in CDR-H1 in combination with at least one substitution selected from S3K in CDR-L2, S3R in CDR-L2, T4H in CDR-L2, T4Q in CDR-L2, T4F in CDR-L2, T4W in CDR-L2, T4Y in CDR-L2, L5R in CDR-L2, L5K in CDR-L2, Q6R in CDR-L2, Y2H in CDR-H1, A3G in CDR-H1, and T3N in CDR-H2.

In certain aspects, the anti-TNF-α antibodies and anti-TNF-α binding fragments include the combination of substitutions selected from at least one of S3K, T4H, L5R and Q6R; S3K, T4Q, L5R and Q6K; S3K, T4Y and L5K; S3K and T4Y; S3N, T4V, L5R and Q6K; S3N, T4W, L5R and Q6R; S3R, T4F and L5R; S3R, T4F, L5R and Q6R; S3R, T4H and Q6K; S3R, T4W, L5K and Q6R; T4H, L5K and Q6R; T4H, L5K and Q6R; T4W, L5R and Q6R; and T4Y and L5R in CDR-L2, wherein the six CDRs altogether have up to 17 amino acid substitutions as compared to CDR sequences of the antibody D2E7. The anti-TNF-α antibodies or anti-TNF-α binding fragments optionally include one or more additional mutations or combinations of mutations which can be selected from one or more of Tables 11 to 24.

In certain aspects, the anti-TNF-α antibodies and anti-TNF-α binding fragments include one or more substitutions or combinations of substitutions selected from S3K, S3R, S3N, T4F, T4W, T4Y, T4H, T4Q, T4V, L5R, L5K, Q6R, and Q6K in CDR-L2. Additional mutations or combinations of mutations that can be incorporated into such anti-TNF-α antibodies and anti-TNF-α binding fragments can be selected from one or more of Tables 11 to 24.

In other aspects, the present disclosure relates to variants of the anti-TNF-α antibody D2E7 with reduced immunogenicity as compared to D2E7. In certain aspects, the anti-TNF-α antibodies and anti-TNF-α binding fragments include at least one substitution or combination of substitution(s) in CDR-L1 (SEQ ID NO:8) selected from R7Q; A11S; R7Q+A11S; N8T; N8T+A11S; 16T; A11G; 16T+A11G; Q4G; Q4G+A11S; Q4G+A11G; Q4H; Q4H+A11S; Q4R; Q4R+A11S; G5S; G5S+A11S; N8S+A11S; 16T+A11S; and N8T+A11G. Additional mutations that can be incorporated into the anti-TNF-α antibodies and anti-TNF-α binding fragments with reduced antigenicity include substitutions that improve binding properties to TNF-α, such as those described in Table 12 and/or Table 25, as well as other mutations, e.g., substitutions that do not destroy the ability of the anti-TNF-α antibodies and anti-TNF-α binding fragments to bind TNF-α, including but not limited to the known mutations described in Tables 13 to 25.

In certain aspects, the anti-TNF-α antibodies and anti-TNF-α binding fragments of the disclosure have VH and VL sequences having 80% to 99% sequence identity to the VH and VL sequences of D2E7, and include at least one amino acid substitution in at least one CDR as compared to D2E7. In specific embodiments, the percentage sequence identity for the heavy chain and the light chain compared to the VH and VL sequences of D2E7 is each independently selected from at least 80%, at least 85%, at least 90%, or at least 95% sequence identity.

In certain aspects, the anti-TNF-α antibodies and anti-TNF-α binding fragments of the disclosure have up to 17 amino acid substitutions in their CDRs as compared to the CDRs of D2E7. Variant antibodies with 17 amino acid substitutions that maintain their target binding capability have been generated by Bostrom et al., 2009, Science 323:1610-14. The anti-TNF-α antibodies and anti-TNF-α binding fragments of the disclosure can also have up to 16, up to 15, up to 14, up to 13, up to 12, up to 11, up to 10, up to 9, up to 8, up to 7, up to 6, up to 5, or up to 4 amino acid substitutions in their CDRs as compared to CDR sequences of the antibody D2E7.

In specific embodiments, an anti-TNF-α antibody or anti-TNF-α binding fragment of the disclosure has, independently:

up to one, or up to two, or up to three CDR-H1 substitutions as compared to the corresponding CDR of D2E7;

up to one, up to two, up to three, up to four, up to five or up to six CDR-H2 substitutions as compared to the corresponding CDR of D2E7;

up to one, up to two, up to three, up to four, or up to five CDR-H3 substitutions as compared to the corresponding CDR of D2E7;

up to one, up to two, up to three, or up to four CDR-L1 substitutions as compared to the corresponding CDR of D2E7;

up to one, up to two, up to three, or up to four CDR-L2 substitutions as compared to the corresponding CDR of D2E7; and up to one, up to two, up to three, or up to four CDR-L3 substitutions as compared to the corresponding CDR of D2E7.

The present disclosure further provides pharmaceutical compositions comprising modified anti-TNF-α antibodies and anti-TNF-α binding fragments having increased affinity to TNF-α and/or reduced immunogenicity as compared to D2E7.

In certain aspects, an anti-TNF-α antibody or anti-TNF-α binding fragment of the disclosure can be a bispecific antibody or a TNF-α binding fragment of a bispecific antibody. The bispecific antibody can be specific to TNF-α and another pro-inflammatory cytokine (such as, for example, lymphotoxin, interferon-γ, or interleukin-1).

Nucleic acids comprising nucleotide sequences encoding the anti-TNF-α antibodies and anti-TNF-α binding fragments of the disclosure are provided herein, as are vectors comprising nucleic acids. Additionally, prokaryotic and eukaryotic host cells transformed with a vector comprising a nucleotide sequence encoding an anti-TNF-α antibody or anti-TNF-α binding fragment are provided herein, as well as eukaryotic (such as mammalian) host cells engineered to express the nucleotide sequences. Methods of producing anti-TNF-α antibodies and anti-TNF-α binding fragments by culturing host cells are also provided.

The anti-TNF-α antibodies and anti-TNF-α binding fragments of the disclosure are useful in the treatment of immune disorders, e.g., systemic lupus erythematosus, rheumatoid arthritis, thyroidosis, graft versus host disease, scleroderma, diabetes mellitus, Grave's disease, sarcoidosis, chronic inflammatory bowel disease, ulcerative colitis, or Crohn's disease.

It should be noted that the indefinite articles "a" and "an" and the definite article "the" are used in the present application, as is common in patent applications, to mean one or more unless the context clearly dictates otherwise. Further, the term "or" is used in the present application, as is common in patent applications, to mean the disjunctive "or" or the conjunctive "and."

All publications mentioned in this specification are herein incorporated by reference. Any discussion of documents, acts, materials, devices, articles or the like that has been included in this specification is solely for the purpose of providing a context for the present disclosure. It is not to be taken as an admission that any or all of these matters form part of the prior art base or were common general knowledge in the field relevant to the present disclosure as it existed anywhere before the priority date of this application.

The features and advantages of the disclosure will become further apparent from the following detailed description of embodiments thereof.

6. BRIEF DESCRIPTION OF THE TABLES AND FIGURES

FIG. 1 shows D2E7 VH peptides and D2E7 VL peptides, respectively, that were tested for immunogenicity.

FIG. 2 shows identified CD4+ T cell epitope regions in D2E7. CDR regions are underlined.

FIG. 3 shows HLA class II associations and relative risk of response to the D2E7 VL region peptide epitopes.

Figure 27:
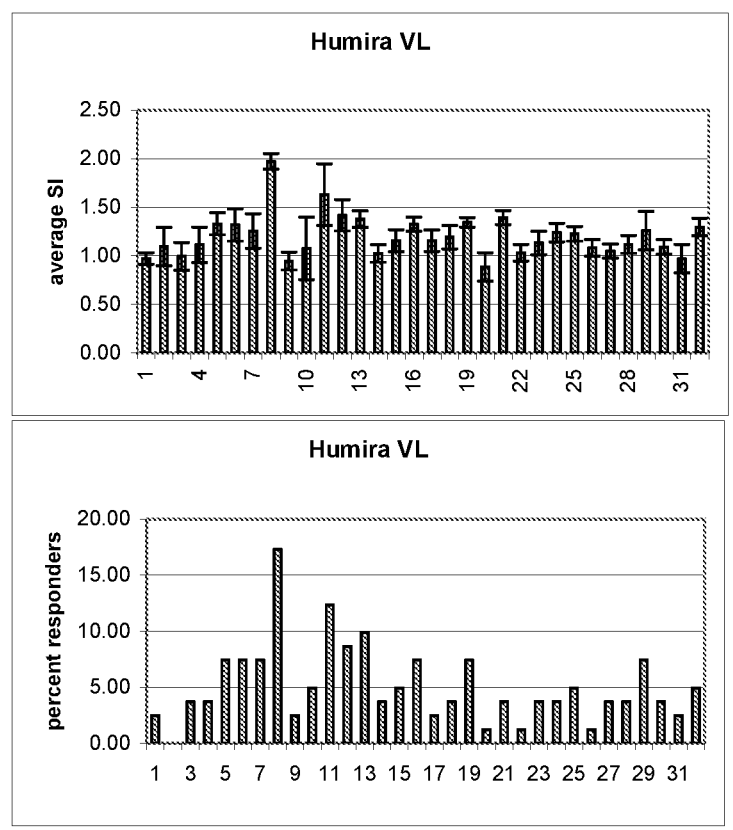

FIG. 4 shows sequences of D2E7 VL CDR1 epitope variants. A total of 99 donors were tested. The number of responders, the percent of responders, and the average stimulation index is indicated for each peptide tested.

FIG. 5 shows candidate mutations in CDR-L1 for lowering immunogenicity of D2E7. The numbering of the amino acids in Table 5 corresponds to the positions in the context of the D2E7 light chain.

FIG. 6 shows BIAcore and ELISA results for substitutions in CDR-L1 that do not result in significantly decreased binding as compared to D2E7. The numbering of the amino acids in FIG. 6 corresponds to the positions in the context of the D2E7 light chain. Improvement in $K_D$ (as measured by BIAcore) and $IC_{50}$ of binding (as measured by ELISA) are indicated by "WTx". CV % refers to the standard deviation as a percentage of the total value measure.

FIG. 7 shows T-cell assay results for all single and double mutations to the D2E7 epitope. Peptide 1 is the parent peptide. Modifications to the parent peptide are in bold-faced type.

FIG. 8 shows the preferred epitope peptide variants based solely on T cell assay results. The numbering of the amino acids in FIG. 8 corresponds to the positions in the context of the D2E7 light chain.

FIG. 9 shows anti-proliferation bioactivity of antibodies constructed to contain the preferred variant epitope peptides. The parent is unmodified D2E7 antibody. The numbering of the amino acids in FIG. 9 corresponds to the positions in the context of the D2E7 light chain.

FIG. 10 shows binding kinetics of D2E7 and the D2E7 variants against TNF-α as analyzed by BIAcore. The numbering of the amino acids in FIG. 10 corresponds to the positions in the context of the D2E7 light chain.

FIG. 11 shows CDR-L1 substitutions or combinations of substitutions that can be incorporated into D2E7-related antibodies to reduce their immunogenicity.

FIG. 12 shows CDR amino acid substitutions outside CDR-L1 resulting in improved $K_D$ (as analyzed by BIAcore), affinity (as measured by ELISA), or both as compared to D2E7. The numbering of the amino acids in FIG. 12 corresponds to the positions in the context of the D2E7 light and heavy chains. Improvement in $K_D$ (as measured by BIAcore) and $IC_{50}$ of binding (as measured by ELISA) are indicated by "WTx". CV % refers to the standard deviation as a percentage of the total value measure and "ND" means "not done".

FIG. 13 shows known mutations in CDR-H1 that can be incorporated into the antibodies of the disclosure.

FIG. 14 shows known mutations in CDR-H2 that can be incorporated into the antibodies of the disclosure. The inclusion of 2 amino acids into a single cell indicates a CDR variant that incorporates an addition to or insertion into the CDR. Shading of a cell indicates a CDR variant that lacks the shaded amino acid residues.

FIG. 15 shows known mutations in CDR-H3 that can be incorporated into the antibodies of the disclosure.

FIG. 16 shows known mutations in CDR-L1 that can be incorporated into the antibodies of the disclosure. The inclusion of 2 amino acids into a single cell indicates a CDR variant that incorporates an addition to or insertion into the CDR.

FIG. 17 shows known mutations in CDR-L2 that can be incorporated into the antibodies of the disclosure. The inclusion of 2 amino acids into a single cell indicates a CDR variant that incorporates the indicated additional N-terminal amino acid into the CDR.

FIG. 18 shows known mutations in CDR-L3 that can be incorporated into the antibodies of the disclosure. The inclusion of 2 amino acids into a single cell indicates a CDR variant that incorporates the indicated additional N-terminal amino acid into the CDR.

FIG. 19 shows further known mutations in CDR-H1 that can be incorporated into the antibodies of the disclosure.

FIG. 20 shows further known mutations in CDR-H2 that can be incorporated into the antibodies of the disclosure.

FIG. 21 shows further known mutations in CDR-H3 that can be incorporated into the antibodies of the disclosure.

FIG. 22 shows further known mutations in CDR-L1 that can be incorporated into the antibodies of the disclosure.

FIG. 23 shows further known mutations in CDR-L2 that can be incorporated into the antibodies of the disclosure.

FIG. 24 shows further known mutations in CDR-L3 that can be incorporated into the antibodies of the disclosure.

FIG. 25 shows combinations of point mutations in CDR-L2 resulting in improved $K_D$ (as analyzed by BIAcore), affinity (as measured by ELISA), or both as compared to D2E7. The point mutations can be incorporated singly or in combination into the antibodies of the disclosure.

FIGS. 26A-26E. FIG. 26A shows the amino acid sequences of the D2E7 heavy and light chains, with CDR regions in bold, underlined text. FIG. 26B shows the CDR sequences and corresponding sequence identifiers of D2E7. FIG. 26C shows a correspondence chart between the heavy chain CDR numbering and the heavy chain Kabat numbering. FIG. 26D shows a correspondence chart between the light chain CDR numbering and the light chain Kabat numbering. FIG. 26E shows the nucleotide sequences of the heavy and light chain variable regions of D2E7 (SEQ ID NO:1 and SEQ ID NO:3, respectively) as published in U.S. Pat. No. 6,090,382.

FIG. 27 shows percent responses (bottom) and average stimulation indexes (top) to the D2E7 VL peptides.

Figure 28:
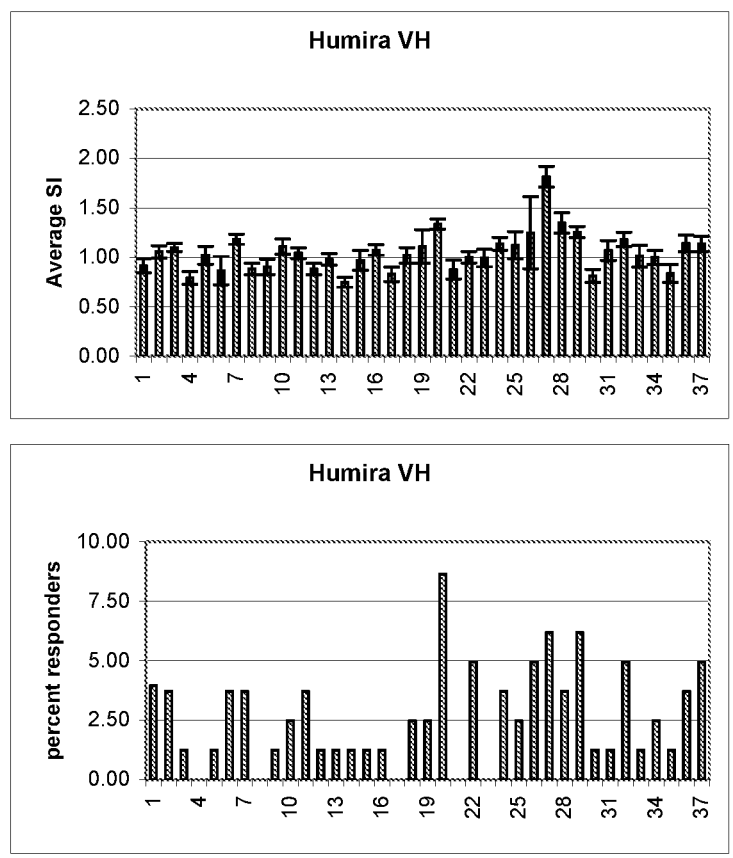

FIG. 28 shows average stimulation indexes (top) and percent responses (bottom) to the D2E7 VH peptides. Peptide #27 had an anomalous stimulation index in one donor, and is indicated in darker shading.

Figure 29:
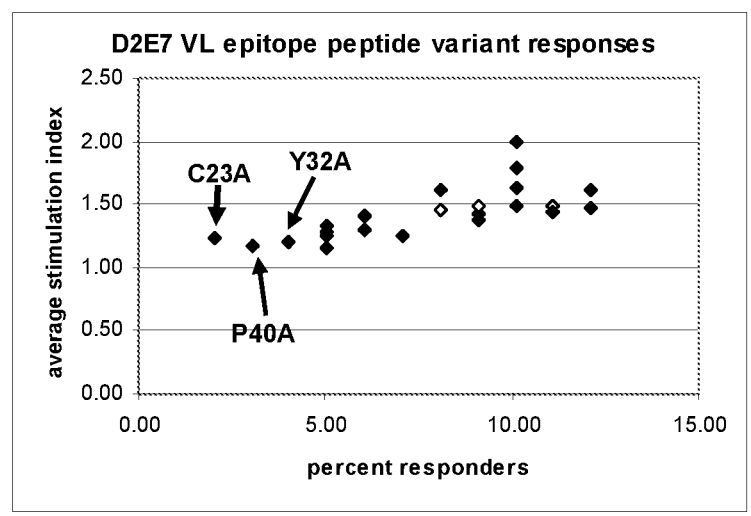

FIG. 29 shows D2E7 VL CDR1 epitope peptide variants. Open symbols indicate multiple retests of the unmodified parent peptide within the dataset. Filled symbols represent unique peptide alanine scan variants. The sequence of the most reduced response-inducing variants is indicated.

Figure 30:
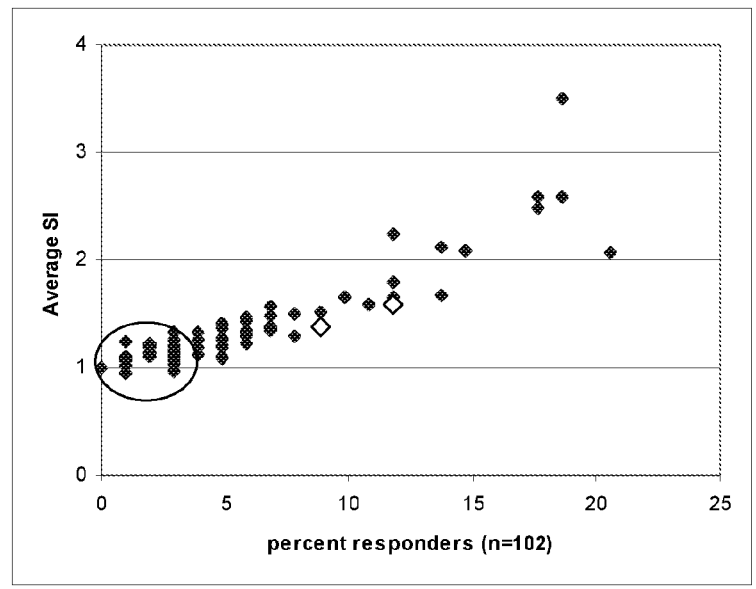

FIG. 30 shows D2E7 VL CDR1 epitope peptide variants. Open symbols indicate multiple retests of the unmodified parent peptide within the dataset. Filled symbols represent unique peptide variants. The most reduced response-inducing variants are indicated by a circle. This figure graphically represents data from FIG. 7.

Figure 31:
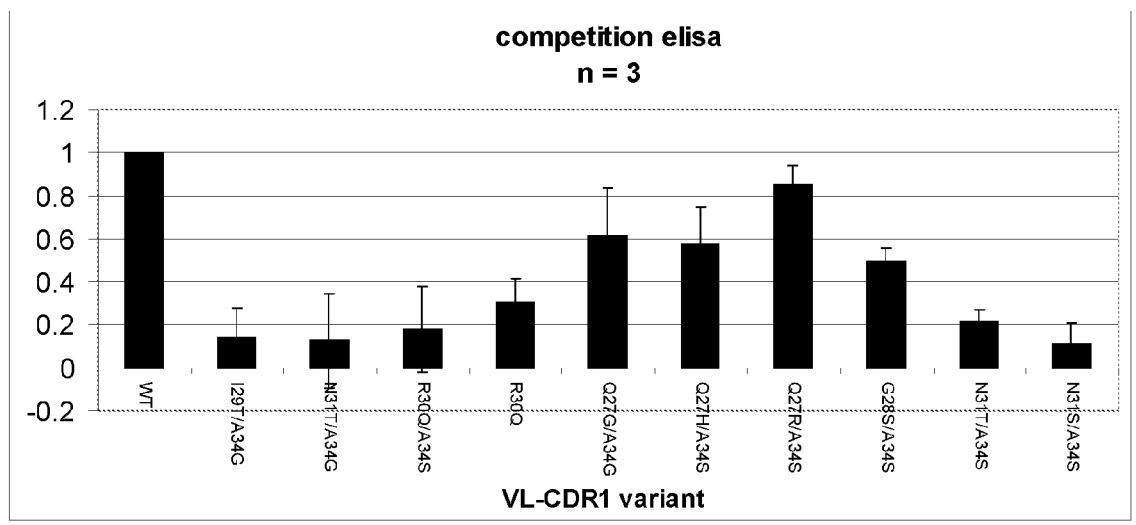

FIG. 31 shows the results of competition ELISA of D2E7 variant antibodies. ELISA plates were coated with TNF-α. Biotinylated D2E7 was included in all wells at a single concentration, and the variant antibody was titrated in. The $IC_{50}$ values were calculated for each antibody. The experiment was performed three times. The Y axis shows average results as a percent of the parent antibody binding.

7. DETAILED DESCRIPTION

7.1 Anti-TNF-α Antibodies

The present disclosure provides anti-TNF-α antibodies. Unless indicated otherwise, the term "antibody" (Ab) refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), and antigen binding fragments of antibodies, including, e.g., Fab', F(ab')₂, Fab, Fv, rIgG, and scFv fragments. Moreover, unless otherwise indicated, the term "monoclonal antibody" (mAb) is meant to include both intact molecules, as well as, antibody fragments (such as, for example, Fab and F(ab')₂ fragments) which are capable of specifically binding to a protein. Fab and F(ab')₂ fragments lack the Fc fragment of intact antibody, clear more rapidly from the circulation of the animal or plant, and may have less non-specific tissue binding than an intact antibody (Wahl et al., 1983, J. Nucl. Med. 24:316).

The term "scFv" refers to a single chain Fv antibody in which the variable domains of the heavy chain and the light chain from a traditional antibody have been joined to form one chain.

References to "VH" refer to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 Daltons, composed of two identical light (L) chains and two identical heavy (H) chains. Each heavy chain has at the amino terminus a variable domain (VH) followed by a number of constant domains. Each light chain has a variable domain at the amino terminus (VL) and a constant domain at the carboxy terminus.

The anti-TNF-α antibodies of the disclosure bind to human TNF-α and inhibit TNF-α receptor activity in a cell. Without being bound by any one theory, the inventors believe that the antibodies reduce the binding of TNF-α to both the low affinity TNF-α receptor (p75) and the high affinity TNF-α receptor (p55).

The anti-TNF-α antibodies of the disclosure contain complementarity determining regions (CDRs) that are related in sequence to the CDRs of the antibody D2E7 (also known as Adalimumab or HUMIRA®).

CDRs are also known as hypervariable regions both in the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting (and in some cases forming part of) the β-sheet structure. The CDRs in each chain are held together in close proximity by the FR regions in the order FR1-CDR1-FR2-CDR2-FR3-CDR3-FR4 and with the CDRs from the other chain, contribute to the formation of the target binding site of antibodies (See Kabat et al., Sequences of Proteins of Immunological Interest (National Institute of Health, Bethesda, Md. 1987)). As used herein, numbering of immunoglobulin amino acid residues is done according to the immunoglobulin amino acid residue numbering system of Kabat et al. unless otherwise indicated.

The sequences of the heavy and light chain variable regions of D2E7 are represented by SEQ ID NO:2 and SEQ ID NO:4, respectively, and encoded by SEQ ID NO.: 1 and SEQ ID NO.: 3, respectively. The sequences of the heavy and light chain variable regions are also depicted in FIG. 1A. The sequences of the CDRs of D2E7, and their corresponding identifiers, are presented in FIG. 1B. The sequences of the heavy and light chain variable regions of D2E7 (as published in U.S. Pat. No. 6,090,382) are shown in FIG. 1C. Any nucleotide sequences encoding SEQ ID NO:2 or SEQ ID NO:4 can be used in the compositions and methods of the present disclosure.

The present disclosure further provides anti-TNF-α antibody fragments comprising CDR sequences that are related to the CDR sequences of D2E7. The term "antibody fragment" refers to a portion of a full-length antibody, generally the target binding or variable region. Examples of antibody fragments include Fab, Fab', F(ab')2 and Fv fragments. An "Fv" fragment is the minimum antibody fragment which contains a complete target recognition and binding site. This region consists of a dimer of one heavy and one light chain variable domain in a tight, noncovalent association (VH-VL dimer). It is in this configuration that the three CDRs of each variable domain interact to define a target binding site on the surface of the VH-VL dimer. Often, the six CDRs confer target binding specificity to the antibody. However, in some instances even a single variable domain (or half of an Fv comprising only three CDRs specific for a target) can have the ability to recognize and bind target. "Single chain Fv" or "scFv" antibody fragments comprise the VH and VL domains of an antibody in a single polypeptide chain. Generally, the Fv polypeptide further comprises a polypeptide linker between the VH and VL domain that enables the scFv to form the desired structure for target binding. "Single domain antibodies" are composed of a single VH or VL domains which exhibit sufficient affinity to the TNF-α. In a specific embodiment, the single domain antibody is a camelid antibody (see, e.g., Riechmann, 1999, Journal of Immunological Methods 231:25-38).

The Fab fragment contains the constant domain of the light chain and the first constant domain ($CH_1$) of the heavy chain. Fab' fragments differ from Fab fragments by the addition of a few residues at the carboxyl terminus of the heavy chain $CH_1$ domain including one or more cysteines from the antibody hinge region. F(ab') fragments are produced by cleavage of the disulfide bond at the hinge cysteines of the $F(ab')_2$ pepsin digestion product. Additional chemical couplings of antibody fragments are known to those of ordinary skill in the art.

In certain embodiments, the anti-TNF-α antibodies of the disclosure are monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone and not the method by which it is produced. Monoclonal antibodies useful in connection with the present disclosure can be prepared using a wide variety of techniques known in the art including the use of hybridoma, recombinant, and phage display technologies or a combination thereof. The anti-TNF-α antibodies of the disclosure include chimeric, primatized, humanized, or human antibodies.

The anti-TNF-α antibodies of the disclosure can be chimeric antibodies. The term "chimeric" antibody as used herein refers to an antibody having variable sequences derived from a non-human immunoglobulin, such as rat or mouse antibody, and human immunoglobulin constant regions, typically chosen from a human immunoglobulin template. Methods for producing chimeric antibodies are known in the art. See, e.g., Morrison, 1985, Science 229 (4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397, which are incorporated herein by reference in their entireties.

The anti-TNF-α antibodies of the disclosure can be humanized. "Humanized" forms of non-human (e.g., murine) antibodies are chimeric immunoglobulins, immunoglobulin chains or fragments thereof (such as Fv, Fab, Fab', $F(ab')_2$ or other target-binding subdomains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

The anti-TNF-α antibodies of the disclosure can be human antibodies. Completely "human" anti-TNF-α antibodies can be desirable for therapeutic treatment of human patients. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Medarex (Princeton, N.J.), Astellas Pharma (Deerfield, Ill.), Amgen (Thousand Oaks, Calif.) and Regeneron (Tarrytown, N.Y.) can be engaged to provide human antibodies directed against a selected antigen using technology similar to that described above. Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1988, Biotechnology 12:899-903).

The anti-TNF-α antibodies of the disclosure can be primatized. The term "primatized antibody" refers to an antibody comprising monkey variable regions and human constant regions. Methods for producing primatized antibodies are known in the art. See e.g., U.S. Pat. Nos. 5,658,570; 5,681, 722; and 5,693,780, which are incorporated herein by reference in their entireties.

The anti-TNF-α antibodies of the disclosure can be bispecific antibodies. Bispecific antibodies are monoclonal, often human or humanized, antibodies that have binding specificities for at least two different antigens. In the present disclosure, one of the binding specificities can be directed towards TNF-α, the other can be for any other antigen, e.g., for a cell-surface protein, receptor, receptor subunit, tissue-specific antigen, virally derived protein, virally encoded envelope protein, bacterially derived protein, or bacterial surface protein, etc.

The anti-TNF-α antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein (see Section 7.6 for a discussion of antibody conjugates), etc. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (See, e.g., Wolfson, 2006, Chem. Biol. 13(10):1011-2).

In yet another embodiment of the disclosure, the anti-TNF-α antibodies or fragments thereof can be antibodies or antibody fragments whose sequence has been modified to alter at least one constant region-mediated biological effector function relative to the corresponding wild type sequence. For example, in some embodiments, an anti-TNF-α antibody of the disclosure can be modified to reduce at least one constant region-mediated biological effector function relative to an unmodified antibody, e.g., reduced binding to the Fc receptor (FcγR). FcγR binding can be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC").

In other embodiments of the disclosure, an anti-TNF-α antibody or fragment thereof can be modified to acquire or improve at least one constant region-mediated biological effector function relative to an unmodified antibody, e.g., to enhance FcγR interactions (See, e.g., US 2006/0134709). For example, an anti-TNF-α antibody of the disclosure can have a constant region that binds FcγRIIA, FcγRIIB and/or FcγRIIIA with greater affinity than the corresponding wild type constant region.

Thus, antibodies of the disclosure can have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" (shown in FIG. 4 of U.S. Pat. No. 5,834,597) in which residue 236 is deleted and residues 234, 235 and 237 (using EU numbering) are substituted with alanines.

In some embodiments, the anti-TNF-α antibodies of the disclosure have low levels of or lack fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

In yet another aspect, the anti-TNF-α antibodies or fragments thereof can be antibodies or antibody fragments that have been modified to increase or reduce their binding affinities to the fetal Fc receptor, FcRn, for example, by mutating the immunoglobulin constant region segment at particular regions involved in FcRn interactions (See, e.g., WO 2005/123780). In particular embodiments, an anti-TNF-α antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in Table 1 of U.S. Pat. No. 7,217,797, which table is incorporated by reference herein in its entirety. Such mutations increase the antibody's binding to FcRn, which protects the antibody from degradation and increases its half-life.

In yet other aspects, an anti-TNF-α antibody has one or more amino acids inserted into one or more of its hypervariable regions, for example as described in Jung and Plückthun, 1997, Protein Engineering 10:9, 959-966; Yazaki et al., 2004, Protein Eng. Des Sel. 17(5):481-9. Epub 2004 Aug. 17; and U.S. Pat. App. No. 2007/0280931.

7.2 Nucleic Acids and Expression Systems

The present disclosure encompasses nucleic acid molecules and host cells encoding the anti-TNF-α antibodies of the disclosure.

An anti-TNF-α antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

In one embodiment, the anti-TNF-α antibodies are similar to D2E7 but for changes in one or more CDRs (referred to hereinbelow as having "D2E7-related" sequences). In another embodiment, the anti-TNF-α antibodies are similar to D2E7 but for changes in one or more framework regions. In yet another embodiment, the anti-TNF-α antibodies are similar to D2E7 but for changes in one or more CDRs and in one or more framework regions. To generate nucleic acids encoding such anti-TNF-α antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (See, e.g., the "VBASE" human germline sequence database; see also Kabat, E. A. et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference). A DNA fragment encoding the heavy or light chain variable region of D2E7, the sequences of which are shown in FIG. 1C, can be synthesized and used as a template for mutagenesis to generate a variant as described herein using routine mutagenesis techniques; alternatively, a DNA fragment encoding the variant can be directly synthesized.

Once DNA fragments encoding D2E7 or D2E7-related VH and VL segments are obtained, these DNA fragments can be further manipulated by standard recombinant DNA techniques, for example, to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions ($CH_1$, $CH_2$, $CH_3$ and optionally $CH_4$). The sequences of human heavy chain constant region genes are known in the art (See, e.g., Kabat, E. A. et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$ constant region. For a Fab fragment heavy chain gene, the VH-encoding DNA can be operatively linked to another DNA molecule encoding only the heavy chain $CH_1$ constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (See, e.g., Kabat, E. A. et al., 1991, Sequences of Proteins of Immunological Interest, Fifth Edition (U.S. Department of Health and Human Services, NIH Publication No. 91-3242)) and DNA fragments encompassing these regions can be obtained by standard PCR amplification. The light chain constant region can be a kappa or lambda constant region, but in certain embodiments is a kappa constant region. To create a scFv gene, the VH- and VL-encoding DNA fragments are operatively linked to another fragment encoding a flexible linker, e.g., encoding the amino acid sequence $(Gly_4\text{~}Ser)_3$, such that the VH and VL sequences can be expressed as a contiguous single-chain protein, with the VL and VH regions joined by the flexible linker (See, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-TNF-α antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector can already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (See, e.g., U.S. Pat. Nos. 4,399, 216, 4,634,665 and 5,179,017, all by Axel et al.). For example, typically the selectable marker gene confers resistance to drugs, such as G418, puromycin, blasticidin, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies of the disclosure in either prokaryotic or eukaryotic host cells. In certain embodiments, expression of antibodies is performed in eukaryotic cells, e.g., mammalian host cells, for optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NS0 myeloma cells, COS cells, 293 cells and SP2/0 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-TNF-α antibody of this disclosure.

Recombinant DNA technology can also be used to remove some or all of the DNA encoding either or both of the light and heavy chains that is not necessary for binding to TNF-α. The molecules expressed from such truncated DNA molecules are also encompassed by the antibodies of the disclosure.

In addition, bifunctional antibodies can be produced in which one heavy and one light chain are an antibody of the disclosure and the other heavy and light chain are specific for an antigen other than TNF-α by crosslinking an antibody of the disclosure to a second antibody by standard chemical crosslinking methods. Bifunctional antibodies can also be made by expressing a nucleic acid engineered to encode a bifunctional antibody.

In certain embodiments, dual specific antibodies, i.e. antibodies that bind TNF-α and an unrelated antigen using the same binding site, can be produced by mutating amino acid residues in the light chain and/or heavy chain CDRs. In various embodiments, dual specific antibodies that bind TNF-α and another antigen, for example, another proinflammatory cytokine (such as, for example, lymphotoxin, interferon-γ, or interleukin-1) can be produced by mutating amino acid residues in the periphery of the antigen binding site (See, e.g., Bostrom et al., 2009, Science 323:1610-1614). Dual functional antibodies can be made by expressing a nucleic acid engineered to encode a dual specific antibody.

For recombinant expression of an anti-TNF-α antibody of the disclosure, the host cell can be co-transfected with two expression vectors of the disclosure, the first vector encoding a heavy chain derived polypeptide and the second vector encoding a light chain derived polypeptide. Typically, the two vectors each contain a separate selectable marker. Alternatively, a single vector can be used which encodes both heavy and light chain polypeptides.

Once a nucleic acid encoding one or more portions of D2E7 or of an anti-TNF-α antibody with CDR sequences related to the CDR sequences of D2E7 is generated, further alterations or mutations can be introduced into the coding sequence, for example to generate nucleic acids encoding antibodies with different CDR sequences, antibodies with reduced affinity to the Fc receptor, or antibodies of different subclasses.

The anti-TNF-α antibodies of the disclosure can also be produced by chemical synthesis (e.g., by the methods described in Solid Phase Peptide Synthesis, 2$^{nd}$ ed., 1984 The Pierce Chemical Co., Rockford, Ill.). Variant antibodies can also be generated using a cell-free platform (see, e.g., Chu et al., Biochemia No. 2, 2001 (Roche Molecular Biologicals)).

Once an anti-TNF-α antibody of the disclosure has been produced by recombinant expression, it can be purified by any method known in the art for purification of an immunoglobulin molecule, for example, by chromatography (e.g., ion exchange, affinity, particularly by affinity for TNF-α after Protein A or Protein G selection, and sizing column chromatography), centrifugation, differential solubility, or by any other standard technique for the purification of proteins. Further, the anti-TNF-α antibodies of the present disclosure or fragments thereof can be fused to heterologous polypeptide sequences described herein or otherwise known in the art to facilitate purification.

Once isolated, an anti-TNF-α antibody can, if desired, be further purified, e.g., by high performance liquid chromatography (See, e.g., Fisher, Laboratory Techniques In Biochemistry And Molecular Biology (Work and Burdon, eds., Elsevier, 1980)), or by gel filtration chromatography on a Superdex™ 75 column (Pharmacia Biotech AB, Uppsala, Sweden).

7.3 Biological Activities of Anti-TNF-α Antibodies

In certain embodiments, the anti-TNF-α antibodies of the disclosure have certain biological activities, such as competing with D2E7 for binding to TNF-α or neutralizing TNF-α activity.

Accordingly, in certain embodiments, anti-TNF-α antibodies of the disclosure compete with D2E7 for binding to TNF-α. The ability to compete for binding to TNF-α can be tested using a competition assay. In one example of a competition assay, TNF-α is adhered onto a solid surface, e.g., a microwell plate, by contacting the plate with a solution of TNF-α (e.g., at a concentration of 1 μg/mL in PBS over night at 4° C.). The plate is washed (e.g., 0.1% Tween 20 in PBS) and blocked (e.g., in Superblock, Thermo Scientific, Rockford, Ill.). A mixture of sub-saturating amount of biotinylated D2E7 (80 ng/mL) and unlabeled D2E7 (the "reference" antibody) or competing anti-TNF-α antibody (the "test" antibody) antibody in serial dilution (e.g., at a concentration of 2.8 μg/mL, 8.3 μg/mL, or 25 μg/mL) in ELISA buffer (e.g., 1% BSA and 0.1% Tween 20 in PBS) is added to wells and plates are incubated for 1 hour with gentle shaking. The plate is washed, 1 μg/mL HRP-conjugated Streptavidin diluted in ELISA buffer was added to each well and the plates incubated for 1 hour. Plates are washed and bound antibodies were detected by addition of substrate (e.g., TMB, Biofx Laboratories Inc., Owings Mills, Md.). The reaction is terminated by addition of stop buffer (e.g., Bio FX Stop Reagents, Biofx Laboratories Inc., Owings Mills, Md.) and the absorbance was measured at 650 nm using microplate reader (e.g., VERSAmax, Molecular Devices, Sunnyvale, Calif.). Variations on this competition assay can also be used to test competition between an anti-TNF-α antibody of the disclosure and D2E7. For example, in certain aspects, the anti-TNF-α antibody is used as a reference antibody and D2E7 is used as a test antibody. Additionally, instead of soluble TNF-α, membrane-bound TNF-α expressed on cell surface (for example mammalian cells such as 293S) in culture can be used. Alternatively, instead of soluble D2E7 and test antibodies, those expressed on cell surface (for example mammalian cells such as 293c18) in culture can be used too. Generally, about $10^4$ to $10^6$ transfectants, e.g., about $10^5$ transfectants, are used. Other formats for competition assays are known in the art and can be employed.

In various embodiments, an anti-TNF-α antibody of the disclosure reduces the binding of labeled D2E7 by at least 40%, by at least 50%, by at least 60%, by at least 70%, by at least 80%, by at least 90%, or by a percentage ranging between any of the foregoing values (e.g., an anti-TNF-α antibody of the disclosure reduces the binding of labeled D2E7 by 50% to 70%) when the anti-TNF-α antibody is used at a concentration of 0.08 μg/mL, 0.4 μg/mL, 2 μg/mL, 10 μg/mL, 50 μg/mL, 100 μg/mL or at a concentration ranging between any of the foregoing values (e.g., at a concentration ranging from 2 μg/mL to 10 μg/mL).

In other embodiments, D2E7 reduces the binding of a labeled anti-TNF-α antibody of the disclosure by at least 40%, by at least 50%, by at least 60%, by at least 70%, by at least 80%, by at least 90%, or by a percentage ranging between any of the foregoing values (e.g., D2E7 reduces the binding of a labeled an anti-TNF-α antibody of the disclosure by 50% to 70%) when D2E7 is used at a concentration of 0.4 μg/mL, 2 μg/mL, 10 μg/mL, 50 μg/mL, 250 μg/mL or at a concentration ranging between any of the foregoing values (e.g., at a concentration ranging from 2 μg/mL to 10 μg/mL).

In other aspects, an anti-TNF-α antibody of the disclosure inhibits TNF-α activity in a range of in vitro assays, such as cell cytotoxicity, mitogenesis, cytokine induction, and induction of adhesion molecules. Alternatively, activity of an anti-TNF-α antibody of the disclosure can be measured by in vitro assays using membrane bound TNF-α naturally or recombinantly expressed on cells, such as ability to induce reverse signaling, cytokine induction, induction of adhesion molecules, CDC and ADCC. An exemplary TNF-α neutralization assay that measures inhibition of soluble TNF-α cytotoxicity using cells sensitive to TNF-α (e.g., L929) is described below. Other TNF-α cytotoxicity assays can also be used to assess the activity of the anti-TNF-α antibodies of the disclosure.

Thus, in an exemplary embodiment, an anti-TNF-α cytotoxicity assays entails plating $3\times10^4$ murine L929 cells into individual wells of a flat bottomed 96-well microtiter plate. The cells are incubated overnight at 37° C. in a humidified 5% $CO_2$ incubator. The next day, serial dilutions of the anti-TNF-α antibody (e.g., 0.712 μg/mL, 0.949 μg/mL, 1.27 μg/mL, 1.69 μg/mL, 2.25 μg/mL or 3 μg/mL) are prepared in 25 μL of serum-free medium and added to cells (e.g. final concentration in 150 μL culture is 119 ng/mL, 158 ng/mL, 211 ng/mL, 282 ng/mL, 375 ng/mL or 500 ng/mL). After a 2-hour incubation at 37° C., 5% $CO_2$, TNF-α is added at final concentration of 40 ng/mL (e.g., 254, of 240 ng/mL) and the cells were further incubated for 48 hours at 37° C., 5% $CO_2$. The wells are scored for cytotoxicity as compared to control plates (which in certain embodiments were treated with TNF-α that were not incubated with an anti-TNF-α antibody, e.g., were incubated with an isotype control antibody and in other embodiments were treated with D2E7) using a viability assay (e.g., CellTiter-Blue, Promega, Madison, Wis.). Other formats for TNF-α neutralization assays are known in the art and can be employed.

In various embodiments, an anti-TNF-α antibody of the disclosure neutralizes TNF-α by at least 30%, by at least 40%, by at least 50%, by at least 60%, by at least 70%, by at least 80%, by at least 90%, or by a percentage ranging between any of the foregoing values (e.g., an anti-TNF-α antibody of the disclosure neutralizes TNF-α activity by 50% to 70%) when the anti-TNF-α antibody is used at a concentration of 2 ng/mL, 5 ng/mL, 10 ng/mL, 20 ng/mL, 0.1 μg/mL, 0.2 μg/mL, 1 μg/mL, 2 μg/mL, 5 μg/mL, 10 μg/mL, 20 μg/mL, or at a concentration ranging between any of the foregoing values (e.g., at a concentration ranging from 1 μg/mL to 5 μg/mL). In some embodiments, an anti-TNF-α antibody of the disclosure is at least 80% as effective, at least 90% as effective, at least 100% as effective, at least 110% as effective, at least 125% as effective or at least 150% as effective, and up to 110% as effective, up to 125% as effective, up to 150% as effective or up to 200% as effective as D2E7 at neutralizing TNF-α, or any range between any pair of the foregoing values (e.g., 80% to 125% as effective as D2E7 or 125% to 200% as effective as D2E7 in neutralizing TNF-α).

In certain embodiments, the anti-TNF-α antibodies of the disclosure have a high binding affinity for TNF-α. In specific embodiments, the anti-TNF-α antibodies of the present disclosure have specific association rate constants ($k_{on}$ or $k_a$ values), dissociation rate constants ($k_{off}$ or $k_d$ values), affinity constants ($K_A$ values), dissociation constants ($K_D$ values) and/or $IC_{50}$ values. In certain aspects, such values are selected from the following embodiments.

7.4 Kinetic Properties of Anti-TNF-α Antibodies

In a specific embodiment, an anti-TNF-α antibody of the disclosure binds to TNF-α with a $k_{on}$ of at least $10^5$ $M^{-1}$ $s^{-1}$, at least $5\times10^5$ $M^{-1}$ $s^{-1}$, at least $10^6$ $M^{-1}$ $s^{-1}$, at least $5\times10^6$ $M^{-1}$ $s^{-1}$, at least $10^7$ $M^{-1}$ $s^{-1}$, at least $5\times10^7$ $M^{-1}$ $s^{-1}$, at least $10^8$ $M^{-1}$ $s^{-1}$, or with a $k_{on}$ of any range between any pair of the foregoing values (e.g., $5\times10^5$ to $5\times10^6$ $M^{-1}$ $s^{-1}$ or $10^7$ to $10^8$ $M^{-1}$ $s^{-1}$).

In another embodiment, an anti-TNF-α antibody of the disclosure binds to TNF-α with a $k_{off}$ rate of $5\times10^{-1}$ $s^{-1}$ or less, $10^{-1}$ $s^{-1}$ or less, $5\times10^{-2}$ $s^{-1}$ or less, $10^{-2}$ $s^{-1}$ or less, $5\times10^{-3}$ $s^{-1}$ or less, $10^{-3}$ s$^{-1}$ or less, $5\times10^{-4}$ s$^{-1}$ or less, $10^{-4}$ s$^{-1}$ or less, $5\times10^{-5}$ s$^{-1}$ or less, $10^{-5}$ s$^{-1}$ or less, $5\times10^{-6}$ s$^{-1}$ or less, $10^{-6}$ s$^{-1}$ or less, $5\times10^{-7}$ s$^{-1}$ or less, $10^{-7}$ s$^{-1}$ or less, $5\times10^{-8}$ s$^{-1}$ or less, $10^{-8}$ s$^{-1}$ or less, $5\times10^{-9}$ s$^{-1}$ or less, $10^{-9}$ s$^{-1}$ or less, $5\times10^{-10}$ s$^{-1}$ or less, $10^{-10}$ s$^{-1}$ or less, or with a $k_{off}$ rate of any range between any pair of the foregoing values (e.g., $5\times10^{-4}$ to $10^{-6}$ s$^{-1}$, or $5\times10^{-5}$ to $5\times10^{-8}$ s$^{-1}$).

In another embodiment, an anti-TNF-α antibody of the disclosure binds to TNF-α with a $K_A$ ($k_{on}/k_{off}$) of at least $10^{11}$ nM$^{-1}$, at least $5\times10^{11}$ nM$^{-1}$, at least $10^{12}$ nM$^{-1}$, at least $5\times10^{12}$ nM$^{-1}$, at least $10^{13}$ nM$^{-1}$, at least $5\times10^{13}$ nM$^{-1}$, at least $10^{14}$ nM$^{-1}$, at least $5\times10^{14}$ nM$^{-1}$, at least $10^{15}$ nM$^{-1}$, at least $5\times10^{15}$ nM$^{-1}$, at least $10^{16}$ nM$^{-1}$, at least $5\times10^{16}$ nM$^{-1}$, at least $10^{17}$ nM$^{-1}$, at least $5\times10^{17}$ nM$^{-1}$, at least $10^{18}$ nM$^{-1}$, at least $5\times10^{18}$ nM$^{-1}$, at least $10^{19}$ nM$^{-1}$, at least $5\times10^{19}$ nM$^{-1}$, at least $10^{20}$ nM$^{-1}$, at least $5\times10^{20}$ nM$^{-1}$, at least $10^{21}$ nM$^{-1}$, at least $5\times10^{21}$ nM$^{-1}$, at least $10^{22}$ nM$^{-1}$, at least $5\times10^{22}$ nM$^{-1}$, at least $10^{23}$ nM$^{-1}$, at least $5\times10^{23}$ nM$^{-1}$, at least $10^{24}$ nM$^{-1}$, at least $5\times10^{24}$ nM$^{-1}$, or with a $K_A$ of any range between any pair of the foregoing values (e.g., $5\times10^{14}$ to $10^{22}$ nM$^{-1}$, or $10^{11}$ to $5\times10^{18}$ nM$^{-1}$).

In other embodiments, an anti-TNF-α antibody of the disclosure binds to TNF-α with a $K_D$ ($k_{off}/k_{on}$) of $5\times10^7$ nM or less, $10^7$ nM or less, $5\times10^6$ nM or less, $10^6$ nM or less, $5\times10^5$ nM or less, $10^5$ nM or less, $5\times10^4$ nM or less, $10^4$ nM or less, $5\times10^3$ nM or less, $10^3$ nM or less, $5\times10^2$ nM or less, 100 nM or less, 90 nM or less, 80 nM or less, 70 nM or less, 60 nM or less, 50 nM or less, 20 nM or less, 15 nM or less, 10 nM or less, 5 nM or less, 3.8 nM or less, 2 nM or less, 1.5 nM or less, 1 nM or less, $5\times10^{-1}$ nM or less, $10^{-1}$ nM or less, $5\times10^{-2}$ nM or less, $10^{-2}$ nM or less, $5\times10^{-3}$ nM or less, $10^{-3}$ nM or less, $5\times10^{-4}$ nM or less, $10^{-4}$ nM or less, $5\times10^{-5}$ nM or less, $10^{-5}$ nM or less, $5\times10^{-6}$ nM or less, $10^{-6}$ nM or less, or with a $K_D$ of any range between any pair of the foregoing values (e.g., $5\times10^7$ to 50 nM, or 15 nM to $5\times10^{-3}$ nM).

In certain specific embodiments, an TNF-α antibody of the disclosure binds to TNF-α with a $K_D$ ($k_{off}/k_{on}$) between approximately 0.1 nM and approximately 1 nM, or approximately 0.1 nM and approximately 2 nM, or approximately 0.1 nM and approximately 3 nM, or approximately 0.1 nM and approximately 4 nM, or approximately 0.1 nM and approximately 5 nM, or approximately 0.1 nM and approximately 6 nM, or approximately 0.1 nM and approximately 7 nM, or approximately 0.1 nM and approximately 8 nM, or approximately 0.1 nM and approximately 9 nM, or approximately 0.1 nM and approximately 10 nM, or between approximately 0.01 nM and approximately 0.1 nM, or between approximately 0.01 nM and approximately 1 nM, or between approximately 0.01 nM and approximately 2 nM, or between approximately 0.01 nM and approximately 3 nM, or between approximately 0.01 nM and approximately 4 nM, or between approximately 0.01 nM and approximately 5 nM, or between approximately 0.01 nM and approximately 6 nM, or between approximately 0.01 nM and approximately 7 nM, or between approximately 0.01 nM and approximately 8 nM, or between approximately 0.01 nM and approximately 9 nM, or between approximately 0.6 nM and approximately 1.1 nM, or between approximately 0.7 nM and approximately 1.2 nM, or between approximately 0.5 and approximately 5 nM. In other specific embodiments, an anti-TNF-α antibody binds to TNF-α with a $K_D$ ($k_{off}/k_{on}$) of about 5 nM, about 3.5 nM, about 1.5 nM, about 1 nM, about 0.5 nM, about 0.1 nM, about 0.05 nM or about 0.01 nM. In specific embodiments, the $K_D$ ($k_{off}/k_{on}$) value is determined by assays well known in the art or described herein, e.g., ELISA, isothermal titration calorimetry (ITC), BIAcore, or fluorescent polarization assay.

In some embodiments, an anti-TNF-α antibody of the disclosure binds to TNF-α and inhibits the binding of TNF-α to p55, p75 or both at an IC$_{50}$ value of less than $5\times10^7$ nM, less than $10^7$ nM, less than $5\times10^6$ nM, less than $10^6$ nM, less than $5\times10^5$ nM, less than $10^5$ nM, less than $5\times10^4$ nM, less than $10^4$ nM, less than $5\times10^3$ nM, less than $10^3$ nM, less than $5\times10^2$ nM, less than 100 nM, less than 90 nM, less than 80 nM, less than 70 nM, 65 nM, less than 60 nM, less than 50 nM, less than 40 nM, less than 30 nM, less than 25 nM, less than 20 nM, less than 15 nM, less than 12 nM, less than 10 nM, less than 5 nM, less than 1 nM, less than $5\times10^{-1}$ nM, less than $10^{-1}$ nM, less than $5\times10^{-2}$ nM, less than $10^{-2}$ nM, less than $5\times10^{-3}$ nM, less than $10^{-3}$ nM, less than $5\times10^{-4}$ nM, or less than $10^{-4}$ nM, or with an IC$_{50}$ of any range between any pair of the foregoing values (e.g., $5\times10^7$ to 50 nM, or 15 nM to $5\times10^{-3}$ nM). IC$_{50}$ can be measured according to methods well known in the art or described herein, e.g., ELISA.

In other embodiments, an anti-TNF-α antibody of the disclosure binds to TNF-α and neutralizes TNF-α at an IC$_{50}$ value of less than $5\times10^7$ nM, less than $10^7$ nM, less than $5\times10^6$ nM, less than $10^6$ nM, less than $5\times10^5$ nM, less than $10^5$ nM, less than $5\times10^4$ nM, less than $10^4$ nM, less than $5\times10^3$ nM, less than $10^3$ nM, less than $5\times10^2$ nM, less than 100 nM, less than 90 nM, less than 80 nM, less than 70 nM, 65 nM, less than 60 nM, less than 50 nM, less than 40 nM, less than 30 nM, less than 25 nM, less than 20 nM, less than 15 nM, less than 12 nM, less than 10 nM, less than 5 nM, less than 1 nM, less than $5\times10^{-1}$ nM, less than $10^{-1}$ nM, less than $5\times10^{-2}$ nM, less than $10^{-2}$ nM, less than $5\times10^{-3}$ nM, less than $10^{-3}$ nM, less than $5\times10^{-4}$ nM, or less than $10^{-4}$ nM, or with an IC$_{50}$ of any range between any pair of the foregoing values (e.g., $5\times10^7$ to 50 nM, or 15 nM to $5\times10^{-3}$ nM). An exemplary neutralization assay that can be used to measure the IC$_{50}$ of an anti-TNF-α antibody is described in Section 7.5 below.

In certain specific embodiments, an anti-TNF-α antibody binds to TNF-α and inhibits the binding of TNF-α to p55, p75 or both, or inhibits TNF-α activity in a TNF-α neutralization assay, at an IC$_{50}$ value of between approximately 1 nM and approximately 10 nM, between approximately 1 nM and approximately 15 nM, between approximately 1 nM and approximately 20 nM, between approximately 1 nM and approximately 25 nM, between approximately 1 nM and approximately 30 nM, between approximately 1 nM and approximately 40 nM, between approximately 1 nM and approximately 50 nM, between approximately 10 nM and approximately 10$^2$ nM, between approximately 10$^2$ nM and approximately 10$^3$ nM, between approximately 10 nM and approximately 10$^4$ nM, between approximately 10$^4$ nM and approximately 10$^5$ nM, between approximately 10$^5$ nM and approximately 10$^6$ nM, or between approximately 10$^6$ nM and approximately 10$^7$ nM.

In other specific embodiments, an anti-TNF-α antibody binds to TNF-α and inhibits the binding of TNF-α to p55, p75 or both, or inhibits TNF-α activity in a TNF-α neutralization assay, at an IC$_{50}$ value of between approximately 5 nM and approximately 10 nM, between approximately 5 nM and approximately 15 nM, between approximately 10 nM and approximately 15 nM, between approximately 10 nM and approximately 20 nM, between approximately 10 nM and approximately 30 nM, between approximately 10 nM and approximately 40 nM, between approximately 10 nM and approximately 50 nM, between approximately 1 nM and approximately 100 nM, between approximately 10 nM and approximately 100 nM, between approximately 20 nM and approximately 100 nM, between approximately 30 nM and approximately 100 nM, between approximately 40 nM and approximately 100 nM, between approximately 50 nM and approximately 100 nM, between approximately 15 nM and approximately 25 nM, or between approximately 15 nM and approximately 20 nM.

In certain aspects of the foregoing embodiments, the $IC_{50}$ is measured in the presence of TNF-α at a concentration of 0.001 µM, 0.005 µM, 0.01 µM, 0.05 µM, 0.1 µM, 0.5 µM, 1 µM, 10 µM, 20 µM, 30 µM, 40 µM, 50 µM, 60 µM, 70 µM, 80 µM, 90 µM, 100 µM, 200 µM, 300 µM, 400 µM, 500 µM, 600 µM, 700 µM, 800 µM, 900 µM, 1000 µM or at a concentration of any range between any pair of the foregoing values (e.g., 0.01 to 50 µM, or 10 µM to 100 µM).

In certain embodiments, the kinetic properties of an antibody of the disclosure are comparable to, or improved relative to, the D2E7 antibody in a comparable assay. For example, in certain embodiments, an anti-TNF-α antibody of the disclosure binds to TNF-α with a $k_{on}$ rate ranging from 0.2× to 5× of the $k_{on}$ of D2E7, for example a $k_{on}$ of 0.2× of the $k_{on}$ of D2E7, a $k_{on}$ of 0.3× of the $k_{on}$ of D2E7, a $k_{on}$ of 0.4× of the $k_{on}$ of D2E7, a $k_{on}$ of 0.5× of the $k_{on}$ of D2E7, a $k_{on}$ of 0.6× of the $k_{on}$ of D2E7, a $k_{on}$ of 0.7× of the $k_{on}$ of D2E7, a $k_{on}$ of 0.8× of the $k_{on}$ of D2E7, a $k_{on}$ of 0.9× of the $k_{on}$ of D2E7, a $k_{on}$ of 1× of the $k_{on}$ of D2E7, a $k_{on}$ of 1.1× of the $k_{on}$ of D2E7, a $k_{on}$ of 1.2× of the $k_{on}$ of D2E7, a $k_{on}$ of 1.3× of the $k_{on}$ of D2E7, a $k_{on}$ of 1.4× of the $k_{on}$ of D2E7, a $k_{on}$ of 1.5× of the $k_{on}$ of D2E7, a $k_{on}$ of 1.75× of the $k_{on}$ of D2E7, a $k_{on}$ of 2× of the $k_{on}$ of D2E7, a $k_{on}$ of 2.25× of the $k_{on}$ of D2E7, a $k_{on}$ of 2.5× of the $k_{on}$ of D2E7, a $k_{on}$ of 2.75× of the $k_{on}$ of D2E7, a $k_{on}$ of 3× of the $k_{on}$ of D2E7, a $k_{on}$ of 3.5× of the $k_{on}$ of D2E7, a $k_{on}$ of 4× of the $k_{on}$ of D2E7, a $k_{on}$ of 4.5× of the $k_{on}$ of D2E7, a $k_{on}$ of 5× of the $k_{on}$ of D2E7, or a $k_{on}$ ranging between any pair of the foregoing values, e.g., a $k_{on}$ of 0.7×-1.5× of the $k_{on}$ of D2E7, a $k_{on}$ of 0.9×-1.3× of the $k_{on}$ of D2E7, a $k_{on}$ of 0.8×-2× of the $k_{on}$ of D2E7, a $k_{on}$ of 0.9×-3× of the $k_{on}$ of D2E7, etc.

In embodiments, an anti-TNF-α antibody of the disclosure binds to TNF-α with a $k_{off}$ rate ranging from 0.2× to 5× of the $k_{off}$ of D2E7, for example a $k_{off}$ of 0.2× of the $k_{off}$ of D2E7, a $k_{off}$ of 0.3× of the $k_{off}$ of D2E7, a $k_{off}$ of 0.4× of the $k_{off}$ of D2E7, a $k_{off}$ of 0.5× of the $k_{off}$ of D2E7, a $k_{off}$ of 0.6× of the $k_{off}$ of D2E7, a $k_{off}$ of 0.7× of the $k_{off}$ of D2E7, a $k_{off}$ of 0.8× of the $k_{off}$ of D2E7, a $k_{off}$ of 0.9× of the $k_{off}$ of D2E7, a $k_{off}$ of 1× of the $k_{off}$ of D2E7, a $k_{off}$ of 1.1× of the $k_{off}$ of D2E7, a $k_{off}$ of 1.2× of the $k_{off}$ of D2E7, a $k_{off}$ of 1.3× of the $k_{off}$ of D2E7, a $k_{off}$ of 1.4× of the $k_{off}$ of D2E7, a $k_{off}$ of 1.5× of the $k_{off}$ of D2E7, a $k_{off}$ of 1.75× of the $k_{off}$ of D2E7, a $k_{off}$ of 2× of the $k_{off}$ of D2E7, a $k_{off}$ of 2.25× of the $k_{off}$ of D2E7, a $k_{off}$ of 2.5× of the $k_{off}$ of D2E7, a $k_{off}$ of 2.75× of the $k_{off}$ of D2E7, a $k_{off}$ of 3× of the $k_{off}$ of D2E7, a $k_{off}$ of 3.5× of the $k_{off}$ of D2E7, a $k_{off}$ of 4× of the $k_{off}$ of D2E7, a $k_{off}$ of 4.5× of the $k_{off}$ of D2E7, a $k_{off}$ of 5× of the $k_{off}$ of D2E7, or a $k_{off}$ ranging between any pair of the foregoing values, e.g., a $k_{off}$ of 0.7×-1.5× of the $k_{off}$ of D2E7, a $k_{off}$ of 0.9×-1.3× of the $k_{off}$ of D2E7, a $k_{off}$ of 0.8×-2× of the $k_{off}$ of D2E7, a $k_{off}$ of 0.9×-3× of the $k_{off}$ of D2E7, etc.

In other embodiments, an anti-TNF-α antibody of the disclosure binds to TNF-α with a $K_A$ ($k_{on}/k_{off}$) ranging from 0.04× to 25× of the $K_A$ of D2E7, for example a $K_A$ of 0.04× of the $K_A$ of D2E7, a $K_A$ of 0.1× of the $K_A$ of D2E7, a $K_A$ of 0.25× of the $K_A$ of D2E7, a $K_A$ of 0.5× of the $K_A$ of D2E7, a $K_A$ of 0.6× of the $K_A$ of D2E7, a $K_A$ of 0.7× of the $K_A$ of D2E7, a $K_A$ of 0.8× of the $K_A$ of D2E7, a $K_A$ of 0.9× of the $K_A$ of D2E7, a $K_A$ of 1× of the $K_A$ of D2E7, a $K_A$ of 1.1× of the $K_A$ of D2E7, a $K_A$ of 1.25× of the $K_A$ of D2E7, a $K_A$ of 1.5× of the $K_A$ of D2E7, a $K_A$ of 1.75× of the $K_A$ of D2E7, a $K_A$ of 2× of the $K_A$ of D2E7, a $K_A$ of 2.5× of the $K_A$ of D2E7, a $K_A$ of 3× of the $K_A$ of D2E7, a $K_A$ of 4× of the $K_A$ of D2E7, a $K_A$ of 4×% of the $K_A$ of D2E7, a $K_A$ of 5× of the $K_A$ of D2E7, a $K_A$ of 7.5× of the $K_A$ of D2E7, a $K_A$ of 10× of the $K_A$ of D2E7, a $K_A$ of 12.5× of the $K_A$ of D2E7, a $K_A$ of 15× of the $K_A$ of D2E7, a $K_A$ of 20× of the $K_A$ of D2E7, a $K_A$ of 25× of the $K_A$ of D2E7, or a $K_A$ ranging between any pair of the foregoing values, e.g., a $K_A$ of 0.7×-1.25× of the $K_A$ of D2E7, a $K_A$ of 0.9×-1.5× of the $K_A$ of D2E7, a $K_A$ of 0.9×-2× of the $K_A$ of D2E7, a $K_A$ of 0.8×-1.75× of the $K_A$ of D2E7, a $K_A$ of 0.9×-5× of the $K_A$ of D2E7, or any value or range that can be calculated from the $k_{on}$ and $k_{off}$ rates disclosed herein.

In other embodiments, an anti-TNF-α antibody of the disclosure binds to TNF-α a $K_D$ ($k_{off}/k_{on}$) ranging from ranging from 0.04× to 25× of the $K_D$ of D2E7, for example a $K_D$ of 0.04× of the $K_D$ of D2E7, a $K_D$ of 0.1× of the $K_D$ of D2E7, a $K_D$ of 0.25× of the $K_D$ of D2E7, a $K_D$ of 0.5× of the $K_D$ of D2E7, a $K_D$ of 0.6× of the $K_D$ of D2E7, a $K_D$ of 0.7× of the $K_D$ of D2E7, a $K_D$ of 0.8× of the $K_D$ of D2E7, a $K_D$ of 0.9× of the $K_D$ of D2E7, a $K_D$ of 1× of the $K_D$ of D2E7, a $K_D$ of 1.1× of the $K_D$ of D2E7, a $K_D$ of 1.25× of the $K_D$ of D2E7, a $K_D$ of 1.5× of the $K_D$ of D2E7, a $K_D$ of 1.75× of the $K_D$ of D2E7, a $K_D$ of 2× of the $K_D$ of D2E7, a $K_D$ of 2.5× of the $K_D$ of D2E7, a $K_D$ of 3× of the $K_D$ of D2E7, a $K_D$ of 4× of the $K_D$ of D2E7, a $K_D$ of 4×% of the $K_D$ of D2E7, a $K_D$ of 5× of the $K_D$ of D2E7, a $K_D$ of 7.5× of the $K_D$ of D2E7, a $K_D$ of 10× of the $K_D$ of D2E7, a $K_D$ of 12.5× of the $K_D$ of D2E7, a $K_D$ of 15× of the $K_D$ of D2E7, a $K_D$ of 20× of the $K_D$ of D2E7, a $K_D$ of 25× of the $K_D$ of D2E7, or a $K_D$ ranging between any pair of the foregoing values, e.g., a $K_D$ of 0.7×-1.25× of the $K_D$ of D2E7, a $K_D$ of 0.9×-1.5× of the $K_D$ of D2E7, a $K_D$ of 0.9×-2× of the $K_D$ of D2E7, a $K_D$ of 0.8×-1.75× of the $K_D$ of D2E7, a $K_D$ of 0.9×-5× of the $K_D$ of D2E7, or any value or range that can be calculated from the $k_{on}$ and $k_{off}$ rates disclosed herein.

In some embodiments, an anti-TNF-α antibody of the disclosure binds to TNF-α and inhibits the binding of TNF-α to p55, p75 or both at an $IC_{50}$ value ranging from 50% to 200% of the $IC_{50}$ of D2E7, for example an $IC_{50}$ of 50% of the $IC_{50}$ of D2E7, an $IC_{50}$ of 60% of the $IC_{50}$ of D2E7, an $IC_{50}$ of 70% of the $IC_{50}$ of D2E7, an $IC_{50}$ of 75% of the $IC_{50}$ of D2E7, an $IC_{50}$ of 80% of the $IC_{50}$ of D2E7, an $IC_{50}$ of 90% of the $IC_{50}$ of D2E7, an $IC_{50}$ of 95% of the $IC_{50}$ of D2E7, an $IC_{50}$ of 100% of the $IC_{50}$ of D2E7, an $IC_{50}$ of 110% of the $IC_{50}$ of D2E7, an $IC_{50}$ of 120% of the $IC_{50}$ of D2E7, an $IC_{50}$ of 125% of the $IC_{50}$ of D2E7, an $IC_{50}$ of 130% of the $IC_{50}$ of D2E7, an $IC_{50}$ of 140% of the $IC_{50}$ of D2E7, an $IC_{50}$ of 150% of the $IC_{50}$ of D2E7, an $IC_{50}$ of 160% of the $IC_{50}$ of D2E7, an $IC_{50}$ of 170% of the $IC_{50}$ of D2E7, an $IC_{50}$ of 175% of the $IC_{50}$ of D2E7, an $IC_{50}$ of 180% of the $IC_{50}$ of D2E7, an $IC_{50}$ of 190% of the $IC_{50}$ of D2E7, an $IC_{50}$ of 200% of the $IC_{50}$ of D2E7, or an $IC_{50}$ of any range between any pair of the foregoing values, e.g., an $IC_{50}$ of 75%-125% of the $IC_{50}$ of D2E7, an $IC_{50}$ of 90%-130% of the $IC_{50}$ of D2E7, an $IC_{50}$ of 95%-125% of the $IC_{50}$ of D2E7, an $IC_{50}$ of 90%-110% of the $IC_{50}$ of D2E7, an $IC_{50}$ of 90%-180% of the $IC_{50}$ of D2E7, or an $IC_{50}$ of 80%-175% of the $IC_{50}$ of D2E7. In other embodiments, a single CDR substitution can result in the foregoing differences in $IC_{50}$ as compared to D2E7, whereas an anti-TNF-α antibody of the disclosure can comprise such substitution and up to 16 additional substitutions as compared to D2E7.

In other embodiments, an anti-TNF-α antibody of the disclosure binds to TNF-α and neutralizes TNF-α at an $IC_{50}$ value ranging from 50% to 200% of the $IC_{50}$ of D2E7, for example an $IC_{50}$ of 50% of the $IC_{50}$ of D2E7, an $IC_{50}$ of 60% of the $IC_{50}$ of D2E7, an $IC_{50}$ of 70% of the $IC_{50}$ of D2E7, an $IC_{50}$ of 75% of the $IC_{50}$ of D2E7, an $IC_{50}$ of 80% of the $IC_{50}$ of D2E7, an $IC_{50}$ of 90% of the $IC_{50}$ of D2E7, an $IC_{50}$ of 95% of the $IC_{50}$ of D2E7, an $IC_{50}$ of 100% of the $IC_{50}$ of D2E7, an $IC_{50}$ of 110% of the $IC_{50}$ of D2E7, an $IC_{50}$ of 120% of the $IC_{50}$ of D2E7, an $IC_{50}$ of 125% of the $IC_{50}$ of D2E7, an $IC_{50}$ of 130% of the $IC_{50}$ of D2E7, an $IC_{50}$ of 140% of the $IC_{50}$ of D2E7, an $IC_{50}$ of 150% of the $IC_{50}$ of D2E7, an $IC_{50}$ of 160% of the IC$_{50}$ of D2E7, an IC$_{50}$ of 170% of the IC$_{50}$ of D2E7, an IC$_{50}$ of 175% of the IC$_{50}$ of D2E7, an IC$_{50}$ of 180% of the IC$_{50}$ of D2E7, an IC$_{50}$ of 190% of the IC$_{50}$ of D2E7, an IC$_{50}$ of 200% of the IC$_{50}$ of D2E7, or an IC$_{50}$ of any range between any pair of the foregoing values, e.g., an IC$_{50}$ of 75%-125% of the IC$_{50}$ of D2E7, an IC$_{50}$ of 90%-130% of the IC$_{50}$ of D2E7, an IC$_{50}$ of 95%-125% of the IC$_{50}$ of D2E7, an IC$_{50}$ of 90%-110% of the IC$_{50}$ of D2E7, an IC$_{50}$ of 90%-180% of the IC$_{50}$ of D2E7, or an IC$_{50}$ of 80%-175% of the IC$_{50}$ of D2E7. In other embodiments, a single CDR substitution can result in the foregoing differences in IC$_{50}$ as compared to D2E7, whereas an anti-TNF-α antibody of the disclosure can comprise such substitution and up to 16 additional substitutions as compared to D2E7.

7.5 Reduced Immunogenicity of Anti-TNF-α Antibodies

In certain aspects, the present disclosure provides anti-TNF-α antibodies having reduced immunogenicity as compared to D2E7. The present disclosure also provides anti-TNF-α antibodies having multiple amino acid substitutions in their CDRs as compared to the CDRs of D2E7, wherein at least one substitution reduces the immunogenicity of the antibody as compared to D2E7. In certain embodiments, the reduced immunogenicity results from one or more amino acid substitutions that result in eliminating or mitigating one or more T cell epitopes.

In certain aspects, the anti-TNF-α antibodies of the disclosure having reduced immunogenicity have comparable or improved biological activity as compared to D2E7, e.g., affinity towards TNF-α or neutralization of TNF-α activity. Such properties can be tested, for example, by the methods described in Section 7.3 above.

In certain embodiments, the immunogenicity of an TNF-α antibody of the disclosure is reduced relative to D2E7 antibody. Such antibodies generally have variant sequences relative to the heavy and/or light chain variable region in regions corresponding to SEQ ID NO:81 and/or SEQ ID NO:82, and/or SEQ ID NO:83. The antibodies will generally have one, two or three amino acid substitutions in one, two or all three sequences corresponding to SEQ ID NO:81, SEQ ID NO:82, and SEQ ID NO:83, although up to four or five substitutions one, two or all three regions are contemplated herein.

Exemplary CDR-L1 substitutions yielding antibodies with lower immunogenicity as compared to D2E7 are listed in Table 11. Antibodies of the disclosure can comprise any of the substitutions or combinations of substitutions listed in Table 11, and, optionally, one or more additional substitutions, such as the CDR mutations in any of Tables 12-25, singly or in combination.

As used in the present disclosure, the term "reduced immunogenicity" indicates that the variant sequence as compared to SEQ ID NO:81, SEQ ID NO:82 or SEQ ID NO:83 elicits a reduced proliferative response in peripheral blood mononuclear cells as compared to a peptide of SEQ ID NO:81, SEQ ID NO:82, or SEQ ID NO:83, respectively. An exemplary proliferation assay that can be used to evaluate the proliferative response is set forth in Section 8 below. The reduced proliferative response can be reflected in terms of the percentage of responders, the stimulation index, or both.

In other embodiments, as compared to a peptide having the sequence of SEQ ID NO:81, SEQ ID NO:82, or SEQ ID NO; 83, the variant sequence results in at least 25% fewer responders, in at least 30% fewer responders, in at least 35% fewer responders, in at least 40% fewer responders, in at least 45% fewer responders, in at least 50% fewer responders, in at least 60% fewer responders, in at least 65% fewer responders, in at least 70% fewer responders, in at least 75% fewer responders, in at least 80% fewer responders, in at least 85% fewer responders, in at least 90% fewer responders, in at least 95% fewer responders, 100% fewer responders, or a reduction in responders in a range between any of the foregoing values, e.g., 25%-75% fewer responders, 50%-90% fewer responders, 60%-100% fewer responders, 70%-90% fewer responders, or the like.

In other embodiments, the variant sequence results in a stimulation index that is at least 5% less, at least 10% less, at least 15% less, at least 20% less, at least 25% less, at least 30% less, at least 35% less, or at least 40% less than the stimulation index elicited by a peptide of SEQ ID NO:81, SEQ ID NO:82, or SEQ ID NO; 83, respectively, or results in a stimulation index reduced by a range between any of the foregoing values as compared to a peptide of SEQ ID NO:81, SEQ ID NO:82, or SEQ ID NO; 83, e.g., 5%-20% less, 10%-30% less, 25%-35% less, 30%-40% less, or the like.

Exemplary embodiments of anti-TNF-α antibodies with reduced immunogenicity as compared to D2E7 comprise one or more of the CDR substitutions or combinations of substitutions set forth in Table 11.

7.6 Antibody Conjugates

The anti-TNF-α antibodies of the disclosure include antibody conjugates that are modified, e.g., by the covalent attachment of any type of molecule to the antibody, such that covalent attachment does not interfere with binding to TNF-α.

In certain aspects, an anti-TNF-α antibody of the disclosure can be conjugated to an effector moiety or a label. The term "effector moiety" as used herein includes, for example, antineoplastic agents, drugs, toxins, biologically active proteins, for example enzymes, other antibody or antibody fragments, synthetic or naturally occurring polymers, nucleic acids (e.g., DNA and RNA), radionuclides, particularly radioiodide, radioisotopes, chelated metals, nanoparticles and reporter groups such as fluorescent compounds or compounds which can be detected by NMR or ESR spectroscopy.

In one example, anti-TNF-α antibodies can be conjugated to an effector moiety, such as a cytotoxic agent, a radionuclide or drug moiety to modify a given biological response. The effector moiety can be a protein or polypeptide, such as, for example and without limitation, a toxin (such as abrin, ricin A, *Pseudomonas* exotoxin, or *Diphtheria* toxin), a signaling molecule (such as α-interferon, β-interferon, nerve growth factor, platelet derived growth factor or tissue plasminogen activator), a thrombotic agent or an anti-angiogenic agent (e.g., angiostatin or endostatin) or a biological response modifier such as a cytokine or growth factor (e.g., interleukin-1 (IL-1), interleukin-2 (IL-2), interleukin-6 (IL-6), granulocyte macrophage colony stimulating factor (GM-CSF), granulocyte colony stimulating factor (G-CSF), or nerve growth factor (NGF)).

In another example the effector moieties can be cytotoxins or cytotoxic agents. Examples of cytotoxins and cytotoxic agents include taxol, cytochalasin B, gramicidin D, ethidium bromide, emetine, mitomycin, etoposide, tenoposide, vincristine, vinblastine, colchicin, doxorubicin, daunorabicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector moieties also include, but are not limited to, antimetabolites (e.g. methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C5 and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, anthramycin (AMC), calicheamicins or duocarmycins), and anti-mitotic agents (e.g., vincristine and vinblastine).

Other effector moieties can include radionuclides such as, but not limited to, $^{111}$In and $^{90}$Y, Lu$^{177}$, Bismuth$^{213}$, Californium$^{252}$, Iridium$^{192}$ and Tungsten$^{188}$/Rhenium$^{188}$ and drugs such as, but not limited to, alkylphosphocholines, topoisomerase I inhibitors, taxoids and suramin.

Techniques for conjugating such effector moieties to antibodies are well known in the art (See, e.g., Hellstrom et al., Controlled Drug Delivery, 2nd Ed., at pp. 623-53 (Robinson et al., eds., 1987)); Thorpe et al., 1982, Immunol. Rev. 62:119-58 and Dubowchik et al., 1999, Pharmacology and Therapeutics 83:67-123).

In one example, the antibody or fragment thereof is fused via a covalent bond (e.g., a peptide bond), through the antibody's N-terminus or the C-terminus or internally, to an amino acid sequence of another protein (or portion thereof; for example, at least a 10, 20 or 50 amino acid portion of the protein). The antibody, or fragment thereof, can linked to the other protein at the N-terminus of the constant domain of the antibody. Recombinant DNA procedures can be used to create such fusions, for example as described in WO 86/01533 and EP0392745. In another example the effector molecule can increase half-life in vivo, and/or enhance the delivery of an antibody across an epithelial barrier to the immune system. Examples of suitable effector molecules of this type include polymers, albumin, albumin binding proteins or albumin binding compounds such as those described in WO 2005/117984.

In certain aspects, an anti-TNF-α antibody is conjugated to a small molecule toxin. In certain exemplary embodiments, an anti-TNF-α antibody of the disclosure is conjugated to a dolastatin or a dolastatin peptidic analogs or derivatives, e.g., an auristatin (U.S. Pat. Nos. 5,635,483 and 5,780,588). The dolastatin or auristatin drug moiety may be attached to the antibody through its N (amino) terminus, C (carboxyl) terminus or internally (WO 02/088172). Exemplary auristatin embodiments include the N-terminus linked monomethylauristatin drug moieties DE and DF, as disclosed in U.S. Pat. No. 7,498,298, which is hereby incorporated by reference in its entirety (disclosing, e.g., linkers and methods of preparing monomethylvaline compounds such as MMAE and MMAF conjugated to linkers).

In other exemplary embodiments, small molecule toxins include but are not limited to calicheamicin, maytansine (U.S. Pat. No. 5,208,020), trichothene, and CC1065. In one embodiment of the disclosure, the antibody is conjugated to one or more maytansine molecules (e.g., about 1 to about 10 maytansine molecules per antibody molecule). Maytansine may, for example, be converted to May-SS-Me which may be reduced to May-SH3 and reacted with an antibody (Chari et al., 1992, Cancer Research 52: 127-131) to generate a maytansinoid-antibody or maytansinoid-Fc fusion conjugate. Structural analogues of calicheamicin that can also be used include but are not limited to $\gamma_1^1$, $\gamma_3^1$, $\gamma_3^1$ N-acetyl-$\gamma_1^1$, PSAG, and $\theta_1^1$, (Hinman et al., 1993, Cancer Research 53:3336-3342; Lode et al., 1998, Cancer Research 58:2925-2928; U.S. Pat. No. 5,714,586; U.S. Pat. No. 5,712,374; U.S. Pat. No. 5,264,586; U.S. Pat. No. 5,773,001).

Antibodies of the disclosure can also be conjugated to liposomes for targeted delivery (See, e.g., Park et al., 1997, Adv. Pharmacol. 40:399-435; Marty & Schwendener, 2004, Methods in Molecular Medicine 109:389-401).

In one example antibodies of the present disclosure can be attached to poly(ethyleneglycol) (PEG) moieties. In one particular example the antibody is an antibody fragment and the PEG moieties can be attached through any available amino acid side-chain or terminal amino acid functional group located in the antibody fragment, for example any free amino, imino, thiol, hydroxyl or carboxyl group. Such amino acids can occur naturally in the antibody fragment or can be engineered into the fragment using recombinant DNA methods. See, for example, U.S. Pat. No. 5,219,996. Multiple sites can be used to attach two or more PEG molecules. PEG moieties can be covalently linked through a thiol group of at least one cysteine residue located in the antibody fragment. Where a thiol group is used as the point of attachment, appropriately activated effector moieties (for example, thiol selective derivatives such as maleimides and cysteine derivatives) can be used.

In a specific example, an anti-TNF-α antibody conjugate is a modified Fab' fragment which is PEGylated, i.e., has PEG (poly(ethyleneglycol)) covalently attached thereto, e.g., according to the method disclosed in EP0948544. See also Poly(ethyleneglycol) Chemistry, Biotechnical and Biomedical Applications, (J. Milton Harris (ed.), Plenum Press, New York, 1992); Poly(ethyleneglycol) Chemistry and Biological Applications, (J. Milton Harris and S. Zalipsky, eds., American Chemical Society, Washington D.C., 1997); and Bioconjugation Protein Coupling Techniques for the Biomedical Sciences, (M. Aslam and A. Dent, eds., Grove Publishers, New York, 1998); and Chapman, 2002, Advanced Drug Delivery Reviews 54:531-545. PEG can be attached to a cysteine in the hinge region. In one example, a PEG-modified Fab' fragment has a maleimide group covalently linked to a single thiol group in a modified hinge region. A lysine residue can be covalently linked to the maleimide group and to each of the amine groups on the lysine residue can be attached a methoxypoly(ethyleneglycol) polymer having a molecular weight of approximately 20,000 Da. The total molecular weight of the PEG attached to the Fab' fragment can therefore be approximately 40,000 Da.

The word "label" when used herein refers to a detectable compound or composition which can be conjugated directly or indirectly to an anti-TNF-α antibody of the disclosure. The label can itself be detectable (e.g., radioisotope labels or fluorescent labels) or, in the case of an enzymatic label, can catalyze chemical alteration of a substrate compound or composition which is detectable. Useful fluorescent moieties include, but are not limited to, fluorescein, fluorescein isothiocyanate, rhodamine, 5-dimethylamine-1-napthalenesulfonyl chloride, phycoerythrin and the like. Useful enzymatic labels include, but are not limited to, alkaline phosphatase, horseradish peroxidase, glucose oxidase and the like.

Additional anti-TNF-α antibody conjugates that are useful for, inter alia, diagnostic purposes, are described in Section 7.7 below.

7.7 Diagnostic Uses of Anti-TNF-α Antibodies

The anti-TNF-α antibodies of the disclosure, including those antibodies that have been modified, e.g., by biotinylation, horseradish peroxidase, or any other detectable moiety (including those described in Section 7.6), can be advantageously used for diagnostic purposes.

In particular, the anti-TNF-α antibodies can be used, for example, but not limited to, to purify or detect TNF-α, including both in vitro and in vivo diagnostic methods. For example, the antibodies have use in immunoassays for qualitatively and quantitatively measuring levels of TNF-α in biological samples. See, e.g., Harlow et al., Antibodies: A Laboratory Manual, Second Edition (Cold Spring Harbor Laboratory Press, 1988), which is incorporated by reference herein in its entirety. In one embodiment, the anti-TNF-α antibodies of the disclosure can be used for detecting and quantitating levels of TNF-α in the serum.

The present disclosure further encompasses antibodies or fragments thereof conjugated to a diagnostic agent. The antibodies can be used diagnostically, for example, to detect expression of a target of interest in specific cells, tissues, or serum; or to monitor the development or progression of an immunologic response as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody (or fragment thereof) or indirectly, through an intermediate (such as, for example, a linker known in the art) using techniques known in the art. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, acetylcholinesterase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

The disclosure provides for the detection of expression of TNF-α, comprising contacting a biological sample (cells, tissue, or body fluid of an individual) using one or more anti-TNF-α antibodies of the disclosure (optionally conjugated to detectable moiety), and detecting whether or not the sample is positive for TNF-α expression, or whether the sample has altered (e.g., reduced or increased) expression as compared to a control sample.

Diseases that can be diagnosed using the present methods include, but are not limited to, the diseases described herein. In certain embodiments, the tissue or body fluid is peripheral blood, peripheral blood leukocytes, biopsy tissues such as lung or skin biopsies, and tissue.

7.8 Therapeutic Methods Using Anti-TNF-α Antibodies

7.8.1 Clinical Benefits

The TNF-α antibodies of the present disclosure are useful for treating disorders or symptoms of various immune and autoimmune pathologies as well as inflammatory diseases. TNF-α-related pathologies and diseases that can be treated with the anti-TNF-α antibodies of the disclosure include, but are not limited to, the following:

Acute and chronic immune and autoimmune pathologies, such as systemic lupus erythematosus, rheumatoid arthritis, thyroidosis, graft versus host disease, scleroderma, diabetes mellitus, Grave's disease, and the like;

Infections, including, but not limited to, sepsis syndrome, cachexia, circulatory collapse and shock resulting from acute or chronic bacterial infection, acute and chronic parasitic and/or bacterial, viral or fungal infectious diseases, such as AIDS (including sequelae such as cachexia, autoimmune disorders, AIDS dementia complex and infections);

Inflammatory diseases, such as chronic inflammatory pathologies and vascular inflammatory pathologies, including chronic inflammatory pathologies such as sarcoidosis, chronic inflammatory bowel disease, ulcerative colitis, and Crohn's pathology and vascular inflammatory pathologies, such as, but not limited to, disseminated intravascular coagulation, atherosclerosis, and Kawasaki's pathology;

Neurodegenerative diseases, including, but not limited to, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea, drug-induced movement disorders, such as those induced by drugs which block the CNS, dopamine receptors; hypokinetic movement disorders, such as Parkinson's disease; Progressive supranucleo palsy, Cerebellar and Spinocerebellar Disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and Machado-Joseph); and systemic disorders (Refsum's disease, abetalipoprotemia, ataxia, telangiectasia, and mitochondrial multi. system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type, Wernicke-Korsakoff syndrome; chronic alcoholism; Creutzfeldt-Jakob disease; subacute sclerosing panencephalitis, Hallerrorden-Spatz disease,- and Dementia pugilistica, or any subset thereof;

Malignant pathologies involving TNF-α secreting tumors or other malignancies involving TNF-α, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides), and Alcohol-induced hepatitis.

In certain specific embodiments, the antibodies of the disclosure are used to treat one or more of:

Moderate to severe rheumatoid arthritis (RA) in adults.

Moderate to severe polyarticular juvenile idiopathic arthritis (JIA) in children 4 years of age and older.

Psoriatic arthritis (PsA) in adults.

Ankylosing spondylitis (AS) in adults.

Moderate to severe Crohn's disease (CD) in adults who have not responded well to conventional treatments.

Moderate to severe chronic plaque psoriasis (Ps) in adults.

Accordingly, the present disclosure provides methods of treating any of the foregoing diseases in a patient in need thereof, comprising: administering to the patient an anti-TNF-α antibody of the disclosure. Optionally, said administration is repeated, e.g., after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a patient receives anti-TNF-α therapy for a prolonged period of time, e.g., 6 months, 1 year or more. The amount of anti-TNF-α antibody administered to the patient is in certain embodiments a therapeutically effective amount. As used herein, a "therapeutically effective" amount of TNF-α antibody can be administered as a single dose or over the course of a therapeutic regimen, e.g., over the course of a week, two weeks, three weeks, one month, three months, six months, one year, or longer. Exemplary therapeutic regimens are described in Section 7.11 below.

According to the present disclosure, treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom the anti-TNF-α antibody of the disclosure is administered is preferably a mammal such as a non-primate (e.g., cow, pig, horse, cat, dog, rat, etc.) or a primate (e.g., monkey or human). In certain embodiments, the subject or patient is a human. In certain aspects, the human is a pediatric patient. In other aspects, the human is an adult patient.

7.9 Pharmaceutical Compositions and Routes of Administration

Compositions comprising an anti-TNF-α antibody of the disclosure and, optionally one or more additional therapeutic agents, such as the combination therapeutic agents described in Section 7.10 below, are provided herein. The compositions will usually be supplied as part of a sterile, pharmaceutical composition that will normally include a pharmaceutically acceptable carrier. This composition can be in any suitable form (depending upon the desired method of administering it to a patient).

The anti-TNF-α antibodies of the disclosure can be administered to a patient by a variety of routes such as orally, transdermally, subcutaneously, intranasally, intravenously, intramuscularly, intraocularly, topically, intrathecally and intracerebroventricularly. The most suitable route for administration in any given case will depend on the particular antibody, the subject, and the nature and severity of the disease and the physical condition of the subject.

For treatment of indications described herein, the effective dose of an anti-TNF-α antibody of the disclosure can range from about 0.001 to about 75 mg/kg per single (e.g., bolus) administration, multiple administrations or continuous administration, or to achieve a serum concentration of 0.01-5000 μg/mL serum concentration per single (e.g., bolus) administration, multiple administrations or continuous administration, or any effective range or value therein depending on the condition being treated, the route of administration and the age, weight and condition of the subject. In a certain embodiment, each dose can range from about 0.5 μg to about 50 μg per kilogram of body weight, for example from about 3 μg to about 30 μg per kilogram body weight. The antibody can be formulated as an aqueous solution and administered by subcutaneous injection.

Pharmaceutical compositions can be conveniently presented in unit dose forms containing a predetermined amount of an anti-TNF-α antibody of the disclosure per dose. Such a unit can contain for example but without limitation 5 mg to 5 g, for example 10 mg to 1 g, or 20 to 50 mg. Pharmaceutically acceptable carriers for use in the disclosure can take a wide variety of forms depending, e.g., on the condition to be treated or route of administration.

Therapeutic formulations of the anti-TNF-α antibodies of the disclosure can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gly-uconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, $\alpha$-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Nonionic surfactants can be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents. Further formulations suitable for the anti-TNF-$\alpha$ antibodies of the disclosure are disclosed in U.S. Pat. App. No. 2004/0033228 A1, the contents of which are incorporated by reference herein in their entirety.

The formulation herein can also contain a combination therapeutic agent in addition to the anti-TNF-$\alpha$ antibody of the disclosure. Examples of suitable combination therapeutic agents are provided in Section 7.10 below.

The dosing schedule for subcutaneous administration can vary from once every six months, five months, four months, three months, two months, once a month to biweekly, weekly, or daily depending on a number of clinical factors, including the type of disease, severity of disease, and the patient's sensitivity to the anti-TNF-$\alpha$ antibody.

The dosage of an anti-TNF-$\alpha$ antibody of the disclosure to be administered of will vary according to the particular antibody, the type of autoimmune or inflammatory disease, the subject, and the nature and severity of the disease, the physical condition of the subject, the therapeutic regimen (e.g., whether a combination therapeutic agent is used), and the selected route of administration; the appropriate dosage can be readily determined by a person skilled in the art.

For the treatment and/or prophylaxis of autoimmune or inflammatory disease in humans and animals, pharmaceutical compositions comprising anti-TNF-$\alpha$ antibodies can be administered to patients (e.g., human subjects) at therapeutically or prophylactically effective dosages (e.g., dosages which result in inhibition of an autoimmune or inflammatory disease and/or relief of autoimmune or inflammatory disease symptoms) using any suitable route of administration, such as injection and other routes of administration known in the art for antibody-based clinical products.

It will be recognized by one of skill in the art that the optimal quantity and spacing of individual dosages of an anti-TNF-$\alpha$ antibody of the disclosure will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

7.10 Combination Therapy

Described below are combinatorial methods in which the anti-TNF-$\alpha$ antibodies of the disclosure can be utilized. The combinatorial methods of the disclosure involve the administration of at least two agents to a patient, the first of which is an anti-TNF-$\alpha$ antibody of the disclosure, and the additional agent(s) is a combination therapeutic agent. The anti-TNF-$\alpha$ antibody and the combination therapeutic agent(s) can be administered simultaneously, sequentially or separately.

The combinatorial therapy methods of the present disclosure can result in a greater than additive effect, providing therapeutic benefits where neither the anti-TNF-$\alpha$ antibody or combination therapeutic agent administered in an amount that is alone therapeutically effective.

In the present methods, the anti-TNF-$\alpha$ antibody of the disclosure and the combination therapeutic agent can be administered concurrently, either simultaneously or successively. As used herein, the anti-TNF-$\alpha$ antibody of the disclosure and the combination therapeutic agent are said to be administered successively if they are administered to the patient on the same day, for example during the same patient visit. Successive administration can occur 1, 2, 3, 4, 5, 6, 7 or 8 hours apart. In contrast, the anti-TNF-$\alpha$ antibody of the disclosure and the combination therapeutic agent are said to be administered separately if they are administered to the patient on the different days, for example, the anti-TNF-$\alpha$ antibody of the disclosure and the combination therapeutic agent can be administered at a 1-day, 2-day or 3-day, one-week, 2-week or monthly intervals. In the methods of the present disclosure, administration of the anti-TNF-$\alpha$ antibody of the disclosure can precede or follow administration of the combination therapeutic agent.

As a non-limiting example, the anti-TNF-$\alpha$ antibody of the disclosure and combination therapeutic agent can be administered concurrently for a period of time, followed by a second period of time in which the administration of the anti-TNF-$\alpha$ antibody of the disclosure and the combination therapeutic agent is alternated.

Because of the potentially synergistic effects of administering an anti-TNF-$\alpha$ antibody of the disclosure and a combination therapeutic agent, such agents can be administered in amounts that, if one or both of the agents is administered alone, is/are not therapeutically effective.

In certain aspects, the combination therapeutic agent is an anti-rheumatic drug, an anti-inflammatory agent, a chemotherapeutic agent, a radiotherapeutic, an immunosuppressive agent, or a cytotoxic drug.

Anti-rheumatic drugs include, but are not limited to, auranofin, azathioprine, chloroquine, D-penicillamine, gold sodium thiomalate hydroxychloroquine, Myocrisin and sulfasalzine methotrexate.

Anti-inflammatory agents include, but are not limited to, dexamethasone, pentasa, mesalazine, asacol, codeine phosphate, benorylate, fenbufen, naprosyn, diclofenac, etodolac and indomethacin, aspirin and ibuprofen.

Chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), antimitotic agents, cisdichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, eolociximab, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In yet other aspects of the disclosure, the combination therapeutic agent is a TNF-α antagonist other than the anti-TNF-α antibody of the disclosure. Examples of such TNF-α antagonists include, but are not limited to, soluble TNF-α receptors; etanercept (ENBREL™; Immunex) or a fragment, derivative or analog thereof; infliximab (REMICADE®; Centacor) or a derivative, analog or antigen-binding fragment thereof; IL-10, which is known to block TNF-α production via interferon-γ-activated macrophages (Oswald et al., 1992, Proc. Natl. Acad. Sci. USA 89:8676-8680), TNFR-IgG (Ashkenazi et al., 1991, Proc. Natl. Acad. Sci. USA 88:10535-10539); the murine product TBP-1 (Serono/Yeda); the vaccine CytoTAb (Protherics); antisense molecule 104838 (ISIS); the peptide RDP-58 (SangStat); thalidomide (Celgene); CDC-801 (Celgene); DPC-333 (Dupont); VX-745 (Vertex); AGIX-4207 (AtheroGenics); ITF-2357 (Italfarmaco); NPI-13021-31 (Nereus); SCIO-469 (Scios); TACE targeter (Immunix/AHP); CLX-120500 (Calyx); Thiazolopyrim (Dynavax); auranofin (Ridaura) (SmithKline Beecham Pharmaceuticals); quinacrine (mepacrine dichlorohydrate); tenidap (Enablex); Melanin (Large Scale Biological); and anti-p38 MAPK agents by Uriach.

Additional second therapeutic agents useful in combination with an anti-TNF-α antibody and particular indications for which combination therapy with such second therapeutic agents are useful are disclosed in WO 2004/004633, which is incorporated by reference herein in its entirety.

7.11 Therapeutic Regimens

The present disclosure provides therapeutic regimens involving the administration of the anti-TNF-α antibodies of the disclosure. The therapeutic regimen will vary depending on the patient's age, weight, and disease condition. The therapeutic regimen can continue for 2 weeks to indefinitely. In specific embodiments, the therapeutic regimen is continued for 2 weeks to 6 months, from 3 months to 5 years, from 6 months to 1 or 2 years, from 8 months to 18 months, or the like. The therapeutic regimen can be a non-variable dose regimen or a multiple-variable dose regimen, for example as described in WO 2005/110452, which is incorporated by reference in its entirety.

For the dosage exemplary regimens described below, the anti-TNF-α antibody can be administered as a sterile, preservative-free solution for subcutaneous administration.

In certain embodiments, the drug product is supplied as either a single-use, prefilled pen within which is enclosed a 1 mL prefilled glass syringe, or as a single-dose, 1 mL prefilled glass syringe. For adult patients, in certain embodiments the syringe delivers 0.8 mL of a pharmaceutically acceptable solution comprising the anti-TNF-α antibody of the disclosure. In a specific embodiment, in addition to the antibody the solution contains 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80, and water for injection (USP) with sodium hydroxide added as necessary to adjust pH. For pediatric patients, in certain embodiments the syringe delivers 0.4 mL of a pharmaceutically acceptable solution comprising the anti-TNF-α antibody of the disclosure. In a specific embodiment, in addition to the antibody the solution contains 2.47 mg sodium chloride, 0.34 mg monobasic sodium phosphate dihydrate, 0.61 mg dibasic sodium phosphate dihydrate, 0.12 mg sodium citrate, 0.52 mg citric acid monohydrate, 4.8 mg mannitol, 0.4 mg polysorbate 80, and water for injection (USP) with sodium hydroxide added as necessary to adjust pH.

For treatment rheumatoid arthritis, psoriatic arthritis, and ankylosing spondylitis, an anti-TNF-α antibody of the disclosure can be administered at a dose of 10 to 50 mg (e.g., 10 mg, 15 mg, 20 mg, 25 mg, 30 mg, 35 mg, 40 mg, 45 mg or 50 mg) every other week. Methotrexate, glucocorticoids, salicylates, nonsteroidal anti-inflammatory drugs (NSAIDs), analgesics or other disease-modifying antirheumatics drug (DMARDs) can be continued during treatment with the anti-TNF-α antibody of the disclosure. In rheumatoid arthritis, some patients not taking concomitant methotrexate can derive additional benefit from increasing the dosing frequency from biweekly to weekly.

For treatment of juvenile idiopathic arthritis, an anti-TNF-α antibody of the disclosure is administered at a dose that depends on the patient's weight. In certain non-limiting embodiments, the dose for pediatric patients weighing 15 kg (33 lbs) to under 30 kg (66 lbs) ranges from 5 to 25 mg (e.g., 5 mg, 7.5 mg, 10 mg, 12.5 mg, 15 mg, 20 mg, or 25 mg) every other week. In certain non-limiting embodiments, the dose for pediatric patients weighing greater than 30 kg (66 lbs) ranges from 10 to 50 mg (e.g., 10 mg, 15 mg, 20 mg, 25 mg, 30 mg, 35 mg, 40 mg, 45 mg or 50 mg) every other week. Methotrexate, glucocorticoids, salicylates, NSAIDs or analgesics can be continued during treatment with the anti-TNF-α antibody.

For treatment of Crohn's Disease, an anti-TNF-α antibody of the disclosure can be administered in certain non-limiting embodiments at a dose of 40-280 mg (e.g., 40 mg, 80 mg, 100 mg, 120 mg, 140 mg, 160 mg, 180 mg, 200 mg, 240 mg, or 280 mg) given initially (on Day 1 or divided between Day 1 and Day 2), followed by a dose of approximately 40% to 60% (e.g., 50%) of the initial dose two weeks later (Day 15). Two weeks later (Day 29), a maintenance dose of 20% to 30% (e.g., 25%) of the initial dose is administered every other week. Aminosalicylates, corticosteroids, and/or immunomodulatory agents (e.g., 6-mercaptopurine and azathioprine) can be continued during treatment with the anti-TNF-α antibody.

For treatment of plaque psoriasis, an anti-TNF-α antibody of the disclosure can be administered in certain non-limiting embodiments at a dose of 40-160 mg (e.g., 40 mg, 80 mg, 100 mg, 120 mg, 140 mg, or 160 mg given initially followed by half the initial dose given every other week starting one week after the initial dose.

7.12 Diagnostic and Pharmaceutical Kits

Encompassed by the present disclosure are pharmaceutical kits containing the anti-TNF-α antibodies (including antibody conjugates) of the disclosure. The pharmaceutical kit is a package comprising the anti-TNF-α antibody of the disclosure (e.g., either in lyophilized form or as an aqueous solution) and one or more of the following:
- A combination therapeutic agent, for example as described in Section 7.10 above;
- A device for administering the anti-TNF-α antibody, for example a pen, needle and/or syringe; and
- Pharmaceutical grade water or buffer to resuspend the antibody if the antibody is in lyophilized form.

In certain aspects, each unit dose of the anti-TNF-α antibody is packaged separately, and a kit can contain one or more unit doses (e.g., two unit doses, three unit doses, four unit doses, five unit doses, eight unit doses, ten unit doses, or more). In a specific embodiment, the one or more unit doses are each housed in a syringe or pen.

Diagnostic kits containing the anti-TNF-α antibodies (including antibody conjugates) of the disclosure are also encompassed herein. The diagnostic kit is a package comprising the anti-TNF-α antibody of the disclosure (e.g., either in lyophilized form or as an aqueous solution) and one or more reagents useful for performing a diagnostic assay. Where the anti-TNF-α antibody is labeled with an enzyme, the kit can include substrates and cofactors required by the enzyme (e.g., a substrate precursor which provides the detectable chromophore or fluorophore). In addition, other additives can be included, such as stabilizers, buffers (e.g., a block buffer or lysis buffer), and the like. In certain embodiments, the anti-TNF-α antibody included in a diagnostic kit is immobilized on a solid surface, or a solid surface (e.g., a slide) on which the antibody can be immobilized is included in the kit. The relative amounts of the various reagents can be varied widely to provide for concentrations in solution of the reagents which substantially optimize the sensitivity of the assay. In a specific embodiment, the antibody and one or more reagents can be provided (individually or combined) as dry powders, usually lyophilized, including excipients which on dissolution will provide a reagent solution having the appropriate concentration.

8. EXAMPLE 1

Identification of Deimmunized Variants of D2E7

8.1 Materials & Methods

8.1.1 Peptides

Peptides were synthesized using a multi-pin format by Mimotopes (Adelaide, Australia). The sequences of the D2E7 light and heavy chain V regions were synthesized as 15-mer peptides overlapping by 12 amino acids (FIG. 1 and Table 1) for a total of 69 peptides. Peptides arrived lyophilized and were re-suspended in DMSO (Sigma-Aldrich) at approximately 1-2 mg/mL. Stock peptides were kept frozen at −20° C.

8.1.2 Human Peripheral Blood Mononuclear Cells

Community donor buffy coat products were purchased from the Stanford Blood Center, Palo Alto, Calif. Buffy coat material was diluted 1:1 (v:v) with DPBS containing no calcium or magnesium. Diluted buffy coat material (25-35 mL) was underlayed in 50 mL conical centrifuge tubes (Sarsted or Costar) with 12.5 mL mL of FicollPaque-PLUS (GE Healthcare). The samples were centrifuged at 900 g for 30 minutes at room temperature. Peripheral blood mononuclear cells (PBMC) were collected from the interface. DPBS was added to bring the final volume to 50 mLmL and the cells were centrifuged at 350 g for 5 minutes. Pelleted cells were resuspended in DPBS and counted.

8.1.3 Dendritic Cells

For isolation of dendritic cells, T75 culture flasks (Costar) were seeded with $10^8$ freshly isolated PBMC in a total volume of 30 mL AIM V media (Invitrogen). Excess PBMC were frozen at −80° C. in 90% fetal calf serum (FCS), 10% DMSO at $5 \times 10^7$ cells/ml. T75 flasks were incubated at 37° C. in 5% $CO_2$ for 2 hours. Nonadherent cells were removed, and the adherent monolayer was washed with DPBS. To differentiate dendritic cells from monocytes, 30 mL of AIM V media containing 800 units/mL of GM-CSF (R and D Systems) and 500 units/mL IL-4 (R and D Systems) were added. Flasks were incubated for 5 days. On day 5 IL-1α (Endogen) and TNF-α (Endogen) were added to 50 pg/mL and 0.2 ng/ml. Flasks were incubated for two more days. On day 7, dendritic cells were collected by the addition of 3 mL of 100 mM EDTA containing 0.5 to 1.0 mg Mitomycin C (Sigma-Aldrich) for a final concentration of 10 mM EDTA and 16.5 to 33 μg/mL Mitomycin C. Alternatively, dendritic cells can be irradiated with 4,000 rads for fixation. Flasks were incubated an additional hour at 37° C. and 5% $CO_2$. Dendritic cells were collected, and washed in AIM V media 2-3 times.

8.1.4 Cell Culture

On day 7, previously frozen autologous PBMC were thawed quickly in a 37° C. water bath. Cells were immediately diluted into DPBS or AIM V media and centrifuged at 350 g for 5 minutes. CD4+ cells were enriched by negative selection using magnetic beads (Easy-Sep CD4+ kit, Stem Cell Technologies). Autologous CD4+ T cells and dendritic cells were cocultured at $2\times10^5$ CD4+ T cells per $2\times10^4$ dendritic cells per well in 96 well round bottomed plates (Costar 9077). Peptides were added at approximately 5 µg/mL. Control wells contained the DMSO (Sigma) vehicle alone at 0.25% v:v. Positive control wells contained DMSO at 0.25% and tetanus toxoid (List Biologicals or CalBioChem) at 1 µg/mL. Cultures were incubated for 5 days. On day 5, 0.25 µCi per well of tritiated thymidine (Amersham or GE Healthcare) was added. Cultures were harvested on day 6 to filtermats using a Packard Filtermate Cell harvester. Scintillation counting was performed using a Wallac MicroBeta 1450 scintillation counter (Perkin Elmer).

8.1.5 Data Analyses

Average background CPM values were calculated by averaging individual results from 6 to 12 replicates. The CPM values of the four positive control wells were averaged. Replicate or triplicate wells for each peptide were averaged. Stimulation index values for the positive control and the peptide wells were calculated by dividing the average experimental CPM values by the average control values. In order to be included in the dataset, a stimulation index of greater than 3.0 in the tetanus toxoid positive control wells was required. A response was noted for any peptide resulting in a stimulation index of 2.95 or greater. Peptides were tested using peripheral blood samples from a group of 81 donors. Responses to all peptides were compiled. For each peptide tested, the percentage of the donor set that responded with a stimulation index of 2.95 or greater was calculated. In addition, the average stimulation index for all donors was calculated.

8.1.6 HLA Genotype Analysis

HLA DRB1 and HLA DQB1 alleles were determined for each donor using the commercially available Dynal RELI typing kits (Invitrogen, UK). Low stringency SSO results are reported. HLA associations were determined for responsiveness to any given peptide using a Chi-squared analysis (one degree of freedom). Where an allele was present in both of the responder and non-responder populations, a relative risk value was reported.

8.1.7 Competition ELISA of D2E7 Variant Antibodies

TNF-α was adhered onto a microwell plate, by contacting the plate with a solution of TNF-α at a concentration of 1 µg/mL in PBS over night at 4° C. The plate was washed in 0.1% Tween 20 in PBS and blocked in Superblock (Thermo Scientific, Rockford, Ill.). A mixture of sub-saturating amount of biotinylated D2E7 (80 ng/mL) and unlabeled D2E7 (the "reference" antibody) or competing anti-TNF-α antibody (the "test" antibody) antibody in serial dilution (at a concentration of 2.8 µg/mL, 8.3 µg/mL, or 25 µg/mL) in ELISA buffer (e.g., 1% BSA and 0.1% Tween 20 in PBS) was added to wells and plates were incubated for 1 hour with gentle shaking. The plate was washed, 1 µg/mL HRP-conjugated Streptavidin diluted in ELISA buffer was added to each well and the plates incubated for 1 hour. Plates were washed and bound antibodies were detected by addition of TMB (Biofx Laboratories Inc., Owings Mills, Md.). The reaction was terminated by addition of stop buffer (e.g., Bio FX Stop Reagents, Biofx Laboratories Inc., Owings Mills, Md.) and the absorbance was measured at 650 nm using microplate reader (e.g., VERSAmax, Molecular Devices, Sunnyvale, Calif.). The $IC_{50}$ values were calculated for each antibody. The experiment was performed three times, and average results are shown as a percent of the parent antibody binding result.

8.1.8 Bioassay $3\times10^4$ murine L929 cells were plated into individual wells of a flat bottomed 96-well microtiter plate. The cells were incubated overnight at 37° C. in a humidified 5% $CO_2$ incubator. The next day, serial dilutions of the anti-TNF-α antibody (e.g., 0.712 µg/mL, 0.949 µg/mL, 1.27 µg/mL, 1.69 µg/mL, 2.25 µg/mL or 3 µg/mL) were prepared in 25 µL, of serum-free medium and added to cells (such that the final concentration in 150 µL, culture was 119 ng/mL, 158 ng/mL, 211 ng/mL, 282 ng/mL, 375 ng/mL or 500 ng/mL). After a 2-hour incubation at 37° C. in 5% $CO_2$, 25 µL of a 240 ng/mL solution of TNF-α were added, for a final concentration of 40 ng/mL, and the cells were further incubated for 48 hours at 37° C. in 5% $CO_2$. The wells were scored for cytotoxicity as compared to control plates, which treated with TNF-α but incubated with an isotype control antibody or with the parent antibody, D2E7, using a CellTiter-Blue viability assay (Promega, Madison, Wis.). $IC_{50}$ values were determined and expressed as percent of the parental D2E7 result.

8.1.9 Kinetic Analysis of D2E7 Variants by BIAcore

Binding affinities of anti-TNF-α antibodies were measured by using a BIAcore 2000 and 3000 surface plasmon resonance system (BIAcore, GE Healthcare, Piscataway, N.J.). Polyclonal goat anti-human Fc antibody (Jackson Immunoresearch) was first immobilized to the biosensor surface using standard BIAcore amine coupling reagents (N-ethyl-N'-dimethylamino-propylcarbodiimide, EDC; N-hydroxysuccinimide, NHS; and ethanolamine HCl, pH 8.5), followed by the capture of anti-TNF-α antibodies (D2E7 and D2E7 variants) on parallel surfaces at a low flow rate of 5 µL/min. RL was kept low to achieve a low Rmax of 25-60 RU. No capture of the antibody was made on the reference surface to serve as a negative control. Subsequently, TNF-α was injected to all flow cells at a flow rate of 80 µL/min for three minutes to monitor association followed by a 30-minute flow of HBS-P running buffer (10 mM HEPES, 150 mM sodium chloride, 0.005% P-20, pH 7.4) to monitor the dissociation phase. At each cycle, TNF-α (R&D systems, Minneapolis, Minn.), in 6 different concentrations of TNF ranging between 0 nM and 128 and at four-fold increments, was injected over the surface. The surface was regenerated with 1.5% $H_3PO_4$ at a flow rate of 100 µL/min in two brief pulses at the end of each cycle.

The binding kinetics of each TNF-α and antibody pair were calculated from a global analysis of sensorgram data collected from the different concentrations of TNF-α using the BIAevaluate program. Double referencing was applied in each analysis to eliminate background responses from the reference surface and buffer only control (0 nM of TNF-α). The dissociation constants ($K_D$), the association rate constants ($k_{on}$) and the dissociation rate constants ($k_{off}$) of each binding pair was obtained by simultaneously fitting the association and dissociation phases of the sensorgram using the 1:1 Langmuir binding with mass transfer model. Each set of experiments was performed 3 separate times.

8.2 Results

8.2.1 Identification of CD4+ T Cell Epitopes in the D2E7 VH and VL Regions

CD4+ T cell epitope peptides were identified by an analysis of the percent responses to the peptides within the set of 81 donors. The average percent response and standard deviation were calculated for all peptides tested describing the D2E7 heavy chain and light chain. A response rate greater than or equal to the average background response plus three standard deviations was considered a potential CD4+ T cell epitope. For the D2E7 light chain V region, 32 peptides were tested (FIG. 2) which resulted in an average background percent response of 5.09+3.53%. Three standard deviations above background was determined to be 15.68%. One peptide at position 8 displayed this level of response in the D2E7 light chain peptide dataset, with a response rate of 17.28% (FIG. 2). In addition, the peptide at position 11 displayed a very high response rate of 12.35%. For the D2E7 heavy chain V region, 37 peptides were tested (FIG. 3). The average background percent response was 2.64+2.04%. Three standard deviations above background was 8.78%. One peptide within the D2E7 heavy chain dataset, #20, achieved a percent response of 8.64% (FIG. 3).

The average stimulation index was calculated for all peptides in the dataset. Light chain peptide #8 had a high average stimulation index of 1.97+0.08 s.e.m. The peptide at position #11 returned an average stimulation index of 1.63+0.32 s.e.m. Peptide #27 in the light chain dataset had an average SI of 1.83. This is due to a single donor with an unusually high stimulation index of 29 to this peptide. Heavy chain peptide #20 had an average stimulation index value of 1.34+0.05 s.e.m. All of these values are significantly higher than the average stimulation index for all peptides in the two datasets (1.02+0.02 for all 68 heavy chain and light chain peptides).

These data indicate that there are two major CD4+ T cell epitope regions in D2E7 (Table 2). In the VH region, an epitope is found at peptide position 20 that encompasses the junction of framework 2 and CDR2. In Table 2, the CDR-derived amino acids are underlined. In the light chain, a large region that can contain more than one CD4+ T cell epitope includes peptides #8 and #11. These peptides span a section of framework 1, CDR1 and framework 2 of the light chain.

8.2.2 HLA Associations with Responses to the VL Epitope Peptides

The HLA class II genotypes of all 81 donors in the peptide dataset were determined using a low-stringency SSO PCR-based method. Associations between the presence of a particular HLA allele and responses to the two VL peptides were determined by chi squared analysis. Fischer P values and relative risks were determined for all HLA types and both peptides (Table 3). There were no significant correlations between any HLA DR or DQ type and a response to VL peptide #8 (T22-Y36). This result suggests that the peptide is capable of binding to HLA class II molecules in a broadly promiscuous manner. CD4+ T cell proliferative responses to the VL peptide #11 (N31-K45) were tightly associated with the presence of HLA-DQ2 (p=0.003; relative risk=7.7). As HLA-DR3 is in linkage disequilibrium with HLA-DQ2, the association between a response to this peptide and HLA-DR3 was present but did not reach statistical significance (p=0.10; relative risk 3.3). In addition to HLA-DQ2, as association was found between HLA-DR12 and a response to N31-K45 (p=0.03; relative risk 5.2). The HLA responses to the VH peptide #20 were not tested as there were too few total responders. Since the responders to the two VL peptides were discrete it can be concluded that they represent two separate peptide epitopes. Therefore, the D2E7 VH and VL region contains three prominent peptide epitope regions.

8.2.3 Identification of Reduced Immunogenicity Variants
  Alanine Scan Modifications:

A twenty-one amino acid sequence of the D2E7 light chain encompasses the epitopes at T22-Y36 and N31-K45. The twenty one amino acid sequence selected was C23-K45. Alanine modifications were incorporated at each amino acid (Table 4). A set of 99 donors was tested with the variant peptides (FIG. 4). The parent 21-mer was created 4 times within the peptide set. These four replicates serve as a control for the reproducibility of the assay. The average parent peptide response was 8.3%, with a CV % of 30%. Therefore, variant peptides with an average percent of less than 5.8% could be considered to have a reduced rate of response. The most reduced variants were C23A (2.02%) and P40A (3.03%, see FIG. 4). The cysteine at position 23 is invariant, and is therefore not a good candidate for modification in the whole protein. Due to the unique nature of proline residues a modification of this residue is also not likely to yield a functional variant antibody. The third candidate would be Y32A (4.04%). Additionally, there are a number of variants that resulted in an average response rate of 5.05%. These changes could also be effective but would need to be tested as whole protein molecules for both reduced immunogenicity and functional activity.

A set of alanine-modified peptides based on the sequence of the D2E7 VH epitope peptide were also tested (data not shown). The response rate of the parent unmodified peptide in the replicate test was very low. Therefore this peptide was no longer studied.

Antigen Binding Study:

The CDR-L1 region of the D2E7 antibody was subjected to comprehensive mutational analysis. Based on antigen-binding studies performed in conjunction with the mutational analyses, a set of candidate amino acid substitutions within the CDR-L1 region was identified that did not significantly reduce the affinity of the antibody to TNF-α (Table 5). Several variant antibodies containing the candidate CDR-L1 substitutions were analyzed using BIAcore and ELISA (Table 6). Peptides were generated containing amino acid modifications within the CDR-L1 region that had the property of altering the amino acid sequence while retaining the affinity of the overall antibody molecule (Table 7). The modified epitope peptides were tested as single amino-acid modifications, or as double modifications. The double modifications contained a glutamine or a glycine at position 32, or a serine or glycine at position 34. A total of 79 peptides were tested including two syntheses of the parent 21-mer peptide. A total of 102 donors were tested with the variant peptides and the results are shown in FIG. 5. The average percent response of the parent peptides was 10.3+2.1%. For a percent response rate to be less than 3 standard deviations from the parent the response rate would be less than 4%. The average stimulation index for the parent peptides was 1.49+0.15. For a stimulation index to reach three standard deviations below the parent response it would be 1.03 or lower.

Subsequent affinity measurements of the Y32G and Y32Q mutations showed that this amino acid modification had a negative impact on antigen binding. Therefore, all peptides carrying this modification were removed from the analysis. A total of 10 peptides were selected for further study. All selected peptides had a response rate less than 4%. However, none of the peptides demonstrated stimulation indexes 3 standard deviations below the average parent response (Table 8).

8.2.4 Affinity and Bioactivity Testing of Modified D2E7 Variant Antibodies

Ten variant D2E7 VL region constructs were cloned along with the unmodified VH region into a human $IgG_1$-containing plasmid, expressed in 293T/17 cell lines by transient transfection, and antibodies purified by Protein A or Protein G affinity. The purified antibodies were tested for TNF-α binding in a competition ELISA assay. All ten variants competed for TNF-α binding with the unmodified D2E7 antibody. However, there was a range of affinities displayed, from approximately equivalent affinity of the Q27R+A34S variant, to a 10× reduction in affinity of the N31S+A34S variant (FIG. 6).

A TNF-α toxicity bioassay was performed. L292 cells were seeded into 96 well plates, and a constant concentration of TNF-α was added to the culture medium. The variant antibodies were titrated into the medium. An $EC_{50}$ value was determined for each variant (Table 9). Similarly, the variant Q27R+A34S displayed an $EC_{50}$ value approximately equivalent to the parent D2E7 antibody.

Finally, affinity of the antibodies for TNF-α was determined by BIAcore analysis (Table 10). Of the ten variants tested, the Q27H+A34S, Q27R+A34S and G28S+A34S variants all displayed association and dissociation rates similar to D2E7. The final affinity values for the variants were in the 130 pM range as compared to D2E7 with a measured affinity in these experiments of 114 pM.

9. EXAMPLE 2

Identification of Variants of D2E7 with Increased Affinity to TNF-α

The D2E7 antibody was subjected to comprehensive mutational analysis to identify mutants that had increased affinity to TNF-α as compared to D2E7. The increased affinity of candidate mutants to TNF-α was analyzed by ELISA and BIAcore to confirm their characteristics as compared to D2E7.

9.1 Materials & Methods 9.1.1 Competition ELISA

Competition ELISA assays were done as described in Section 8.1.7. ELISA was repeated twice and average fold improvement in $IC_{50}$ is shown as WT/x.

9.1.2 BIAcore

BIAcore assays were done as described in Section 8.1.9.

9.2 Results

CDR variants of D2E7 that had improved $K_D$ (as measured by BIAcore), improved ability to compete in ELISA, or both relative to D2E7 are shown in Tables 12 and 25.

10. SPECIFIC EMBODIMENTS

Citation of References

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating an immune disorder selected from the group consisting of rheumatoid arthritis, juvenile idiopathic arthritis, psoriatic arthritis, ankylosing spondylitis, Crohn's disease, ulcerative colitis, and plaque psoriasis, comprising administering to a human patient in need thereof a therapeutically effective amount of an anti-TNF-α antibody or anti-TNF-α binding fragment thereof which:
   (a) specifically binds to human TNF-α; and
   (b) comprises a heavy chain amino acid sequence having at least 95% sequence identity to SEQ ID NO:2 and a light chain amino acid sequence having at least 95% sequence identity to SEQ ID NO:4,
   wherein the heavy and light chain amino acid sequences comprise one or more amino acid substitutions or combinations of amino acid substitutions selected from:
   (1) the CDR-L1 substitutions R7Q; A11S; R7Q+A11S; N8T; N8T+A11S; I6T; A11G; I6T+A11G; Q4G; Q4G+A11S; Q4G+A11G; Q4H; Q4H+A11S; Q4R+A11S; G5S+A11S; N8S+A11S; I6T+A11S; and N8T+A11G;
   (2) the CDR-L2 substitutions S3K or S3R; T4H, T4Q, T4F, T4W or T4Y; L5R or L5K; and Q6R;
   (3) the CDR-H1 substitutions: Y2H and A3G; and
   (4) the CDR-H2 substitution: T3N, wherein the numbering of the amino acids corresponds to the positions in the CDRs of D2E7.

2. The method of claim 1, wherein the heavy and light chain amino acid sequences of the anti-TNFα antibody or anti-TNF-α binding fragment thereof comprise at least one amino acid substitution selected from S3K or S3R in CDR-L2; T4H, T4Q, T4F, T4W or T4Y in CDR-L2; L5R or L5K in CDR-L2; Q6R in CDR-L2; Y2H in CDR-H1; A3G in CDR-H1 and T3N in CDR-H2.

3. The method of claim 1, wherein the heavy and light chain amino acid sequences comprise at least one amino acid substitution selected from T4F, T4W or T4Y in CDR-L2; L5R or L5K in CDR-L2; Q6R in CDR-L2; Y2H in CDR-H1; A3G in CDR-H1 and T3N in CDR-H2.

4. The method of claim 1, wherein the heavy and light chain amino acid sequences comprise at least one amino acid substitution selected from R7Q in CDR-L1; A11S in CDR-L1; R7Q+A11S in CDR-L1; N8T in CDR-L1; N8T+A11S in CDR-L1; I6T in CDR-L1; A11G in CDR-L1; I6T+A11G in CDR-L1; Q4G in CDR-L1; Q4G+A11S in CDR-L1; Q4G+A11G in CDR-L1; Q4H in CDR-L1; Q4H+A11S in CDR-L1; Q4R+A11S in CDR-L1; G5S+A11S in CDR-L1; N8S+A11S in CDR-L1; I6T+A11S in CDR-L1; and N8T+A11G in CDR-L1.

5. The method of claim 1, wherein the anti-TNF-α antibody or anti-TNF-α binding fragment is a human or humanized antibody, or binding fragment of a human or humanized antibody, respectively.

6. The method of claim 1, wherein the anti-TNF-α antibody or anti-TNF-α binding fragment is an IgG.

7. The method of claim 1, wherein the anti-TNF-α antibody or anti-TNF-α binding fragment is an IgG$_1$.

8. The method of claim 1, wherein the anti-TNF-α antibody or anti-TNF-α binding fragment has the heavy chain framework sequences of the V$_H$ sequence of SEQ ID NO:2 and the light chain framework sequences of the V$_L$ sequence of SEQ ID NO:4.

9. The method of claim 1, wherein the anti-TNF-α antibody or anti-TNF-α binding fragment is a bispecific antibody or a TNF-α binding fragment of a bispecific antibody.

10. The method of claim 9, wherein said bispecific antibody is specific to TNF-α and another pro-inflammatory cytokine.

11. The method of claim 10, wherein said pro-inflammatory cytokine is lymphotoxin, interferon-γ, or interleukin-1.

12. The method of claim 1, wherein the anti-TNF-α antibody or anti-TNF-α binding fragment has the CDR-L1 substitutions Q4R+A11S.

13. The method of claim 1, wherein the anti-TNF-α antibody or anti-TNF-α binding fragment has the CDR-L1 substitutions Q4G+A11G.

14. The method of claim 1, wherein the anti-TNF-α antibody or anti-TNF-α binding fragment has the CDR-L1 substitutions Q4H+A11S.

15. The method of claim 1, wherein the anti-TNF-α antibody or anti-TNF-α binding fragment has the CDR-L1 substitutions G5S+A11S.

16. The method of claim 1, wherein the anti-TNF-α antibody or anti-TNF-α binding fragment has the CDR-L2 substitution S3K.

17. The method of claim 1, wherein the anti-TNF-α antibody or anti-TNF-α binding fragment has the CDR-L2 substitution S3R.

18. The method of claim 1, wherein the anti-TNF-α antibody or anti-TNF-α binding fragment has the CDR-L2 substitution T4H.

19. The method of claim 1, wherein the anti-TNF-α antibody or anti-TNF-α binding fragment has the CDR-L2 substitution T4Q.

20. The method of claim 1, wherein the anti-TNF-α antibody or anti-TNF-α binding fragment has the CDR-L2 substitution T4F.

21. The method of claim 1, wherein the anti-TNF-α antibody or anti-TNF-α binding fragment has the CDR-L2 substitution T4W.

22. The method of claim 1, wherein the anti-TNF-α antibody or anti-TNF-α binding fragment has the CDR-L2 substitution T4Y.

23. The method of claim 1, wherein the anti-TNF-α antibody or anti-TNF-α binding fragment has the CDR-L2 substitution L5R.

24. The method of claim 1, wherein the anti-TNF-α antibody or anti-TNF-α binding fragment has the CDR-L2 substitution L5K.

25. The method of claim 1, wherein the anti-TNF-α antibody or anti-TNF-α binding fragment has the CDR-L2 substitution Q6R.

26. The method of claim 1, wherein the anti-TNF-α antibody or anti-TNF-α binding fragment has the CDR-H1 substitution Y2H.

27. The method of claim 1, wherein the anti-TNF-α antibody or anti-TNF-α binding fragment has the CDR-H1 substitution A3G.

28. The method of claim 1, wherein the anti-TNF-α antibody or anti-TNF-α binding fragment has the CDR-H1 substitution T3N.

29. The method of claim 1, wherein the anti-TNF-α antibody or anti-TNF-α binding fragment is conjugated to an effector moiety or a label.

30. The method of claim 1, wherein the immune disorder is rheumatoid arthritis.

31. The method of claim 1, wherein the immune disorder is juvenile idiopathic arthritis.

32. The method of claim 1, wherein the immune disorder is psoriatic arthritis.

33. The method of claim 1, wherein the immune disorder is ankylosing spondylitis.

34. The method of claim 1, wherein the immune disorder is Crohn's disease.

35. The method of claim 1, wherein the immune disorder is ulcerative colitis.

36. The method of claim 1, wherein the immune disorder is plaque psoriasis.

* * * * *

UNITED STATES PATENT AND TRADEMARK OFFICE
CERTIFICATE OF CORRECTION

PATENT NO.         : 9,315,573 B2                         Page 1 of 1
APPLICATION NO.    : 14/194090
DATED              : April 19, 2016
INVENTOR(S)        : Fiona A. Harding et al.

It is certified that error appears in the above-identified patent and that said Letters Patent is hereby corrected as shown below:

In the claims

In column 191, claim 2, line 2, please change "anti-TNFα" to -- anti-TNF-α --.

Signed and Sealed this
Twelfth Day of July, 2016

Michelle K. Lee
*Director of the United States Patent and Trademark Office*

SEQUENCE LISTING

```
<160> NUMBER OF SEQ ID NOS: 392

<210> SEQ ID NO 1
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
gcggactctg tggagggccg attcaccatc tccagagaca acgccaagaa ctccctgtat     240
ctgcaaatga acagtctgag agctgaggat acggccgtat attactgtgc gaaagtctcg     300
taccttagca ccgcgtcctc ccttgactat tggggccaag gtaccctggt caccgtctcg     360
agt                                                                  363

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
 50                  55                  60

Glu Gly Arg Phe Thr Ile Ser Arg Pro Arg Thr Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                               321

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 5
<211> LENGTH: 5
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 5

Asp Tyr Ala Met His
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Ser Tyr Leu Ser Thr Ala Ser Ser Leu Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser Gln Gly Ile Arg Asn Tyr Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Ser Thr Leu Gln Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Arg Tyr Asn Arg Ala Pro Tyr Thr
1               5

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Val Gln Leu Val Glu Ser Gly Gly Gly Leu Val Gln Pro Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Val Glu Ser Gly Gly Gly Leu Val Gln Pro Gly Arg Ser Leu
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gly Gly Gly Leu Val Gln Pro Gly Arg Ser Leu Arg Leu Ser
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Val Gln Pro Gly Arg Ser Leu Arg Leu Ser Cys Ala Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Pro Gly Arg Ser Leu Arg Leu Ser Cys Ala Ala Ser Gly Phe
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Leu Arg Leu Ser Cys Ala Ala Ser Gly Phe Thr Phe Asp
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Leu Ser Cys Ala Ala Ser Gly Phe Thr Phe Asp Asp Tyr Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Ala Ala Ser Gly Phe Thr Phe Asp Asp Tyr Ala Met His Trp
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Gly Phe Thr Phe Asp Asp Tyr Ala Met His Trp Val Arg Gln
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Phe Asp Asp Tyr Ala Met His Trp Val Arg Gln Ala Pro Gly
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Tyr Ala Met His Trp Val Arg Gln Ala Pro Gly Lys Gly Leu
1               5                   10                  15

<210> SEQ ID NO 22
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met His Trp Val Arg Gln Ala Pro Gly Lys Gly Leu Glu Trp Val
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Arg Gln Ala Pro Gly Lys Gly Leu Glu Trp Val Ser Ala Ile
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Pro Gly Lys Gly Leu Glu Trp Val Ser Ala Ile Thr Trp Asn
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Gly Leu Glu Trp Val Ser Ala Ile Thr Trp Asn Ser Gly His
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Trp Val Ser Ala Ile Thr Trp Asn Ser Gly His Ile Asp Tyr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ala Ile Thr Trp Asn Ser Gly His Ile Asp Tyr Ala Asp Ser
```

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Trp Asn Ser Gly His Ile Asp Tyr Ala Asp Ser Val Glu Gly
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gly His Ile Asp Tyr Ala Asp Ser Val Glu Gly Arg Phe Thr
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Asp Tyr Ala Asp Ser Val Glu Gly Arg Phe Thr Ile Ser Arg
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Asp Ser Val Glu Gly Arg Phe Thr Ile Ser Arg Asp Asn Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Glu Gly Arg Phe Thr Ile Ser Arg Asp Asn Ala Lys Asn Ser
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 33

Arg Phe Thr Ile Ser Arg Asp Asn Ala Lys Asn Ser Leu Tyr Leu
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Ser Arg Asp Asn Ala Lys Asn Ser Leu Tyr Leu Gln Met Asn
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Asn Ala Lys Asn Ser Leu Tyr Leu Gln Met Asn Ser Leu Arg
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Asn Ser Leu Tyr Leu Gln Met Asn Ser Leu Arg Ala Glu Asp
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Tyr Leu Gln Met Asn Ser Leu Arg Ala Glu Asp Thr Ala Val
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Met Asn Ser Leu Arg Ala Glu Asp Thr Ala Val Tyr Tyr Cys
1               5                   10                  15

<210> SEQ ID NO 39

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Leu Arg Ala Glu Asp Thr Ala Val Tyr Tyr Cys Ala Lys Val
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Glu Asp Thr Ala Val Tyr Tyr Cys Ala Lys Val Ser Tyr Leu
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Ala Val Tyr Tyr Cys Ala Lys Val Ser Tyr Leu Ser Thr Ala
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Tyr Cys Ala Lys Val Ser Tyr Leu Ser Thr Ala Ser Ser Leu
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Lys Val Ser Tyr Leu Ser Thr Ala Ser Ser Leu Asp Tyr Trp
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44
```

Ser Tyr Leu Ser Thr Ala Ser Ser Leu Asp Tyr Trp Gly Gln Gly
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Thr Ala Ser Ser Leu Asp Tyr Trp Gly Gln Gly Thr Leu Val
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Ser Leu Asp Tyr Trp Gly Gln Gly Thr Leu Val Thr Val Ser
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Leu Asp Tyr Trp Gly Gln Gly Thr Leu Val Thr Val Ser Ser
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Ile Gln Met Thr Gln Ser Pro Ser Ser Leu Ser Ala Ser Val
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Thr Gln Ser Pro Ser Ser Leu Ser Ala Ser Val Gly Asp Arg
1               5                   10                  15

<210> SEQ ID NO 50
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 50

Ser Pro Ser Ser Leu Ser Ala Ser Val Gly Asp Arg Val Thr Ile
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Leu Ser Ala Ser Val Gly Asp Arg Val Thr Ile Thr Cys Arg
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Ser Val Gly Asp Arg Val Thr Ile Thr Cys Arg Ala Ser Gln
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Asp Arg Val Thr Ile Thr Cys Arg Ala Ser Gln Gly Ile Arg
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Thr Ile Thr Cys Arg Ala Ser Gln Gly Ile Arg Asn Tyr Leu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Cys Arg Ala Ser Gln Gly Ile Arg Asn Tyr Leu Ala Trp Tyr
1               5                   10                  15
```

```
<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Ser Gln Gly Ile Arg Asn Tyr Leu Ala Trp Tyr Gln Gln Lys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Ile Arg Asn Tyr Leu Ala Trp Tyr Gln Gln Lys Pro Gly Lys
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asn Tyr Leu Ala Trp Tyr Gln Gln Lys Pro Gly Lys Ala Pro Lys
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Trp Tyr Gln Gln Lys Pro Gly Lys Ala Pro Lys Leu Leu Ile
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Gln Lys Pro Gly Lys Ala Pro Lys Leu Leu Ile Tyr Ala Ala
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61
```

Pro Gly Lys Ala Pro Lys Leu Leu Ile Tyr Ala Ala Ser Thr Leu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Pro Lys Leu Leu Ile Tyr Ala Ala Ser Thr Leu Gln Ser Gly
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Leu Ile Tyr Ala Ala Ser Thr Leu Gln Ser Gly Val Pro Ser
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Tyr Ala Ala Ser Thr Leu Gln Ser Gly Val Pro Ser Arg Phe Ser
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Thr Leu Gln Ser Gly Val Pro Ser Arg Phe Ser Gly Ser Gly
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Ser Gly Val Pro Ser Arg Phe Ser Gly Ser Gly Ser Gly Thr
1               5                   10                  15

<210> SEQ ID NO 67
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 67

Val Pro Ser Arg Phe Ser Gly Ser Gly Ser Gly Thr Asp Phe Thr
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Phe Ser Gly Ser Gly Ser Gly Thr Asp Phe Thr Leu Thr Ile
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Ser Gly Ser Gly Thr Asp Phe Thr Leu Thr Ile Ser Ser Leu
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Gly Thr Asp Phe Thr Leu Thr Ile Ser Ser Leu Gln Pro Glu
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Phe Thr Leu Thr Ile Ser Ser Leu Gln Pro Glu Asp Val Ala
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Thr Ile Ser Ser Leu Gln Pro Glu Asp Val Ala Thr Tyr Tyr
1               5                   10                  15
```

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Ser Ser Leu Gln Pro Glu Asp Val Ala Thr Tyr Tyr Cys Gln Arg
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Gln Pro Glu Asp Val Ala Thr Tyr Tyr Cys Gln Arg Tyr Asn Arg
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Asp Val Ala Thr Tyr Tyr Cys Gln Arg Tyr Asn Arg Ala Pro Tyr
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Asp Val Ala Thr Tyr Tyr Cys Gln Arg Tyr Asn Arg Ala Pro Tyr
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Thr Tyr Tyr Cys Gln Arg Tyr Asn Arg Ala Pro Tyr Thr Phe Gly
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 78

Cys Gln Arg Tyr Asn Arg Ala Pro Tyr Thr Phe Gly Gln Gly Thr
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Tyr Asn Arg Ala Pro Tyr Thr Phe Gly Gln Gly Thr Lys Val Glu
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Ala Pro Tyr Thr Phe Gly Gln Gly Thr Lys Val Glu Ile Lys
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ile Asp Tyr Ala Asp Ser Val Glu Gly Arg Phe Thr Ile Ser Arg
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Cys Arg Ala Ser Gln Gly Ile Arg Asn Tyr Leu Ala Trp Tyr
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asn Tyr Leu Ala Trp Tyr Gln Gln Lys Pro Gly Lys Ala Pro Lys
1               5                   10                  15

<210> SEQ ID NO 84
<211> LENGTH: 23
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 84

Cys Arg Ala Ser Gln Gly Ile Arg Asn Tyr Leu Ala Trp Tyr Gln Gln
1               5                   10                  15

Lys Pro Gly Lys Ala Pro Lys
            20

<210> SEQ ID NO 85
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Arg Ala Ser Gln Gly Ile Arg Asn Tyr Leu Ala Trp Tyr Gln Gln
1               5                   10                  15

Lys Pro Gly Lys Ala Pro Lys
            20

<210> SEQ ID NO 86
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Ala Ala Ser Gln Gly Ile Arg Asn Tyr Leu Ala Trp Tyr Gln Gln
1               5                   10                  15

Lys Pro Gly Lys Ala Pro Lys
            20

<210> SEQ ID NO 87
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Arg Ala Ser Gln Gly Ile Arg Asn Tyr Leu Ala Trp Tyr Gln Gln
1               5                   10                  15

Lys Pro Gly Lys Ala Pro Lys
            20

<210> SEQ ID NO 88
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Cys Arg Ala Ala Gln Gly Ile Arg Asn Tyr Leu Ala Trp Tyr Gln Gln
1               5                   10                  15

Lys Pro Gly Lys Ala Pro Lys
```

20

<210> SEQ ID NO 89
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Cys Arg Ala Ser Ala Gly Ile Arg Asn Tyr Leu Ala Trp Tyr Gln Gln
1               5                   10                  15

Lys Pro Gly Lys Ala Pro Lys
            20

<210> SEQ ID NO 90
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Cys Arg Ala Ser Gln Ala Ile Arg Asn Tyr Leu Ala Trp Tyr Gln Gln
1               5                   10                  15

Lys Pro Gly Lys Ala Pro Lys
            20

<210> SEQ ID NO 91
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Cys Arg Ala Ser Gln Gly Ala Arg Asn Tyr Leu Ala Trp Tyr Gln Gln
1               5                   10                  15

Lys Pro Gly Lys Ala Pro Lys
            20

<210> SEQ ID NO 92
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Cys Arg Ala Ser Gln Gly Ile Ala Asn Tyr Leu Ala Trp Tyr Gln Gln
1               5                   10                  15

Lys Pro Gly Lys Ala Pro Lys
            20

<210> SEQ ID NO 93
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 93

Cys Arg Ala Ser Gln Gly Ile Arg Ala Tyr Leu Ala Trp Tyr Gln Gln
1               5                   10                  15

Lys Pro Gly Lys Ala Pro Lys
            20

<210> SEQ ID NO 94
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Cys Arg Ala Ser Gln Gly Ile Arg Asn Ala Leu Ala Trp Tyr Gln Gln
1               5                   10                  15

Lys Pro Gly Lys Ala Pro Lys
            20

<210> SEQ ID NO 95
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Cys Arg Ala Ser Gln Gly Ile Arg Asn Tyr Ala Ala Trp Tyr Gln Gln
1               5                   10                  15

Lys Pro Gly Lys Ala Pro Lys
            20

<210> SEQ ID NO 96
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Cys Arg Ala Ser Gln Gly Ile Arg Asn Tyr Leu Ala Trp Tyr Gln Gln
1               5                   10                  15

Lys Pro Gly Lys Ala Pro Lys
            20

<210> SEQ ID NO 97
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Cys Arg Ala Ser Gln Gly Ile Arg Asn Tyr Leu Ala Ala Tyr Gln Gln
1               5                   10                  15

Lys Pro Gly Lys Ala Pro Lys
            20

<210> SEQ ID NO 98
<211> LENGTH: 23
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Cys Arg Ala Ser Gln Gly Ile Arg Asn Tyr Leu Ala Trp Ala Gln Gln
1               5                   10                  15

Lys Pro Gly Lys Ala Pro Lys
            20

<210> SEQ ID NO 99
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Cys Arg Ala Ser Gln Gly Ile Arg Asn Tyr Leu Ala Trp Tyr Ala Gln
1               5                   10                  15

Lys Pro Gly Lys Ala Pro Lys
            20

<210> SEQ ID NO 100
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Cys Arg Ala Ser Gln Gly Ile Arg Asn Tyr Leu Ala Trp Tyr Gln Ala
1               5                   10                  15

Lys Pro Gly Lys Ala Pro Lys
            20

<210> SEQ ID NO 101
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Arg Ala Ser Gln Gly Ile Arg Asn Tyr Leu Ala Trp Tyr Gln Gln
1               5                   10                  15

Ala Pro Gly Lys Ala Pro Lys
            20

<210> SEQ ID NO 102
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Cys Arg Ala Ser Gln Gly Ile Arg Asn Tyr Leu Ala Trp Tyr Gln Gln
1               5                   10                  15
```

Lys Ala Gly Lys Ala Pro Lys
            20

<210> SEQ ID NO 103
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Cys Arg Ala Ser Gln Gly Ile Arg Asn Tyr Leu Ala Trp Tyr Gln Gln
1               5                   10                  15

Lys Pro Ala Lys Ala Pro Lys
            20

<210> SEQ ID NO 104
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Cys Arg Ala Ser Gln Gly Ile Arg Asn Tyr Leu Ala Trp Tyr Gln Gln
1               5                   10                  15

Lys Pro Gly Ala Ala Pro Lys
            20

<210> SEQ ID NO 105
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Cys Arg Ala Ser Gln Gly Ile Arg Asn Tyr Leu Ala Trp Tyr Gln Gln
1               5                   10                  15

Lys Pro Gly Lys Ala Pro Lys
            20

<210> SEQ ID NO 106
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Cys Arg Ala Ser Gln Gly Ile Arg Asn Tyr Leu Ala Trp Tyr Gln Gln
1               5                   10                  15

Lys Pro Gly Lys Ala Ala Lys
            20

<210> SEQ ID NO 107
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 107

Cys Arg Ala Ser Gln Gly Ile Arg Asn Tyr Leu Ala Trp Tyr Gln Gln
1               5                   10                  15

Lys Pro Gly Lys Ala Pro Ala
            20

<210> SEQ ID NO 108
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Thr Cys Arg Ala Ser Gln Gly Ile Arg Asn Tyr Leu Ala Trp Tyr Gln
1               5                   10                  15

Gln Lys Pro Gly Lys Ala Pro Lys
            20

<210> SEQ ID NO 109
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Thr Cys Arg Ala Ser Asn Gly Ile Arg Asn Tyr Leu Ala Trp Tyr Gln
1               5                   10                  15

Gln Lys Pro Gly Lys Ala Pro Lys
            20

<210> SEQ ID NO 110
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Thr Cys Arg Ala Ser Gly Gly Ile Arg Asn Tyr Leu Ala Trp Tyr Gln
1               5                   10                  15

Gln Lys Pro Gly Lys Ala Pro Lys
            20

<210> SEQ ID NO 111
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Cys Arg Ala Ser His Gly Ile Arg Asn Tyr Leu Ala Trp Tyr Gln
1               5                   10                  15

Gln Lys Pro Gly Lys Ala Pro Lys
            20

<210> SEQ ID NO 112
```

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Cys Arg Ala Ser Ser Gly Ile Arg Asn Tyr Leu Ala Trp Tyr Gln
1               5                   10                  15

Gln Lys Pro Gly Lys Ala Pro Lys
            20

<210> SEQ ID NO 113
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Thr Cys Arg Ala Ser Arg Gly Ile Arg Asn Tyr Leu Ala Trp Tyr Gln
1               5                   10                  15

Gln Lys Pro Gly Lys Ala Pro Lys
            20

<210> SEQ ID NO 114
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Cys Arg Ala Ser Gln Ser Ile Arg Asn Tyr Leu Ala Trp Tyr Gln
1               5                   10                  15

Gln Lys Pro Gly Lys Ala Pro Lys
            20

<210> SEQ ID NO 115
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Thr Cys Arg Ala Ser Gln His Ile Arg Asn Tyr Leu Ala Trp Tyr Gln
1               5                   10                  15

Gln Lys Pro Gly Lys Ala Pro Lys
            20

<210> SEQ ID NO 116
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Cys Arg Ala Ser Gln Asn Ile Arg Asn Tyr Leu Ala Trp Tyr Gln
1               5                   10                  15
```

```
Gln Lys Pro Gly Lys Ala Pro Lys
            20

<210> SEQ ID NO 117
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Thr Cys Arg Ala Ser Gln Gly Val Arg Asn Tyr Leu Ala Trp Tyr Gln
1               5                   10                  15

Gln Lys Pro Gly Lys Ala Pro Lys
            20

<210> SEQ ID NO 118
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Thr Cys Arg Ala Ser Gln Gly Thr Arg Asn Tyr Leu Ala Trp Tyr Gln
1               5                   10                  15

Gln Lys Pro Gly Lys Ala Pro Lys
            20

<210> SEQ ID NO 119
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Thr Cys Arg Ala Ser Gln Gly Ile Gln Asn Tyr Leu Ala Trp Tyr Gln
1               5                   10                  15

Gln Lys Pro Gly Lys Ala Pro Lys
            20

<210> SEQ ID NO 120
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Thr Cys Arg Ala Ser Gln Gly Ile Arg Gly Tyr Leu Ala Trp Tyr Gln
1               5                   10                  15

Gln Lys Pro Gly Lys Ala Pro Lys
            20

<210> SEQ ID NO 121
<211> LENGTH: 24
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 121

Thr Cys Arg Ala Ser Gln Gly Ile Arg Thr Tyr Leu Ala Trp Tyr Gln
1               5                   10                  15

Gln Lys Phe Gly Lys Ala Pro Lys
            20

<210> SEQ ID NO 122
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Thr Cys Arg Ala Ser Gln Gly Ile Arg Ser Gln Leu Ala Trp Tyr Gln
1               5                   10                  15

Gln Lys Pro Gly Lys Ala Pro Lys
            20

<210> SEQ ID NO 123
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Thr Cys Arg Ala Ser Gln Gly Ile Arg Asn Ser Leu Ala Trp Tyr Gln
1               5                   10                  15

Gln Lys Pro Gly Lys Ala Pro Lys
            20

<210> SEQ ID NO 124
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Cys Arg Ala Ser Gln Gly Ile Arg Asn Tyr Leu Gly Trp Tyr Gln
1               5                   10                  15

Gln Lys Pro Gly Lys Ala Pro Lys
            20

<210> SEQ ID NO 125
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Thr Cys Arg Ala Ser Gln Gly Ile Arg Asn Tyr Leu Ser Trp Tyr Gln
1               5                   10                  15

Gln Lys Pro Gly Lys Ala Pro Lys
            20

```
<210> SEQ ID NO 126
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Cys Arg Ala Ser Asn Gly Ile Arg Asn Gln Leu Ala Trp Tyr Gln
1               5                   10                  15

Gln Lys Pro Gly Lys Ala Pro Lys
            20

<210> SEQ ID NO 127
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Thr Cys Arg Ala Ser Gly Gly Ile Arg Asn Gln Leu Ala Trp Tyr Gln
1               5                   10                  15

Gln Lys Pro Gly Lys Ala Pro Lys
            20

<210> SEQ ID NO 128
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Thr Cys Arg Ala Ser His Gly Ile Arg Asn Gln Leu Ala Trp Tyr Gln
1               5                   10                  15

Gln Lys Pro Gly Lys Ala Pro Lys
            20

<210> SEQ ID NO 129
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Cys Arg Ala Ser Ser Gly Ile Arg Asn Gln Leu Ala Trp Tyr Gln
1               5                   10                  15

Gln Lys Pro Gly Lys Ala Pro Lys
            20

<210> SEQ ID NO 130
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Thr Cys Arg Ala Ser Arg Gly Ile Arg Asn Gln Leu Ala Trp Tyr Gln
```

Gln Lys Pro Gly Lys Ala Pro Lys
            20

<210> SEQ ID NO 131
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Thr Cys Arg Ala Ser Gln Ser Ile Arg Asn Gln Leu Ala Trp Tyr Gln
1               5                   10                  15

Gln Lys Pro Gly Lys Ala Pro Lys
            20

<210> SEQ ID NO 132
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Thr Cys Arg Ala Ser Gln His Ile Arg Asn Gln Leu Ala Trp Tyr Gln
1               5                   10                  15

Gln Lys Pro Gly Lys Ala Pro Lys
            20

<210> SEQ ID NO 133
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Cys Arg Ala Ser Gln Asn Ile Arg Asn Gln Leu Ala Trp Tyr Gln
1               5                   10                  15

Gln Lys Pro Gly Lys Ala Pro Lys
            20

<210> SEQ ID NO 134
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Cys Arg Ala Ser Gln Gly Val Arg Asn Gln Leu Ala Trp Tyr Gln
1               5                   10                  15

Gln Lys Pro Gly Lys Ala Pro Lys
            20

<210> SEQ ID NO 135
<211> LENGTH: 24
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 135

Thr Cys Arg Ala Ser Gln Gly Thr Arg Asn Gln Leu Ala Trp Tyr Gln
1               5                   10                  15

Gln Lys Pro Gly Lys Ala Pro Lys
            20

<210> SEQ ID NO 136
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Thr Cys Arg Ala Ser Gln Gly Ile Gln Asn Gln Leu Ala Trp Tyr Gln
1               5                   10                  15

Gln Lys Pro Gly Lys Ala Pro Lys
            20

<210> SEQ ID NO 137
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Thr Cys Arg Ala Ser Gln Gly Ile Arg Gly Gln Leu Ala Trp Tyr Gln
1               5                   10                  15

Gln Lys Pro Gly Lys Ala Pro Lys
            20

<210> SEQ ID NO 138
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Thr Cys Arg Ala Ser Gln Gly Ile Arg Thr Gln Leu Ala Trp Tyr Gln
1               5                   10                  15

Gln Lys Pro Gly Lys Ala Pro Lys
            20

<210> SEQ ID NO 139
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Thr Cys Arg Ala Ser Gln Gly Ile Arg Ser Gln Leu Ala Trp Tyr Gln
1               5                   10                  15

Gln Lys Pro Gly Lys Ala Pro Lys
            20
```

```
<210> SEQ ID NO 140
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Thr Cys Arg Ala Ser Gln Gly Ile Arg Ser Gln Leu Gly Trp Tyr Gln
1               5                   10                  15

Gln Lys Pro Gly Lys Ala Pro Lys
            20

<210> SEQ ID NO 141
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Thr Cys Arg Ala Ser Gln Gly Ile Arg Ser Gln Leu Ser Trp Tyr Gln
1               5                   10                  15

Gln Lys Pro Gly Lys Ala Pro Lys
            20

<210> SEQ ID NO 142
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Thr Cys Arg Ala Ser Asn Gly Ile Arg Asn Ser Leu Ala Trp Tyr Gln
1               5                   10                  15

Gln Lys Pro Gly Lys Ala Pro Lys
            20

<210> SEQ ID NO 143
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Thr Cys Arg Ala Ser Gly Gly Ile Arg Asn Ser Leu Ala Trp Tyr Gln
1               5                   10                  15

Gln Lys Pro Gly Lys Ala Pro Lys
            20

<210> SEQ ID NO 144
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144
```

Thr Cys Arg Ala Ser His Gly Ile Arg Asn Ser Leu Ala Trp Tyr Gln
1               5                   10                  15

Gln Lys Pro Gly Lys Ala Pro Lys
            20

<210> SEQ ID NO 145
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Thr Cys Arg Ala Ser Ser Gly Ile Arg Asn Ser Leu Ala Trp Tyr Gln
1               5                   10                  15

Gln Lys Pro Gly Lys Ala Pro Lys
            20

<210> SEQ ID NO 146
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Thr Cys Arg Ala Ser Arg Gly Ile Arg Asn Ser Leu Ala Trp Tyr Gln
1               5                   10                  15

Gln Lys Pro Gly Lys Ala Pro Lys
            20

<210> SEQ ID NO 147
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Thr Cys Arg Ala Ser Gln Ser Ile Arg Asn Ser Leu Ala Trp Tyr Gln
1               5                   10                  15

Gln Lys Pro Gly Lys Ala Pro Lys
            20

<210> SEQ ID NO 148
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Thr Cys Arg Ala Ser Gln His Ile Arg Asn Ser Leu Ala Trp Tyr Gln
1               5                   10                  15

Gln Lys Pro Gly Lys Ala Pro Lys
            20

<210> SEQ ID NO 149
<211> LENGTH: 24
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 149

Thr Cys Arg Ala Ser Gln Asn Ile Arg Asn Ser Leu Ala Trp Tyr Gln
1               5                   10                  15

Gln Lys Pro Gly Lys Ala Pro Lys
            20

<210> SEQ ID NO 150
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Thr Cys Arg Ala Ser Gln Gly Val Arg Asn Ser Leu Ala Trp Tyr Gln
1               5                   10                  15

Gln Lys Pro Gly Lys Ala Pro Lys
            20

<210> SEQ ID NO 151
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Thr Cys Arg Ala Ser Gln Gly Thr Arg Asn Ser Leu Ala Trp Tyr Gln
1               5                   10                  15

Gln Lys Pro Gly Lys Ala Pro Lys
            20

<210> SEQ ID NO 152
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Thr Cys Arg Ala Ser Gln Gly Ile Gln Asn Ser Leu Ala Trp Tyr Gln
1               5                   10                  15

Gln Lys Pro Gly Lys Ala Pro Lys
            20

<210> SEQ ID NO 153
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Thr Cys Arg Ala Ser Gln Gly Ile Arg Gly Ser Leu Ala Trp Tyr Gln
1               5                   10                  15

Gln Lys Pro Gly Lys Ala Pro Lys
            20
```

<210> SEQ ID NO 154
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Thr Cys Arg Ala Ser Gln Gly Ile Arg Thr Ser Leu Ala Trp Tyr Gln
1               5                   10                  15

Gln Lys Pro Gly Lys Ala Pro Lys
            20

<210> SEQ ID NO 155
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Thr Cys Arg Ala Ser Gln Gly Ile Arg Ser Ser Leu Ala Trp Tyr Gln
1               5                   10                  15

Gln Lys Pro Gly Lys Ala Pro Lys
            20

<210> SEQ ID NO 156
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Thr Cys Arg Ala Ser Gln Gly Ile Arg Asn Ser Leu Gly Trp Tyr Gln
1               5                   10                  15

Gln Lys Pro Gly Lys Ala Pro Lys
            20

<210> SEQ ID NO 157
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Thr Cys Arg Ala Ser Gln Gly Ile Arg Asn Ser Leu Ser Trp Tyr Gln
1               5                   10                  15

Gln Lys Pro Gly Lys Ala Pro Lys
            20

<210> SEQ ID NO 158
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

```
Thr Cys Arg Ala Ser Asn Gly Ile Arg Asn Tyr Leu Gly Trp Tyr Gln
1               5                   10                  15

Gln Lys Pro Gly Lys Ala Pro Lys
            20

<210> SEQ ID NO 159
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Thr Cys Arg Ala Ser Gly Gly Ile Arg Asn Tyr Leu Gly Trp Tyr Gln
1               5                   10                  15

Gln Lys Pro Gly Lys Ala Pro Lys
            20

<210> SEQ ID NO 160
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Cys Arg Ala Ser His Gly Ile Arg Asn Tyr Leu Gly Trp Tyr Gln
1               5                   10                  15

Gln Lys Pro Gly Lys Ala Pro Lys
            20

<210> SEQ ID NO 161
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Thr Cys Arg Ala Ser Ser Gly Ile Arg Asn Tyr Leu Gly Trp Tyr Gln
1               5                   10                  15

Gln Lys Pro Gly Lys Ala Pro Lys
            20

<210> SEQ ID NO 162
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Thr Cys Arg Ala Ser Arg Gly Ile Arg Asn Tyr Leu Gly Trp Tyr Gln
1               5                   10                  15

Gln Lys Pro Gly Lys Ala Pro Lys
            20

<210> SEQ ID NO 163
<211> LENGTH: 24
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 163

Thr Cys Arg Ala Ser Gln Ser Ile Arg Asn Tyr Leu Gly Trp Tyr Gln
1               5                   10                  15

Gln Lys Pro Gly Lys Ala Pro Lys
            20

<210> SEQ ID NO 164
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Thr Cys Arg Ala Ser Gln His Ile Arg Asn Tyr Leu Gly Trp Tyr Gln
1               5                   10                  15

Gln Lys Pro Gly Lys Ala Pro Lys
            20

<210> SEQ ID NO 165
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Thr Cys Arg Ala Ser Gln Asn Ile Arg Asn Tyr Leu Gly Trp Tyr Gln
1               5                   10                  15

Gln Lys Pro Gly Lys Ala Pro Lys
            20

<210> SEQ ID NO 166
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Thr Cys Arg Ala Ser Gln Gly Val Arg Asn Tyr Leu Gly Trp Tyr Gln
1               5                   10                  15

Gln Lys Pro Gly Lys Ala Pro Lys
            20

<210> SEQ ID NO 167
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Thr Cys Arg Ala Ser Gln Gly Thr Arg Asn Tyr Leu Gly Trp Tyr Gln
1               5                   10                  15

Gln Lys Pro Gly Lys Ala Phe Lys
```

-continued

20

<210> SEQ ID NO 168
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Thr Cys Arg Ala Ser Gln Gly Ile Gln Asn Tyr Leu Gly Trp Tyr Gln
1               5                   10                  15

Gln Lys Pro Gly Lys Ala Pro Lys
            20

<210> SEQ ID NO 169
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Thr Cys Arg Ala Ser Gln Gly Ile Arg Gly Tyr Leu Gly Trp Tyr Gln
1               5                   10                  15

Gln Lys Pro Gly Lys Ala Pro Lys
            20

<210> SEQ ID NO 170
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Thr Cys Arg Ala Ser Gln Gly Ile Arg Thr Tyr Leu Gly Trp Tyr Gln
1               5                   10                  15

Gln Lys Pro Gly Lys Ala Pro Lys
            20

<210> SEQ ID NO 171
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Thr Cys Arg Ala Ser Gln Gly Ile Arg Ser Tyr Leu Gly Trp Tyr Gln
1               5                   10                  15

Gln Lys Pro Gly Lys Ala Pro Lys
            20

<210> SEQ ID NO 172
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 172

Thr Cys Arg Ala Ser Asn Gly Ile Arg Asn Tyr Leu Ser Trp Tyr Gln
1               5                   10                  15

Gln Lys Pro Gly Lys Ala Pro Lys
            20

<210> SEQ ID NO 173
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Thr Cys Arg Ala Ser Gly Gly Ile Arg Asn Tyr Leu Ser Trp Tyr Gln
1               5                   10                  15

Gln Lys Pro Gly Lys Ala Pro Lys
            20

<210> SEQ ID NO 174
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Thr Cys Arg Ala Ser His Gly Ile Arg Asn Tyr Leu Ser Trp Tyr Gln
1               5                   10                  15

Gln Lys Pro Gly Lys Ala Pro Lys
            20

<210> SEQ ID NO 175
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Thr Cys Arg Ala Ser Ser Gly Ile Arg Asn Tyr Leu Ser Trp Tyr Gln
1               5                   10                  15

Gln Lys Pro Gly Lys Ala Pro Lys
            20

<210> SEQ ID NO 176
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Thr Cys Arg Ala Ser Gln Gly Ile Gln Asn Tyr Leu Ser Trp Tyr Gln
1               5                   10                  15

Gln Lys Pro Gly Lys Ala Pro Lys
            20

<210> SEQ ID NO 177
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Thr Cys Arg Ala Ser Gln Gly Ile Arg Thr Tyr Leu Ser Trp Tyr Gln
1               5                   10                  15

Gln Lys Pro Gly Lys Ala Pro Lys
            20

<210> SEQ ID NO 178
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Thr Cys Arg Ala Ser Arg Gly Ile Arg Asn Tyr Leu Ser Trp Tyr Gln
1               5                   10                  15

Gln Lys Pro Gly Lys Ala Pro Lys
            20

<210> SEQ ID NO 179
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Thr Cys Arg Ala Ser Gln Ser Ile Arg Asn Tyr Leu Ser Trp Tyr Gln
1               5                   10                  15

Gln Lys Pro Gly Lys Ala Pro Lys
            20

<210> SEQ ID NO 180
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Thr Cys Arg Ala Ser Gln Gly Ile Arg Ser Tyr Leu Ser Trp Tyr Gln
1               5                   10                  15

Gln Lys Pro Gly Lys Ala Pro Lys
            20

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Arg Ala Ser Gln Gly Ile Gln Asn Tyr Leu Ala
1               5                   10
```

<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Arg Ala Ser Gln Gly Ile Arg Asn Tyr Leu Ser
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Ala Ser Gln Gly Ile Gln Asn Tyr Leu Ser
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Ala Ser Gln Gly Ile Arg Thr Tyr Leu Ala
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Arg Ala Ser Gln Gly Ile Arg Thr Tyr Leu Ser
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Ala Ser Gln Gly Thr Arg Asn Tyr Leu Ala
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 187

Arg Ala Ser Gln Gly Ile Arg Asn Tyr Leu Gly
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Ala Ser Gln Gly Thr Arg Asn Tyr Leu Gly
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Arg Ala Ser Gly Gly Ile Arg Asn Tyr Leu Ala
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Arg Ala Ser Gly Gly Ile Arg Asn Tyr Leu Ser
1               5                   10

<210> SEQ ID NO 191
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Arg Ala Ser Gly Gly Ile Arg Asn Tyr Leu Gly
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Arg Ala Ser Gln Gly Ile Arg Thr Tyr Leu Gly
1               5                   10

<210> SEQ ID NO 193
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 193

Arg Ala Ser His Gly Ile Arg Asn Tyr Leu Ala
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Ala Ser His Gly Ile Arg Asn Tyr Leu Ser
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Arg Ala Ser Arg Gly Ile Arg Asn Tyr Leu Ala
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Arg Ala Ser Arg Gly Ile Arg Asn Tyr Leu Ser
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Arg Ala Ser Gln Ser Ile Arg Asn Tyr Leu Ala
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Arg Ala Ser Gln Ser Ile Arg Asn Tyr Leu Ser
1               5                   10
```

```
<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Arg Ala Ser Gln Gly Ile Arg Ser Tyr Leu Ser
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Arg Ala Ser Gln Gly Thr Arg Asn Tyr Leu Ser
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Arg Ala Ser Gln Gly Ile Arg Thr Tyr Leu Gly
1               5                   10

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Asp Tyr Thr Met His
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Glu Tyr Ala Met His
1               5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 204

Gln His Ala Leu His
1               5

<210> SEQ ID NO 205
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gln His Ala Met His
1               5

<210> SEQ ID NO 206
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

His Tyr Ala Leu His
1               5

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gln Tyr Ala Met His
1               5

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

His Tyr Ala Met His
1               5

<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Tyr Tyr Ala Met His
1               5

<210> SEQ ID NO 210
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Pro Ala Ile Thr Trp Asn Ser Gly His Ile Asp Tyr Ala Asp Ser Val
1               5                   10                  15

Glu Gly

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Thr Trp Asn Ser Gly His Ile Asp Tyr Ala Asp Ser Val Glu Gly
1               5                   10                  15

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any amino acid

<400> SEQUENCE: 212

Pro Val Ser Tyr Leu Ser Thr Ala Ser Ser Leu Asp Xaa
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Pro Ala Ser Tyr Leu Ser Thr Ala Ser Ser Leu Asp Tyr
1               5                   10

<210> SEQ ID NO 214
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Pro Ala Ser Tyr Leu Ser Thr Ser Ser Ser Leu Asp Tyr
1               5                   10

<210> SEQ ID NO 215
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 215

Val Ser Tyr Leu Ser Thr Ala Ser Ser Leu Asp Asn
1               5                   10

<210> SEQ ID NO 216
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid

<400> SEQUENCE: 216

Val Ser Tyr Leu Ser Thr Ala Ser Ser Leu Asp Xaa
1               5                   10

<210> SEQ ID NO 217
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Ser Tyr Leu Ser Thr Ser Ser Ser Leu Asp Tyr
1               5                   10

<210> SEQ ID NO 218
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Val Ser Tyr Leu Ser Thr Ala Ser Ser Leu Gln Tyr
1               5                   10

<210> SEQ ID NO 219
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ala Ser Tyr Leu Ser Thr Ala Ser Ser Leu Gln Tyr
1               5                   10

<210> SEQ ID NO 220
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220
```

```
Val Ser Tyr Leu Ser Thr Ser Ser Ser Leu Asp Tyr
1               5                   10
```

<210> SEQ ID NO 221
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

```
Ala Ser Tyr Leu Ser Thr Ala Ser Ser Leu Glu Tyr
1               5                   10
```

<210> SEQ ID NO 222
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

```
Ala Ser Tyr Leu Ser Thr Ser Ser Ser Leu Asp Asn
1               5                   10
```

<210> SEQ ID NO 223
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

```
Ala Ser Tyr Leu Ser Thr Ser Ser Ser Leu Asp Lys
1               5                   10
```

<210> SEQ ID NO 224
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

```
Ala Ser Tyr Leu Ser Thr Ser Ser Ser Leu Asp Asp
1               5                   10
```

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

```
Ala Ser Tyr Leu Ser Thr Ser Phe Ser Leu Asp Tyr
1               5                   10
```

<210> SEQ ID NO 226
<211> LENGTH: 12
<212> TYPE: PRT
<213> ORGANISM: Artificial Sequence
<220> FEATURE:

<223> OTHER INFORMATION: Description of Artificial Sequence: Synthetic
       peptide

<400> SEQUENCE: 226

Val Ser Tyr Leu Ser Thr Ala Ser Ser Leu Asp Ala
1               5                   10

<210> SEQ ID NO 227
<211> LENGTH: 12
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 227

Ala Ser Tyr Leu Ser Thr Ser Ser Ser Leu Glu Tyr
1               5                   10

<210> SEQ ID NO 228
<211> LENGTH: 12
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 228

Val Ser Tyr Leu Ser Thr Ser Ser Ser Leu Asp Asn
1               5                   10

<210> SEQ ID NO 229
<211> LENGTH: 12
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 229

Val Ser Tyr Leu Ser Thr Ala Ser Ser Ala Asp Tyr
1               5                   10

<210> SEQ ID NO 230
<211> LENGTH: 12
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 230

Val Ser Tyr Leu Ser Thr Ala Ser Ser Leu Ala Tyr
1               5                   10

<210> SEQ ID NO 231
<211> LENGTH: 12
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 231

Val Ala Tyr Leu Ser Thr Ala Ser Ser Leu Asp Tyr
1               5                   10

```
<210> SEQ ID NO 232
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Val Ser Ala Leu Ser Thr Ala Ser Ser Leu Asp Tyr
1               5                   10

<210> SEQ ID NO 233
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Val Ser Tyr Ala Ser Thr Ala Ser Ser Leu Asp Tyr
1               5                   10

<210> SEQ ID NO 234
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Val Ser Tyr Leu Ala Thr Ala Ser Ser Leu Asp Tyr
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Val Ser Tyr Leu Ser Ala Ala Ser Ser Leu Asp Tyr
1               5                   10

<210> SEQ ID NO 236
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Val Ser Tyr Leu Ser Thr Ala Ala Ser Leu Asp Tyr
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237
```

```
Val Ser Tyr Leu Ser Thr Ala Ser Ala Leu Asp Tyr
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid

<400> SEQUENCE: 238

Val Ser Tyr Leu Ser Thr Ala Ser Ser Leu Gln Xaa
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Val Ser Tyr Leu Ser Thr Ala Ser Ser Leu Gln Tyr
1               5                   10

<210> SEQ ID NO 240
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Val Ser Ala Ser Thr Gly Pro Ser Val Phe Pro Leu
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Val His Tyr Leu Ser Thr Ala Ser Ser Leu Asp Tyr
1               5                   10

<210> SEQ ID NO 242
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Val His Tyr Leu Ser Thr Ala Ser Gln Leu His His
1               5                   10
```

```
<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Val Gln Tyr Leu Ser Thr Ala Ser Ser Leu Asp Tyr
1               5                   10

<210> SEQ ID NO 244
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Val Lys Tyr Leu Ser Thr Ala Ser Ser Leu Asp Tyr
1               5                   10

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Val Pro Tyr Leu Ser Thr Ala Ser Ser Leu Asp Tyr
1               5                   10

<210> SEQ ID NO 246
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Val Ser Tyr Leu Ser Thr Ala Ser Pro Leu Asp Tyr
1               5                   10

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Val Ser Tyr Leu Ser Thr Ala Ser Ser Leu Pro Tyr
1               5                   10

<210> SEQ ID NO 248
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248
```

```
Val Ser Tyr Leu Ser Thr Ala Ser Ser Leu Asp Pro
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Val Ser Tyr Leu Ser Thr Ala Ser Ser Leu Asp Ser
1               5                   10

<210> SEQ ID NO 250
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ala Ser Tyr Leu Ser Thr Ala Ser Ser Leu Asp Tyr
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ala Ser Tyr Leu Ser Thr Ser Ser Ser Leu His Tyr
1               5                   10

<210> SEQ ID NO 252
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ala Ser Phe Leu Ser Thr Ser Ser Ser Leu Glu Tyr
1               5                   10

<210> SEQ ID NO 253
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Pro Arg Ala Ser Gln Gly Ile Arg Asn Tyr Leu Ala
1               5                   10

<210> SEQ ID NO 254
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 254

Arg Ala Ser Gln Gly Ile Arg Asn Asp Leu Gly
1               5                   10

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Arg Ala Ser Gln Gly Ile Ser Asn Tyr Leu Ala
1               5                   10

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Arg Ala Arg Gln Gly Ile Ser Asn Tyr Leu Ala
1               5                   10

<210> SEQ ID NO 257
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Arg Ala Ser Gln Ser Ile Arg Ser Asn Tyr Leu Ala
1               5                   10

<210> SEQ ID NO 258
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Arg Ala Ser Gln Glu Ile Arg Asn Tyr Leu Ala
1               5                   10

<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

His Ala Ser Gln Lys Ile Arg Asn Tyr Leu Ala
1               5                   10
```

```
<210> SEQ ID NO 260
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Arg Ala Ser Leu Gly Ile Arg Asn Tyr Leu Ala
1               5                   10

<210> SEQ ID NO 261
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Arg Ala Ser Gln Gly Ile Ser Ser Tyr Leu Ala
1               5                   10

<210> SEQ ID NO 262
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Arg Ala Ser Ser Gly Ile Arg Asn Tyr Leu Ala
1               5                   10

<210> SEQ ID NO 263
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

His Ala Ser Arg Arg Ile Arg Asn Tyr Leu Ala
1               5                   10

<210> SEQ ID NO 264
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

His Ala Ser Arg Arg Ile Leu Asn Tyr Leu Ala
1               5                   10

<210> SEQ ID NO 265
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 265

His Ala Ser Arg Lys Ile Leu Asn Tyr Leu Ala
1               5                   10

<210> SEQ ID NO 266
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

His Ala Ser Arg Lys Ile Arg Asn Tyr Leu Ala
1               5                   10

<210> SEQ ID NO 267
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

His Ala Ser Gln Lys Ile Arg Asn Tyr Leu Ala
1               5                   10

<210> SEQ ID NO 268
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

His Ala Ser Lys Arg Ile Arg Asn Tyr Leu Ala
1               5                   10

<210> SEQ ID NO 269
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

His Ala Ser Lys Lys Ile Arg Asn Tyr Leu Ala
1               5                   10

<210> SEQ ID NO 270
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

His Ala Ser Arg Glu Ile Arg Asn Tyr Leu Ala
1               5                   10

<210> SEQ ID NO 271
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 271

His Ala Ser Gln Gly Ile Arg Asn Tyr Leu Ala
1               5                   10

<210> SEQ ID NO 272
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ala Ala Ser Tyr Arg Gln
1               5

<210> SEQ ID NO 273
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gly Ala Ser Gln Gly Ile Arg Asn Tyr Leu Ala
1               5                   10

<210> SEQ ID NO 274
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Arg Ala Ser Lys Gly Ile Arg Asn Tyr Leu Ala
1               5                   10

<210> SEQ ID NO 275
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Arg Ala Ser Gln Lys Ile Arg Asn Tyr Leu Ala
1               5                   10

<210> SEQ ID NO 276
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Arg Ala Ser Gln Gly Lys Arg Asn Tyr Leu Ala
1               5                   10
```

```
<210> SEQ ID NO 277
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Arg Ala Ser Gln Gly Leu Arg Asn Tyr Leu Ala
1               5                   10

<210> SEQ ID NO 278
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Arg Ala Ser Tyr Gly Ile Arg Asn Tyr Leu Ala
1               5                   10

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Pro Ala Ala Ser Thr Leu Gln Ser
1               5

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ala Ala Ser Ser Leu Leu His
1               5

<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ala Ala Ser Ser Leu Gln Pro
1               5

<210> SEQ ID NO 282
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 282

Ala Ala Ser Ser Leu Leu Arg
1               5

<210> SEQ ID NO 283
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ala Ala Ser Ser Leu Leu Lys
1               5

<210> SEQ ID NO 284
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ala Ala Ser Ser Leu Gln Gln
1               5

<210> SEQ ID NO 285
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Ala Ser Ser Leu Leu Pro
1               5

<210> SEQ ID NO 286
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ala Ala Ser Ser Leu Leu Gln
1               5

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ala Ala Ser Thr Leu Leu Lys
1               5

<210> SEQ ID NO 288
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ala Ala Ser Ala Leu Gln Ser
1               5

<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ala Ala Ser Thr Phe Gln Ser
1               5

<210> SEQ ID NO 290
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ala Ala Ser Thr Leu Gln Lys
1               5

<210> SEQ ID NO 291
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ala Ala Leu Thr Leu Gln Ser
1               5

<210> SEQ ID NO 292
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ala Ala Ser Thr Leu Leu Ser
1               5

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ala Ala Ser Thr Leu Gln Pro
```

```
<210> SEQ ID NO 294
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ala Ala Ser Ser Leu Gln Ser
1               5

<210> SEQ ID NO 295
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ala Ala Tyr Thr Leu Gln Ser
1               5

<210> SEQ ID NO 296
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Pro Gln Lys Tyr Asn Arg Ala Pro Tyr Thr
1               5                   10

<210> SEQ ID NO 297
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid

<400> SEQUENCE: 297

Pro Gln Arg Tyr Asn Arg Ala Pro Tyr Xaa
1               5                   10

<210> SEQ ID NO 298
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Pro Gln Arg Tyr Asn Arg Ala Pro Tyr Ala
1               5                   10

<210> SEQ ID NO 299
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gln Lys Tyr Asn Arg Ala Pro Tyr Thr
1               5

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gln Arg Tyr Asn Arg Ala Pro Tyr Ala
1               5

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid

<400> SEQUENCE: 301

Gln Arg Tyr Asn Arg Ala Pro Tyr Xaa
1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gln Arg Tyr Asn Arg Ala Pro Tyr Thr
1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gln Lys Tyr Asn Ser Ala Pro Tyr Ala
1               5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 304

Gln Lys Tyr Asn Arg Ala Pro Tyr Ala
1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gln Lys Tyr Asn Arg Ala Pro Tyr Thr
1               5

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gln Lys Tyr Ser Ser Ala Pro Tyr Thr
1               5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gln Lys Tyr Asn Ser Ala Pro Tyr Thr
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gln Lys Tyr Asn Ser Ala Pro Tyr Tyr
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gln Lys Tyr Asn Ser Ala Pro Tyr Asn
1               5

<210> SEQ ID NO 310
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gln Lys Tyr Thr Ser Ala Pro Tyr Thr
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gln Lys Tyr Asn Arg Ala Pro Tyr Asn
1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gln Lys Tyr Asn Ser Ala Ala Tyr Ser
1               5

<210> SEQ ID NO 313
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gln Gln Tyr Asn Ser Ala Pro Asp Thr
1               5

<210> SEQ ID NO 314
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gln Lys Tyr Asn Ser Asp Pro Tyr Thr
1               5

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gln Lys Tyr Ile Ser Ala Pro Tyr Thr
```

1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gln Lys Tyr Asn Arg Pro Pro Tyr Thr
1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gln Arg Tyr Asn Asp Ala Pro Tyr Thr
1               5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Gln Arg Tyr Ala Arg Ala Pro Tyr Thr
1               5

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gln Arg Tyr Asn Ala Ala Pro Tyr Thr
1               5

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gln Arg Tyr Asn Arg Ala Ala Tyr Thr
1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 321

Gln Arg Tyr Asn Arg Ala Pro Ala Thr
1               5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gln Pro Glu Asp Phe Ala Thr Tyr Tyr
1               5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Gln Ser Asp Asn Phe Ala Thr Tyr Tyr
1               5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Gln Arg Tyr Asp Lys Pro Pro Tyr Thr
1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Gln Arg Tyr Asn Lys Pro Pro Tyr Thr
1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gln Arg Tyr Asp Arg Pro Pro Tyr Thr
1               5

<210> SEQ ID NO 327

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Gln Arg Tyr Asp Arg Ala Pro Tyr Thr
1               5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gln Arg Tyr Asn Lys Ala Pro Tyr Thr
1               5

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gln Arg Tyr Asn Arg Pro Pro Tyr Thr
1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Gln Lys Tyr Gln Arg Ala Pro Tyr Thr
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gln Lys Tyr Ser Ser Ala Pro Tyr Ala
1               5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332
```

Ala Arg Tyr Asn Arg Ala Pro Tyr Thr
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gln Ala Tyr Asn Arg Ala Pro Tyr Thr
1               5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Gln Arg Ala Asn Arg Ala Pro Tyr Thr
1               5

<210> SEQ ID NO 335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gln Pro Glu Asp Val Ala Thr Tyr Tyr
1               5

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Gln Pro Glu Asp Val Ala Ala Tyr Tyr
1               5

<210> SEQ ID NO 337
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Asn Tyr Ala Met His
1               5

<210> SEQ ID NO 338
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 338

Thr Tyr Ala Met His
1               5

<210> SEQ ID NO 339
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Arg Tyr Ala Met His
1               5

<210> SEQ ID NO 340
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Asp Phe Ala Met His
1               5

<210> SEQ ID NO 341
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Asp Gln Ala Met His
1               5

<210> SEQ ID NO 342
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Asp Tyr Ala Ile His
1               5

<210> SEQ ID NO 343
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Gly Ile Thr Trp Asn Ser Gly His Ile Asp Tyr Ala Asp Ser Val Glu
1               5                   10                  15

Gly
```

```
<210> SEQ ID NO 344
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ala Ile Thr Trp Asn Ser Gly His Thr Asp Tyr Ala Asp Ser Val Glu
1               5                   10                  15

Gly

<210> SEQ ID NO 345
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Ala Ile Thr Trp Asn Ser Gly His Val Asp Tyr Ala Asp Ser Val Glu
1               5                   10                  15

Gly

<210> SEQ ID NO 346
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Ala Ile Thr Trp Asn Ser Gly His Ile Asp Tyr Ala Asp Ser Val Arg
1               5                   10                  15

Gly

<210> SEQ ID NO 347
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Ala Ile Thr Trp Asn Ser Gly His Ile Asp Tyr Ala Asp Ser Val Glu
1               5                   10                  15

Asn

<210> SEQ ID NO 348
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Val Ser Tyr Leu Ser Thr Ala Pro Ser Leu Asp Tyr
1               5                   10
```

```
<210> SEQ ID NO 349
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Leu Ala Ser Gln Gly Ile Arg Asn Tyr Leu Ala
1               5                   10

<210> SEQ ID NO 350
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Ala Ala Ser Gln Gly Ile Arg Asn Tyr Leu Ala
1               5                   10

<210> SEQ ID NO 351
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Thr Ala Ser Gln Gly Ile Arg Asn Tyr Leu Ala
1               5                   10

<210> SEQ ID NO 352
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Arg Ser Ser Gln Gly Ile Arg Asn Tyr Leu Ala
1               5                   10

<210> SEQ ID NO 353
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Arg Gly Ser Gln Gly Ile Arg Asn Tyr Leu Ala
1               5                   10

<210> SEQ ID NO 354
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 354

Arg Thr Ser Gln Gly Ile Arg Asn Tyr Leu Ala
1               5                   10

<210> SEQ ID NO 355
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Arg Ala Thr Gln Gly Ile Arg Asn Tyr Leu Ala
1               5                   10

<210> SEQ ID NO 356
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Arg Ala Ser Met Gly Ile Arg Asn Tyr Leu Ala
1               5                   10

<210> SEQ ID NO 357
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Arg Ala Ser Val Gly Ile Arg Asn Tyr Leu Ala
1               5                   10

<210> SEQ ID NO 358
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Arg Ala Ser Trp Gly Ile Arg Asn Tyr Leu Ala
1               5                   10

<210> SEQ ID NO 359
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Arg Ala Ser Gln Pro Ile Arg Asn Tyr Leu Ala
1               5                   10

<210> SEQ ID NO 360
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 360

Arg Ala Ser Gln Arg Ile Arg Asn Tyr Leu Ala
1               5                   10

<210> SEQ ID NO 361
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Arg Ala Ser Gln Leu Ile Arg Asn Tyr Leu Ala
1               5                   10

<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Arg Ala Ser Gln Gly Val Arg Asn Tyr Leu Ala
1               5                   10

<210> SEQ ID NO 363
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ala Ala Gly Thr Leu Gln Ser
1               5

<210> SEQ ID NO 364
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ala Ala Trp Thr Leu Gln Ser
1               5

<210> SEQ ID NO 365
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ala Ala Ser Gly Leu Gln Ser
1               5
```

<210> SEQ ID NO 366
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ala Ala Ser Thr Ser Gln Ser
1               5

<210> SEQ ID NO 367
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Ala Ala Ser Thr Thr Gln Ser
1               5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ala Ala Ser Thr Leu Ile Ser
1               5

<210> SEQ ID NO 369
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ala Ala Ser Thr Leu Gln Arg
1               5

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gln Arg Tyr Ile Arg Ala Pro Tyr Thr
1               5

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 371

Gln Arg Tyr Asn Gln Ala Pro Tyr Thr
1               5

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Gln Arg Tyr Asn Met Ala Pro Tyr Thr
1               5

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Gln Arg Tyr Asn Arg Ser Pro Tyr Thr
1               5

<210> SEQ ID NO 374
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Gln Arg Tyr Asn Arg Ala Gln Tyr Thr
1               5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gln Arg Tyr Asn Arg Ala Ala Tyr Thr
1               5

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gln Arg Tyr Asn Arg Ala Ser Tyr Thr
1               5

<210> SEQ ID NO 377
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Gln Arg Tyr Asn Arg Ala Met Tyr Thr
1               5

<210> SEQ ID NO 378
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Gln Arg Tyr Asn Arg Ala Glu Tyr Thr
1               5

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Gln Arg Tyr Asn Arg Ala Val Tyr Thr
1               5

<210> SEQ ID NO 380
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Ala Ala Lys His Arg Arg
1               5

<210> SEQ ID NO 381
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ala Ala Lys Gln Arg Lys
1               5

<210> SEQ ID NO 382
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Ala Ala Lys Tyr Lys Gln
```

```
1               5

<210> SEQ ID NO 383
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ala Ala Lys Tyr Leu Gln
1               5

<210> SEQ ID NO 384
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ala Ala Asn Val Arg Lys
1               5

<210> SEQ ID NO 385
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ala Ala Asn Trp Arg Arg
1               5

<210> SEQ ID NO 386
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ala Ala Arg Phe Arg Gln
1               5

<210> SEQ ID NO 387
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ala Ala Arg Phe Arg Arg
1               5

<210> SEQ ID NO 388
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                        peptide

<400> SEQUENCE: 388

Ala Ala Arg His Leu Lys
1               5

<210> SEQ ID NO 389
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Ala Ala Arg Trp Lys Arg
1               5

<210> SEQ ID NO 390
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Ala Ala Ser His Lys Lys
1               5

<210> SEQ ID NO 391
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Ala Ala Ser His Lys Arg
1               5

<210> SEQ ID NO 392
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Ala Ala Ser Trp Arg Arg
1               5
```